(12) United States Patent
Ried et al.

(10) Patent No.: US 8,741,574 B2
(45) Date of Patent: Jun. 3, 2014

(54) GENE EXPRESSION SIGNATURE OF GENOMIC INSTABILITY IN BREAST CANCER

(75) Inventors: Karl Thomas Ried, Bethesda, MD (US); Jens Habermann, Celle (DE); Nancy Lan Guo, Morgantown, WV (US); Gert Auer, Solna (SE)

(73) Assignees: The United States of America, as represented by the Secretary, Department of Health and Human Services, Washington, DC (US); West Virginia University Research Corporation, Morgantown, WV (US)

( * ) Notice: Subject to any disclaimer, the term of this patent is extended or adjusted under 35 U.S.C. 154(b) by 514 days.

(21) Appl. No.: 13/119,101

(22) PCT Filed: Sep. 15, 2009

(86) PCT No.: PCT/US2009/056931
§ 371 (c)(1),
(2), (4) Date: May 23, 2011

(87) PCT Pub. No.: WO2010/031035
PCT Pub. Date: Mar. 18, 2010

(65) Prior Publication Data
US 2011/0224089 A1    Sep. 15, 2011

Related U.S. Application Data

(60) Provisional application No. 61/097,101, filed on Sep. 15, 2008.

(51) Int. Cl.
*C12Q 1/68*    (2006.01)
(52) U.S. Cl.
USPC ..................................... 435/6.14; 424/9.351
(58) Field of Classification Search
None
See application file for complete search history.

(56) References Cited

U.S. PATENT DOCUMENTS

2005/0208500 A1    9/2005    Erlander et al.

OTHER PUBLICATIONS

Bergamaschi et al., "Distinct patterns of DNA copy number alteration are associated with different clinicopathological features and gene-expression subtypes of breast cancer," *Genes Chromosomes Cancer*, 45 (11), 1033-1040 (2006).
Blegen et al., "DNA amplifications and aneuploidy, high proliferative activity and impaired cell cycle control characterize breast carcinomas with poor prognosis," *Anal. Cell. Pathol.*, 25 (3), 103-114 (2003).
GenBank Accession No. AL157484.1 (Feb. 18, 2000).
GenBank Accession No. NC_000009.10 (Mar. 3, 2008).
GenBank Accession No. NC_000011.8 (Mar. 3, 2008).
GenBank Accession No. NC_000017.9 (Mar. 3, 2008).
GenBank Accession No. NC_000020.9 (Mar. 3, 2008).
GenBank Accession No. NM_000077.3 (Jul. 18, 2010).
GenBank Accession No. NM_001081491.1 (Mar. 12, 2011).
GenBank Accession No. NM_001609.3 (Mar. 4, 2010).
GenBank Accession No. NM_002988.2 (Mar. 12, 2011).
GenBank Accession No. NM_003462.3 (Feb. 19, 2011).
GenBank Accession No. NM_003600.2 (Apr. 9, 2011).
GenBank Accession No. NM_004496.2 (Mar. 20, 2011).
GenBank Accession No. NM_005375.2 (May 1, 2011).
GenBank Accession No. NM_006362.4 (Mar. 12, 2011).
GenBank Accession No. NM_015130.2 (Mar. 13, 2011).
GenBank Accession No. NM_032918.1 (May 7, 2010).
GenBank Accession No. NM_058195.2 (Jun. 27, 2010).
GenBank Accession No. NM_058197.3 (Jun. 27, 2010).
GenBank Accession No. NM_198433.1 (Apr. 9, 2011).
GenBank Accession No. NM_198434.1 (Apr. 9, 2011).
GenBank Accession No. NM_198435.1 (Apr. 9, 2011).
GenBank Accession No. NM_198436.1 (Apr. 9, 2011).
GenBank Accession No. NM_198437.1 (Apr. 9, 2011).
GenBank Accession No. U79293.1 (Nov. 28, 2000).
Habermann et al., "The gene expression signature of genomic instability in breast cancer is an independent predictor of clinical outcome," *Int. J. Cancer*, 124 (7), 1552-1564 (2009).
Haibe-Kains et al., "Comparison of prognostic gene expression signatures for breast cancer," *BMC Genomics*, 9 (21), 1-9 (2008).
Heselmeyer-Haddad et al., "Detection of chromosomal aneuploidies and gene copy number changes in fine needle aspirates is a specific, sensitive, and objective genetic test for the diagnosis of breast cancer," *Cancer Res.*, 62 (8), 2365-2369 (2002).
Kronenwett et al., "Characterisation of breast fine-needle aspiration biopsies by centrosome aberrations and genomic instability," *Br. J. Cancer*, 92 (2), 389-395 (2004).
Nuyten et al., "Combining biological gene expression signatures in predicting outcome in breast cancer: An alternative to supervised classification," *Eur. J. Cancer*, 44 (15), 2319-2329 (2008).
Paik et al., "A multigene assay to predict recurrence of tamoxifen-treated, node-negative breast cancer," *N. Eng. J. Med.*, 351 (27), 2817-2826 (2004).
Perou et al., "Molecular portraits of human breast tumours," *Nature*, 406 (6797), 747-752 (2000).

(Continued)

*Primary Examiner* — Jim Ketter
(74) *Attorney, Agent, or Firm* — Leydig, Voit & Mayer, Ltd.

(57) ABSTRACT

Methods of assessing genomic instability in breast cancer tissue by measuring the expression level of genes CDKN2A, SCYA18, STK15, NXF1, cDNA Dkfzp762M127, p28 KIAA0882, MYB, Human clone 23948, RERG, HNF3A, and ACADSB or a nucleic acid sequence comprising about 90% or greater sequence identity to SEQ ID NO: 21 in breast cancer tissue, an array suitable for use in such methods, and related methods and compositions.

13 Claims, 4 Drawing Sheets

(56) References Cited

OTHER PUBLICATIONS

Figure 1:
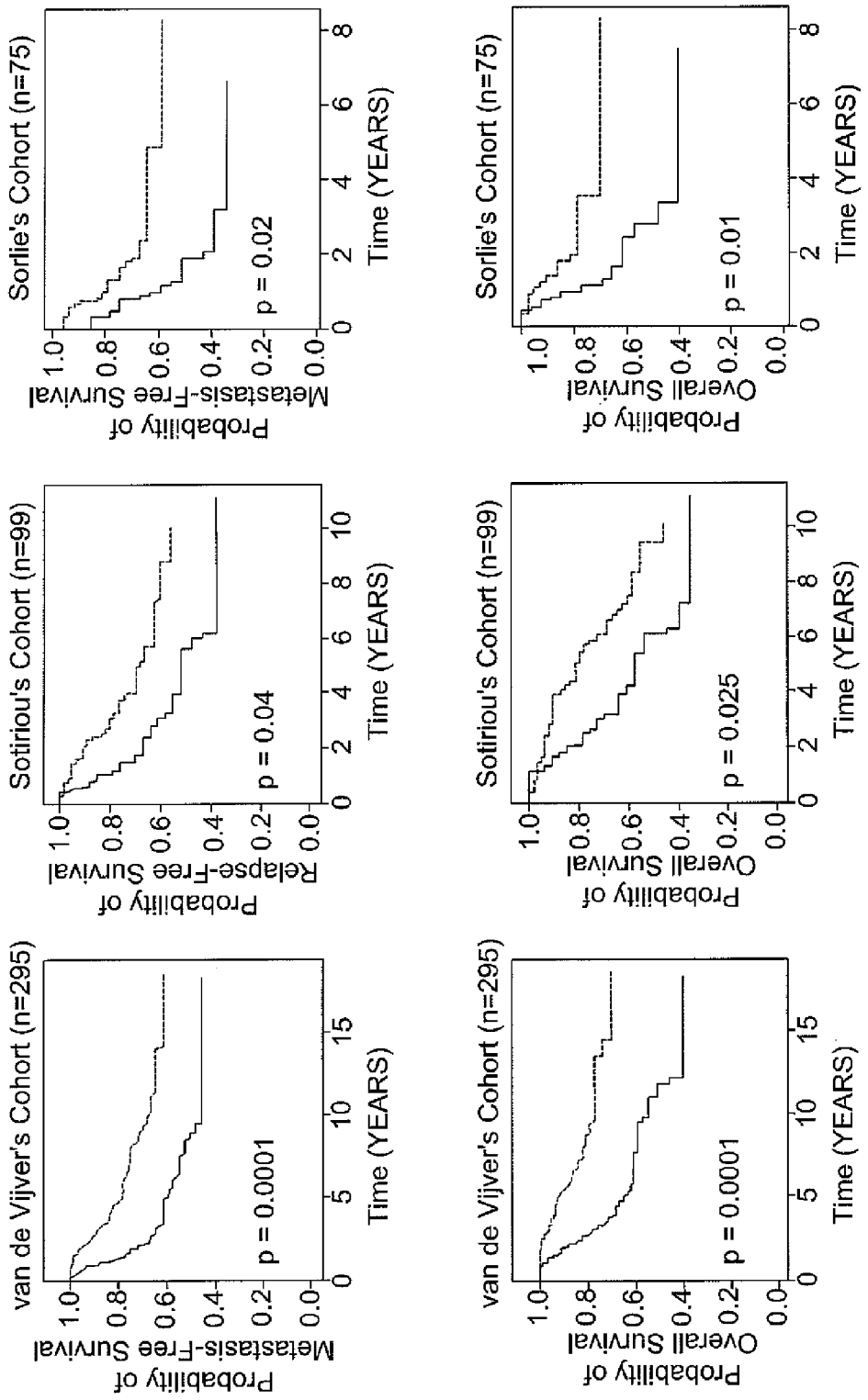

Rathnagiriswaran et al., "Identifying Genomic Signatures for Predicting Breast Cancer Outcomes," Thesis submitted to the College of Engineering and Mineral Resources, West Virginia University (2008).

Sørlie et al., "Repeated observation of breast tumor subtypes in independent gene expression data sets," *Proc. Natl. Acad. Sci.*, 100 (14), 8418-8423 (2003).

Sørlie et al., "Gene expression patterns of breast carcinomas distinguish tumor subclasses with clinical implications," *Proc. Natl. Acad. Sci.*, 98 (19), 10869-10874 (2001).

Sotiriou et al., "Breast cancer classification and prognosis based on gene expression profiles from a population-based study," *Proc. Natl. Acad. Sci.*, 100 (18), 10393-10398 (2003).

Van De Vijver et al., "A gene-expression signature as a predictor of survival in breast cancer," *N. Engl. J. Med.*, 347 (25), 1999-2009 (2002).

Van 'T Veer et al., "Gene expression profiling predicts clinical outcome of breast cancer," *Nature*, 415 (6871), 530-536 (2002).

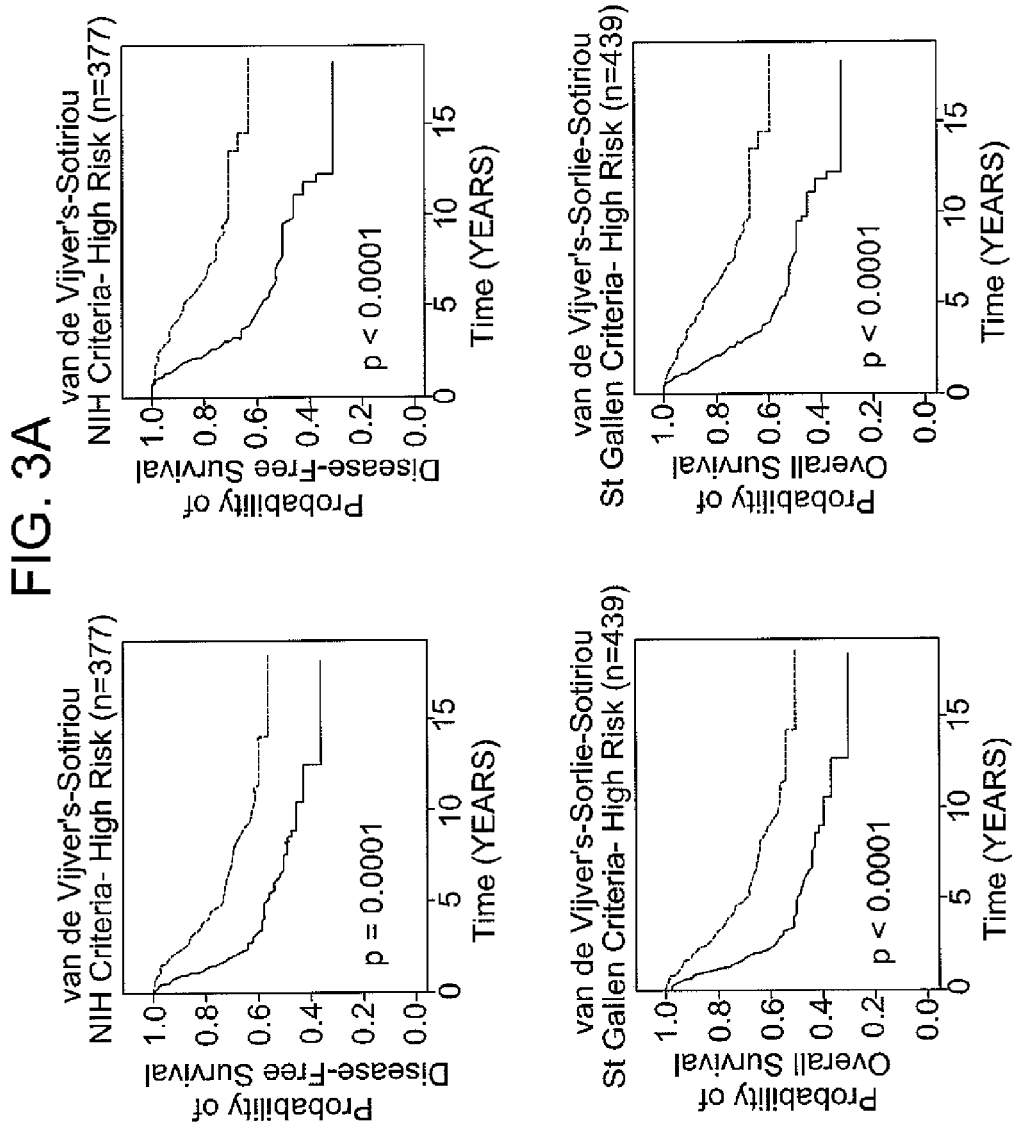

GENE EXPRESSION SIGNATURE OF GENOMIC INSTABILITY IN BREAST CANCER

CROSS-REFERENCE TO RELATED APPLICATIONS

This patent application is a U.S. National Phase of International Patent Application No. PCT/US09/56931, filed Sep. 15, 2009, which claims the benefit of U.S. Provisional Patent Application No. 61/097,101, filed Sep. 15, 2008, which applications are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 86,018 Byte ASCII (Text) file named "707851.2-ST25.TXT" created on Apr. 12, 2011.

BACKGROUND OF THE INVENTION

Breast cancers are among the most frequently occurring tumors in women worldwide, and the clinical course and disease free survival times for patients with breast cancers are extremely heterogeneous. Accordingly, intensive efforts have been made over the past decades to develop biological markers that allow for precise disease staging and prognostication. Such markers include tumor size, grade and stage, lymph node and hormone receptor status, expression of growth factor receptors, DNA content, S-phase fraction and proliferative activity, and, more recently, specific gene expression signatures that suggest a poor prognosis. Genomic instability also is a common trait of breast cancers and impacts on prognosis. Genomic instability is the tendency of the cells of a tissue to exhibit diversity in the amount of nuclear DNA present, principally due to chromosomal rearrangement and duplication. This parameter of cancer tissue typically is assessed on the basis of cytometric measurements of nuclear DNA content, and is not directly accounted for in most established prognostic tests. Thus, there remains a need for new methods and compositions that can be used to prognosticate the clinical course and survival times of breast cancer patients, especially those that account for genomic instability.

BRIEF SUMMARY OF THE INVENTION

The invention provides a method of assessing genomic instability in breast cancer tissue comprising (a) measuring the expression level of (i) CDKN2A, SCYA18, STK15, NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21, in breast cancer tissue to provide an expression profile of the breast cancer tissue, and (b) comparing the expression profile of the breast cancer tissue to a control.

In a related aspect, the invention provides a method of assessing genomic instability in breast cancer tissue comprising (a) measuring the expression level of (i) NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21 in breast cancer tissue relative to the expression of (i) and (ii) in genomically-stable breast tissue, and (b) measuring the expression level of CDKN2A, SCYA18, and STK15 in the breast cancer tissue relative to the expression of the same genes in genomically-stable breast tissue, wherein genomic instability is indicated if (i) and (ii) are under-expressed in the breast cancer tissue as compared to the expression of the same genes in genomically-stable breast tissue, and CDKN2A, SCYA18, and STK15 are over-expressed in the breast cancer tissue as compared to the expression of the same genes in genomically-stable breast tissue.

The invention also provides a method of screening for a compound that alters genomic instability in breast tissue comprising (a) contacting one or more test compounds with a sample of breast tissue, and (b) comparing the expression level of (i) CDKN2A, SCYA18, STK15, NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21, in the sample of breast tissue after contact with the one or more test compounds with the expression level of (i) and (ii) in breast tissue in the absence of the one or more test compounds, wherein a change in the expression level of (i) and (ii) after contact with the one or more test compounds as compared to the expression level of (i) and (ii) in the absence of the one or more test compounds indicates that the one or more test compounds alter genomic instability in breast tissue.

The invention further provides an array comprising (a) a substrate and (b) twelve or more different addressable elements that each comprise at least one polynucleotide that binds to an mRNA transcript of CDKN2A, SCYA18, STK15, NXF1, cDNA Dkfzp762M127, p28, KIAA0882, MYB, Human clone 23948, RERG, HNF3A, and ACADSB or a nucleic acid sequence comprising about 90% or greater sequence identity to SEQ ID NO: 21, or cDNA synthesized therefrom, wherein the array comprises 1000 or fewer different addressable elements.

BRIEF DESCRIPTION OF THE SEVERAL VIEWS OF THE DRAWING(S)

FIG. 1 presents graphs showing the probability of metastasis-free survival, relapse-free survival, or overall survival plotted against time for donors of samples that were classified as genomically stable (dotted line) and genomically unstable (solid line) according to a 12-gene signature of genomic instability in three different patient cohorts.

Figure 2:
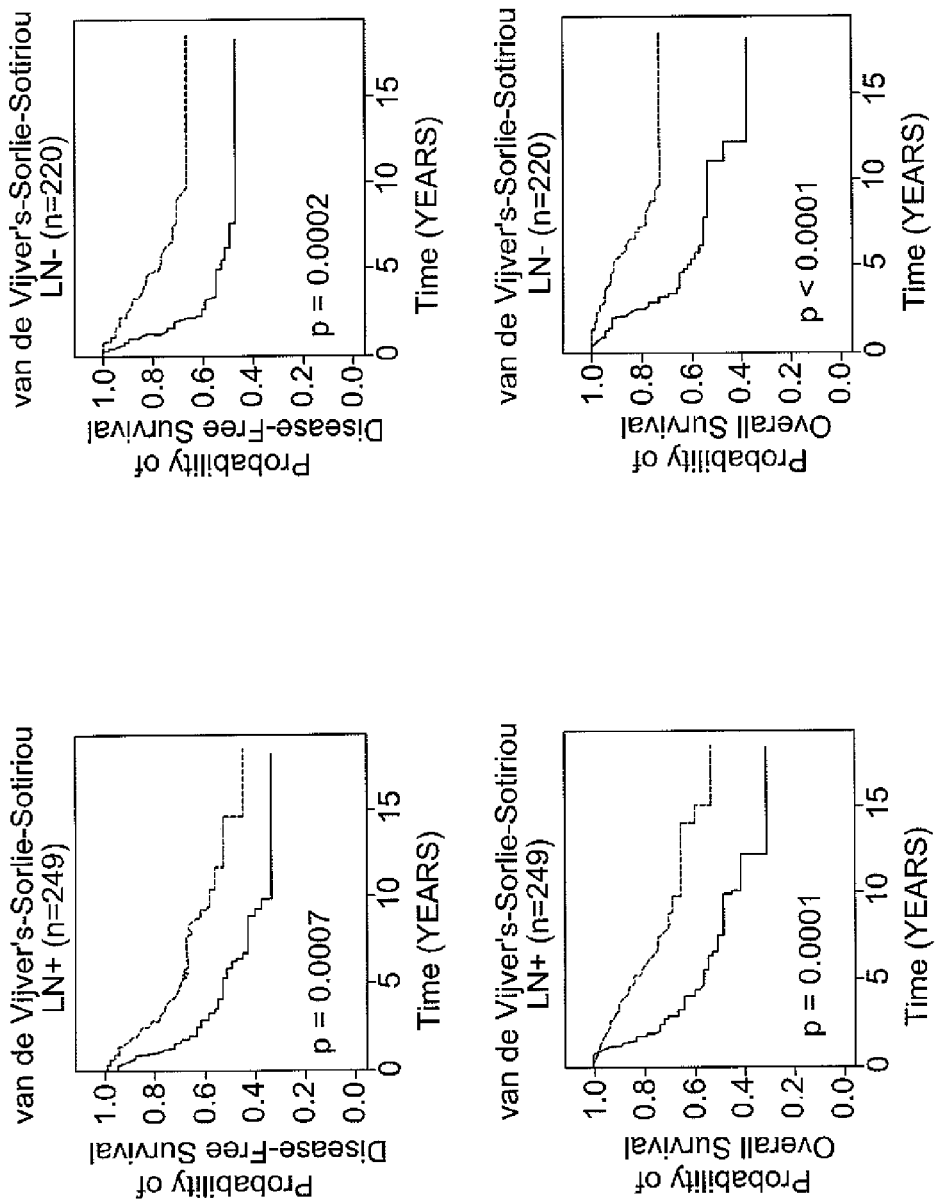

FIG. 2 presents graphs showing the probability of disease-free survival or overall survival plotted against time for donors of samples that were classified as genomically stable (dotted line) and genomically unstable (solid line) according to a 12-gene signature of genomic instability in three combined patient cohorts divided into two groups by lymph node status: lymph node positive (LN+) and lymph node negative (LN−) status.

FIG. 3A presents graphs showing the probability of metastasis-free survival or overall survival plotted against time for donors of samples that were classified as genomically stable (dotted line) and genomically unstable (solid line) according to a 12-gene signature of genomic instability in patients that meet the NIH consensus criteria or St. Gallen's criteria of low-risk.

Figure 3B:
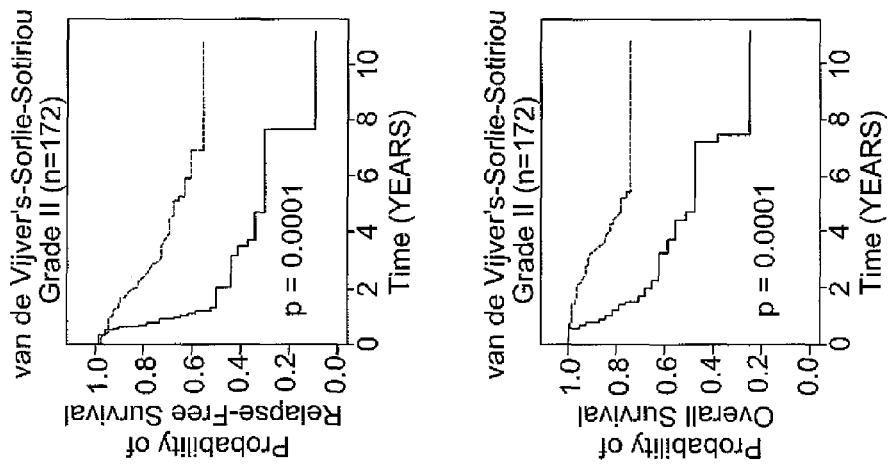

FIG. 3B presents graphs showing the probability of relapse-free survival or overall survival plotted against time for donors of samples that were classified as genomically stable (dotted line) and genomically unstable (solid line) according to a 12-gene signature of genomic instability for patients with grade II tumors.

DETAILED DESCRIPTION OF THE INVENTION

The invention provides methods that are useful for evaluating genomic instability in breast cancer tissue according to the expression of twelve genes: CDKN2A, SCYA18, STK15, NXF1, cDNA Dkfzp762M127, p28, KIAA0882, MYB, Human clone 23948, RERG, HNF3A, and ACADSB or a nucleic acid sequence comprising about 90% or greater sequence identity to SEQ ID NO: 21. As used herein, the expression of a "gene" is used to refer to the expression of a nucleic acid (e.g., mRNA) or protein product encoded thereby.

Cyclin-dependent kinase inhibitor 2A (CDKN2A) is referenced in the NCBI database by GeneID 1029 (UniGeneID Hs.512599), and is also known as ARF; MLM; p14; p16; p19; CMM2; INK4; MTS1; TP16; CDK4I; CDKN2; INK4a; p14ARF; p16INK4; and p16INK4a. The sequence of the mRNA transcripts of CDKN2A are referenced in the NCBI database under NC_000009.10 (GI: 89161216) as NM_058195.2 (GI: 47132605) (SEQ ID NO: 1), NM_058197.3 (GI: 98985803) (SEQ ID NO: 2), and NM_000077.3 (GI: 47132606) (SEQ ID NO: 3).

Small inducible subfamily A18 (SCYA18) is referenced in the NCBI database by GeneID 6362 (UniGeneID Hs.143961), and is also known as CCL18, CKb7; PARC; AMAC1; DCCK1; MIP-4; AMAC-1; and DC-CK1. The sequence of the mRNA transcript of SCYA18 is referenced in the NCBI database under NC_000017.9 (gi: 51511734) as NM_002988.2 (GI:22547150) (SEQ ID NO: 4).

Serine/threonine kinase 15 (STK15) is referenced in the NCBI database by GeneID 6790 (UniGeneID Hs.250822), and is also known as Aurora kinase A (AURKA); AIK; ARK1; AURA; BTAK; STK6; STK7; AURORA2; and MGC34538. The sequence of the mRNA transcripts of STK15 are referenced in the NCBI database under NC_000020.9 (GI: 51511747) as NM_003600.2 (gi: 38327561) (SEQ ID NO: 5), NM_198433.1 (gi: 38327563) (SEQ ID NO: 6), NM198435.1 (gi: 38327567) (SEQ ID NO: 7), NM_198434.1 (gi: 38327565) (SEQ ID NO: 8), NM_198437.1 (gi: 38327571) (SEQ ID NO: 9), and NM_198436.1 (gi: 38327569) (SEQ ID NO: 10).

Nuclear RNA export factor 1 (NXF1) is referenced in the NCBI database by GeneID 10482 (UniGeneID Hs.523739), and is also known as TAP; MEX67; and DKFZp667O0311. The sequence of the mRNA transcripts of NXF1 are referenced in the NCBI database under NC_000011.8 (gi: 51511727) as NM_001081491.1 (gi: 125625323) (SEQ ID NO: 11) and NM_006362.4 (gi: 125625327) (SEQ ID NO: 12).

Homo sapiens mRNA cDNA Dkfzp762M127 (hereinafter "cDNA Dkfzp762M127") is referenced in the NCBI database by Accession Number AL157484.1 (GI: 7018527) (UnigeneID Hs.568928). The sequence of the mRNA transcript associated with cDNA Dkfzp762M127 also is provided herein as SEQ ID NO: 13.

p28 is referenced in the NCBI database by GeneID 7802 (UniGeneID Hs.406050), and is also known as dynein, axonemal, light intermediate chain 1 (DNALI1); hp28; and dj423B22.5. The sequence of the mRNA transcript of p28 is referenced in the NCBI database as NM_003462.3 (GI: 37595559) and provided herein as SEQ ID NO: 14.

KIAA0882 is referenced in the NCBI database by GeneID 23158 (UniGeneID Hs.480819), and is also known as TBC1 domain family, member 9 (TBC1D9) or MDR1. The sequence of the mRNA transcript of KIAA0882 is referenced in the NCBI database as NM_015130.2 (GI: 139394667) and provided herein as SEQ ID NO: 15.

v-Myb myeloblastosis viral oncogene homolog (avian) (MYB) is referenced in the NCBI database by GeneID 4602, and is also known as efg; Cmyb; c-myb; and c-myb_CDS. The sequence of the mRNA transcript of MYB is referenced in the NCBI database as NM_005375.2 (GI: 46361979) and provided herein as SEQ ID NO: 16.

Human clone 23948 mRNA sequence (hereinafter "human clone 23948) is referenced in the NCBI database by Accession Number U79293.1 (GI: 1710274) (UniGeneID Hs.655686) and provided herein as SEQ ID NO: 17.

RAS-like, estrogen-regulated, growth inhibitor (RERG) is referenced in the NCBI database by GeneID 85004 (UniGeneID Hs.199487), and is also known as MGC15754. The sequence of the mRNA transcript of RERG is referenced in the NCBI database as NM_032918.1 (GI: 14249703) and provided herein as SEQ ID NO: 18.

Hepatocyte nuclear factor 3 alpha (HNF3A) is referenced in the NCBI database by GeneID 3169 (UniGeneID Hs.163484), and is also known as forkhead box A1 (FOXA1); TCF3A; and MGC33105. The sequence of the mRNA transcript of HNF3A is referenced in the NCBI database as NM_004496.2 (GI: 24497500) and provided herein as SEQ ID NO: 19.

Acyl-Coenzyme A dehydrogenase, short/branched chain (ACADSB) is referenced in the NCBI database by GeneID 36 (UniGeneID Hs.81934), and is also known as ACAD7, SBCAD, and 2-MEBCAD. The sequence of the mRNA transcript of ACADSB is NM_001609.3 (GI:96361828) (SEQ ID NO: 20).

The nucleic acid comprising about 90% or greater sequence identity to SEQ ID NO: 21 includes, for instance, a nucleic acid comprising about 92% or greater, 95% or greater, 96% or greater, 97% or greater, 98% or greater, or even 99% or greater sequence identity to SEQ ID NO: 21, as well as a nucleic acid that comprises SEQ ID NO: 21. Such a nucleic acid includes, for instance, a nucleic acid referenced in the art as Incyte EST (Clone ID 88935).

Measuring or detecting the expression of any of the foregoing genes or nucleic acids comprises measuring or detecting any nucleic acid transcript (e.g., mRNA) or protein product thereof. Where a gene is associated with more than one mRNA transcript, the expression of the gene can be measured or detected by measuring or detecting any one or more of the mRNA transcripts of the gene, or all of the mRNA transcripts). In one embodiment, the invention provides a method of assessing genomic instability in breast cancer tissue comprising (a) measuring the expression level (i) CDKN2A, SCYA18, STK15, NXF1, cDNA Dkfzp762M127, p28, KIAA0882, MYB, Human clone 23948, RERG, HNF3A, and (ii) ACADSB or a nucleic acid comprising about 90% or greater sequence identity to SEQ ID NO: 21, in breast cancer tissue to provide an expression profile of the breast cancer tissue, and (b) comparing the expression profile of the breast cancer tissue to a control. The term "assess" as used herein means to test for, or determine the presence or absence of, a condition. Thus, "assessing" encompasses, but is not limited to, detecting or measuring (e.g., quantifying) the gene expression level by any method. Typically, assessing genomic instability in breast cancer tissue comprises assessing genomic instability in a sample of the breast cancer tissue taken from a subject.

Typically, the gene expression can be detected or measured on the basis of mRNA or cDNA levels, although protein levels also can be used when appropriate. Suitable methods of detecting or measuring mRNA or cDNA levels include, for example, Northern Blotting, reverse-transcription PCR (RT-PCR), real-time RT-PCR, and microarray analysis. Such methods are described in Sambrook et al., *Molecular Cloning: A Laboratory Manual*, $2^{nd}$ Ed., Cold Spring Harbor Press, Cold Spring Harbor, N.Y., 1989. Preferably, microarray analysis or a PCR-based method is used. In this respect, the measuring the expression of the foregoing nucleic acids in breast cancer tissue can comprise, for instance, contacting a sample of breast cancer tissue with probes specific to the nucleic acids, or with primers designed to amplify a portion of the nucleic acids, and detecting binding of the probe to the nucleic acid or amplification of the nucleic acid, respectively. Detailed protocols for designed PCR probes are known in the art. Similarly, detailed protocols for preparing and using microarrays to analyze gene expression are known in the art and described herein.

The control can be any suitable reference that allows evaluation of the expression level of the genes in the breast cancer tissue as compared to the expression of the same genes in an established genomically stable or genomically unstable sample, or a pool of such samples. Thus, for instance, the control can be a genomically stable or genomically unstable sample that is analyzed simultaneously or sequentially with the test sample, or the control can be the average expression level of the genes of interest, as described above, in a pool of breast tissue samples known to be genomically stable or genetically unstable. Thus, the control can embodied, for example, in a pre-prepared microarray used as a standard or reference, or in data that reflects the expression profile of relevant genes in a sample or pool of genomically stable or genetically unstable samples, such as might be part of an electronic database or computer program.

The genomic instability of samples can be assessed for the purposes of establishing a control on the traditional basis of nuclear DNA content using routine methods (e.g., image cytometry) and tissues classified as genomically stable or genomically unstable according to known indices (e.g., Kronenwett et al., *Cancer Res*, 64(3), 904-9 (2004); Kronenwett et al., *Cancer Epidemiol Biomarkers Prev*, 15(9), 1630-5 (2006)). For instance, breast cancer tissue can be considered diploid and genomically stable (dGS) if it exhibits a major peak at 2c and a low stemline scatter index (SSI<8.8); aneuploid, yet stable (aGS), as judged by a dominant aneuploid peak, yet a SSI below or equal 8.8; and aneuploid with substantial variability in the nuclear DNA content, and, hence, genomically unstable if exhibiting a SSI above 8.8 (aGU). Such methods are further illustrated by the examples provided herein.

The expression profile of the breast cancer tissue can be compared to the control by any suitable technique. Typically, comparing the expression profile of the breast cancer tissue to a control comprises calculating a correlation coefficient of the expression profile of the breast cancer tissue with respect to the control. Any statistical method can be used to calculate the correlation coefficient, such as using Pearson's correlation method (see Strickert et al., *BMC Bioinformatics*, 8, (2007)). Pearson's correlation coefficient describes the linear dependency of vectors x and w by:

$$R(x, w) = \frac{\sum_{i=1}^{d}(xi - \mu x) \cdot (wi - \mu w)}{\sqrt{\sum_{i=1}^{d}(xi - \mu x)^2} \cdot \sqrt{\sum_{i=1}^{d}(wi - \mu w)^2}}$$

where $\mu x$ and $\mu w$ are the respective means of the vectors x and w. The equation is standardized by the product of the standard deviations of the vectors. Pearson's correlation coefficient is method commonly used for identifying gene expression patterns associated with traits of biological phenotypes (see Strickert et al., *BMC Bioinformatics*, 8, (2007); Kraft et al., *Am J Hum Genet*, 72(5), 1323-30 (2003)). Based on the similarity of the expression profile in the breast cancer tissue to the control, genomic instability of the sample can be assessed. For instance, when the control is the average expression profile of the genes in a pool of known genomically stable breast tissue samples, genomic instability is inversely proportional to the correlation coefficient, such that an increasingly large correlation coefficient indicates a greater degree of genomic instability and, vice versa, a decreasing correlation coefficient indicates a lesser degree of genomic instability. The converse is true if the control is the average expression profile of the genes in a pool of known genomically unstable breast tissue samples. In that case, genomic instability is in direct proportion to the correlation of the expression profile of the breast cancer tissue to the control, such that an increasing large correlation coefficient indicates a greater degree of genomic instability and a decreasing correlation coefficient indicates a lesser degree of genomic instability.

The assessment of genomic instability can be based on a pre-determined metric or "cut-off." By way of illustration, when the control is the expression profile of genes in a pool of known genomically stable breast tissue, genomic instability can be indicated by a Pearson's correlation coefficient of about −0.5 (P=0.05) or less, such as about −0.6 (P=0.02) or less, or even about −0.7 (P=0.006) or less. Similarly, when the control is the expression profile of genes in a pool of known genomically unstable breast tissue, genomic instability can be indicated by a Pearson's correlation coefficient of about 0.5 (P=0.05) or greater, such as about 0.6 (P=0.02) or greater, or even about 0.7 (P=0.006) or greater. The statistical significance can be assessed using the test for the significance of the Pearson product-moment correlation coefficient (see Moore, D. *Basic Practice of Statistics*. 4 ed. WH Freeman Company (2006)).

The assessment of genomic stability also can be relative, as might be the case when both a positive and negative control is used. For example, the method can comprise comparing the expression profile of the breast cancer tissue to a first and second control by calculating a correlation coefficient of the expression profile of the breast cancer tissue with respect to each of the first and second controls (i.e., to provide a first and second correlation coefficient, respectively), wherein the first control is the average expression profile of the genes of (a) in a pool of known genomically stable breast tissue samples and the second control is the average expression profile of the genes of (a) in a pool of known genomically unstable breast tissue samples. In this case, it is possible to assess genomic instability of the breast cancer tissue sample as compared to the first and second controls by comparing the first and second correlation coefficients. According to this embodiment of the method, genomic instability is indicated if the correlation coefficient of the expression profile of the breast cancer tissue calculated with respect to the second control (the genomically unstable control) is greater than the correlation coefficient of the expression profile of the breast cancer calculated with respect to the first control (the genomically stable control).

Of course, the methods described herein are not dependent upon any one statistical technique (e.g., Pearson's Correlation), and other suitable techniques for quantifying the correlation or similarity between the expression profile of two or more different samples are known (e.g., Spearman's rank correlation coefficient (Myers et al., *Research Design and Statistical Analysis*. 2 ed. Lawrence Erlbaum (2003)), Kendall tau rank correlation coefficient (Abdi, H. "Kendall rank correlation" In: Salkind, N J, editor. *Encyclopedia of Measurement and Statistics*. Thousand Oaks, Calif.: Sage (2007)), and rearrangement inequality (Wayne, A. *Scripta Mathematica*, 12(2), 164-9 (1946)). Thus, in any of the foregoing described methods and embodiments the "correlation coefficient" is used generically to refer to any appropriate distance metric. Similarly, the foregoing ranges expressed in terms of Pearson's correlation are only for the purposes of illustration, and the equivalent of the foregoing ranges using a different statistical technique also can be used. Computer algorithms are known and embodied in commercially available software that facilitate the comparison, and analyze the relatedness, between gene expression profiles any of which can be used in conjunction with the methods of the invention.

In a related aspect, the invention provides a method of assessing genomic instability in breast cancer tissue comprising (a) measuring the expression level of (i) NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21 in the breast cancer tissue relative to the expression of the same genes in genomically-stable breast tissue, and (b) measuring the expression level of CDKN2A, SCYA18, and STK15 in the breast cancer tissue relative to the expression of the same genes in genomically-stable breast tissue, wherein genomic instability is indicated if (i) and (ii) are under-expressed in the breast cancer tissue as compared to the expression of the same genes in genomically-stable breast tissue, and CDKN2A, SCYA18, and STK15 are over-expressed in the breast cancer tissue as compared to the expression of the same genes in genomically-stable breast tissue.

Over-expression and under-expression of the genes can be determined by any suitable method, such as by comparing the expression of the genes in a test sample with a control (e.g., a positive or negative control), or by using a predetermined "cut-off" of absolute expression. A control can be provided as previously discussed. Regardless of the method used, over-expression and under-expression can be defined as any level of expression greater than or less than, respectively, the level of expression of the same genes in genomically stable breast cancer tissue. By way of further illustration, overexpression can be defined as expression that is about 1.2-fold, 1.5-fold, 2-fold, 5-fold, 10-fold, 20-fold, 50-fold, 100-fold higher or even greater expression as compared to genomically stable breast cancer tissue, and under-expression can similarly be defined as expression that is about 90% or less, 75% or less, 50% or less, 25% or less, 10% or less, 5% or less, or even 1% or less of the expression in genomically stable breast cancer tissue.

The method of assessing genomic instability in breast cancer tissue can be used for any purpose, but is believed to be especially useful in prognosticating the clinical course of breast cancer, wherein genomic instability is indicative of a poor prognosis (e.g., increased likelihood of relapse and/or shorter predicted survival time). Furthermore, the relative degree of genomic instability is believed to relate to the clinical prognosis, such that a closer correlation between the expression profile of the sample and the expression profile of a genomically unstable reference or control expression pattern (e.g., the average expression of a pool of genomically unstable samples) is indicative of a poorer prognosis. All other aspects of the method are as previously discussed.

The methods of the invention also can be used for other purposes, such as to monitor the progression or regression of disease, or assess the effectiveness of treatment, in a patient. In the context of such uses, the method can be applied to different samples (e.g., a first and second sample) taken from the same patient at different points in time and the results compared, wherein a change in genomic instability can be used to reach a determination as to whether the disease has progressed or regressed or a given treatment has been effective. More particularly, increasing genomic instability between a sample taken at an earlier point in time (first sample) and a sample taken at a later point in time (second sample) suggests progression of disease or lack of effectiveness of a treatment, and a decrease in genomic stability between a sample taken at an earlier point in time and a sample taken at a later point in time suggests a regression of the disease or effectiveness of a treatment.

The methods described herein also can be used to screen for compounds that alter genomic stability. Candidate compounds may be screened for potential effect on genomic stability by detecting changes in genomic stability on the basis of the expression of the gene signature described herein. For instance, such a method of screening for a compound that alters genomic instability in breast tissue can comprise (a) contacting one or more test compounds with a sample of breast tissue, and (b) comparing (i) the expression level of CDKN2A, SCYA18, STK15, NXF1, cDNA Dkfzp762M127, p28, KIAA0882, MYB, Human clone 23948, RERG, HNF3A, and ACADSB or a nucleic acid sequence comprising about 90% or greater sequence identity to SEQ ID NO: 21 in the sample of breast tissue after contact with the one or more test compounds with (ii) the expression level of the same nucleic acids in breast tissue in the absence of the one or more test compounds. A change in the expression level of one or more of the genes, such as five or more of the genes or even all of twelve of the genes, after contact with the one or more test compounds as compared to the expression level of the genes in the absence of (e.g., before contact with) the one or more test compounds indicates that the one or more test compounds alters genomic instability in breast tissue.

In a related aspect, the method of screening a compound can comprise (a) measuring the expression level of (i) CDKN2A, SCYA18, STK15, NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21 in a sample of breast tissue to provide an expression profile, (b) calculating the correlation coefficient of the expression profile with respect to a control, (c) contacting the breast cancer tissue with one or more test compounds, and (d) detecting a change in the correlation coefficient after contact with the one or more test compounds as compared to the correlation coefficient of the breast tissue in the absence of (e.g., before contact with) the one or more test compounds, wherein a change in the correlation coefficient indicates that the one or more test compounds alters genomic stability. Detecting a change in the correlation coefficient can further comprise measuring the expression level of the genes of step (a) in the breast tissue after contact with the one or more test compounds to arrive at a second correlation coefficient, and comparing the correlation coefficient of step (b) with the second correlation coefficient. As discussed with other methods of the invention, the method of screening for compounds does not depend upon the application of any particular statistical technique. Thus, any technique for arriving at a correlation coefficient or other distance metric that provides an appropriate quantifiable basis for comparing gene expression profiles can be used. Such techniques are identified herein in connection with the other methods of the invention. Similarly, all other aspects of the method of screening are as described with respect to the other methods of the invention.

The invention also provides an array that can be used to assess genomic instability in accordance with the methods of the invention, or for any other purpose. The array comprises (a) a substrate and (b) twelve or more different addressable elements that each comprise at least one polynucleotide that binds to an mRNA transcript of CDKN2A, SCYA18, STK15, NXF1, cDNA Dkfzp762M127, p28, KIAA0882, MYB, Human clone 23948, RERG, HNF3A, and ACADSB or a nucleic acid sequence comprising about 90% or greater sequence identity to SEQ ID NO: 21, or cDNA synthesized therefrom. As used herein, the term "addressable element" means an element that is attached to the substrate at a predetermined position and specifically binds a known target molecule, such that when target-binding is detected (e.g., by fluorescent labeling), information regarding the identity of the bound molecule is provided on the basis of the location of the element on the substrate. Addressable elements are "different" for the purposes of the present invention if they do not bind to the same target molecule. The addressable element comprises one or more polynucleotides (i.e., probes) specific for an mRNA transcript of a given gene, or a cDNA synthesized from the mRNA transcript. The addressable element can comprise more than one copy of a polynucleotide, can comprise more than one different polynucleotide, provided that all of the polynucleotides bind the same target molecule. Where a gene is known to express more than one mRNA transcript, the addressable element for the gene can comprise different probes for different transcripts, or probes designed to detect a nucleic acid sequence common to two or more (or all) of the transcripts. Alternatively, the array can comprise an addressable element for the different transcripts. The addressable element also can comprise a detectable label, suitable examples of which are well known in the art.

The array can comprise addressable elements that bind to mRNA or cDNA other than that of CDKN2A, SCYA18, STK15, NXF1, cDNA Dkfzp762M127, p28, KIAA0882, MYB, Human clone 23948, RERG, HNF3A, and ACADSB or a nucleic acid sequence comprising about 90% or greater sequence identity to SEQ ID NO: 21. It will be appreciated, however, that an array capable of detecting a vast number of targets (e.g., mRNA or polypeptide targets), such as arrays designed for comprehensive expression profiling of a cell line, chromosome, genome, or the like, are not economical or convenient for use as a diagnostic tool or screen for any particular condition like genomic instability. Thus, to facilitate the convenient use of the array as a diagnostic tool or screen, for example, in conjunction with the methods described herein, the array preferably comprises a limited number of addressable elements. In this regard, the array desirably comprises no more than about 1000 or fewer different addressable elements, more preferably no more than about 500 or fewer different addressable elements, or even no more than about 100 or fewer different addressable elements, such as about 75 or fewer different addressable elements, or even about 50 or fewer different addressable elements. Of course, even smaller arrays can comprise about 25 or fewer different addressable elements, such as about 15 or fewer different addressable elements. The array can be limited to 12 different addressable elements without interfering with its functionality.

The substrate can be any rigid or semi-rigid support to which polynucleotides can be covalently or non-covalently attached. Suitable substrates include membranes, filters, chips, slides, wafers, fibers, beads, gels, capillaries, plates, polymers, microparticles, and the like. Materials that are suitable for substrates include, for example, nylon, glass, ceramic, plastic, silica, aluminosilicates, borosilicates, metal oxides such as alumina and nickel oxide, various clays, nitrocellulose, and the like.

The polynucleotides of the addressable elements (hereinafter referred to as "probes") can be attached to the substrate in a pre-determined 1- or 2-dimensional arrangement, such that the pattern of hybridization or binding to a probe is easily correlated with the expression of a particular gene. Because the probes are located at specified locations on the substrate (i.e., the elements are "addressable"), the hybridization or binding patterns and intensities create a unique expression profile, which can be interpreted in terms of expression levels of particular genes and can be correlated with genomic instability in accordance with the methods described herein.

Polynucleotide and polypeptide probes can be generated by any suitable method known in the art (see, e.g., Sambrook et al., *Molecular Cloning: A Laboratory Manual, 2$^{nd}$ Ed.*, Cold Spring Harbor Press, Cold Spring Harbor, N.Y., (1989)). For example, polynucleotide probes that specifically bind to the mRNA transcripts of the genes described herein (or cDNA synthesized therefrom) can be created using the nucleic acid sequences of the mRNA or cDNA targets themselves (e.g., SEQ ID NOs: 1-12 or fragments thereof) by routine techniques (e.g., PCR or synthesis). As used herein, the term "fragment" means a contiguous part or portion of a polynucleotide sequence comprising about 10 or more nucleotides, preferably about 15 or more nucleotides, more preferably about 20 or more nucleotides (e.g., about 30 or more or even about 50 or more nucleotides). By way of further illustration, a polynucleotide probe that binds to an mRNA transcript of CDKN2A (or cDNA corresponding thereto) can be provided by a polynucleotide comprising a nucleic acid sequence that is complementary to the mRNA transcript (e.g., SEQ ID NO: 1) or a fragment thereof, or sufficiently complementary to SEQ ID NO: 1 or fragment thereof that it selectively binds to SEQ ID NO: 1. The same is true with respect to the other genes described herein. The exact nature of the polynucleotide probe is not critical to the invention; any probe that will selectively bind the mRNA or cDNA target can be used. Typically, the polynucleotide probes will comprise 10 or more nucleic acids (e.g., 20 or more, 50 or more, or 100 or more nucleic acids). In order to confer sufficient specificity, the probe will have a sequence identity to a complement of the target sequence (e.g., SEQ ID NOs: 1-41 or corresponding fragment thereof) of about 90% or more, preferably about 95% or more (e.g., about 98% or more or about 99% or more) as determined, for example, using the well-known Basic Local Alignment Search Tool (BLAST) algorithm (available through the National Center for Biotechnology Information (NCBI), Bethesda, Md.).

The array can comprise other elements common to polynucleotide arrays. For instance, the array also can include one or more elements that serve as a control, standard, or reference molecule, such as a housekeeping gene or portion thereof (e.g., PBGD or GAPDH), to assist in the normalization of expression levels or the determination of nucleic acid quality and binding characteristics, reagent quality and effectiveness, hybridization success, analysis thresholds and success, etc. These other common aspects of the arrays or the addressable elements, as well as methods for constructing and using arrays, including generating, labeling, and attaching suitable probes to the substrate, consistent with the invention are well-known in the art. Other aspects of the array are as previously described herein with respect to the methods of the invention.

The following examples further illustrate the invention but, of course, should not be construed as in any way limiting its scope.

EXAMPLES

The below techniques and protocols were used in the following examples, except as otherwise noted:

Immunohistochemistry:

All slides were deparaffinized with xylene, rehydrated and microwaved at 500 W for 2×5 min in 10 mM citrate buffer, pH 6.0. Intrinsic peroxidase activity was blocked with 3% hydrogen peroxide in methanol, followed by incubation with horse serum (1:20 dilution) in 0.1M PBS, pH 6.0. The levels of protein expression were revealed by overnight incubation with an antibody against cyclin A (Dilution 1:100, Novocastra, Newcastle upon Tyne, UK). The antibody was diluted in 1% (weight/volume) bovine serum albumin and visualized by standard avidin biotin-peroxidase complex technique (Vector Laboratories, Burlingame, Calif.). The cyclin A immunoreactivity was confined to the cell nuclei. In each specimen, the cyclin A labeling index (i.e., the percentage of stained tumor cells) was calculated.

Microarray Analysis:

Total RNA was extracted using TRIzol (Invitrogen) followed by Qiagen RNeasy column purification (Qiagen, Valencia, Calif.). Sample RNA and universal human reference RNA (Stratagene, La Jolla, Calif.) were then amplified for one round using RiboAmp RNA Amplification Kit (Arcturus, Mountain View, Calif.). All amplified RNA samples were hybridized against amplified reference RNA using a slightly modified protocol described in Hegde et al., *BioTechniques*, 29(3), 548-50, 52-4, 56 passim (2000). 3 μg of amplified RNA was reverse transcribed using random primers and converted into cDNA using reverse transcriptase. After incorporation of aminoallyl-conjugated nucleotides, the RNA was indirectly labelled with Cy3 (tumor RNA) and Cy5 (reference RNA, Amersham, Piscataway, N.J.). Each sample was hybridized against the reference RNA in a humid chamber (Arraylt™ Hybridization Cassette, TeleChem Intl., Sunnyvale, Calif.) for 16 hours at 42° C., washed, and scanned by the Axon GenePix 4000B Scanner (Axon Instruments, Union City, Calif.). In order to account for potential amplification bias, total RNA was hybridized following the same protocol for 11 samples (20 μg each). Customized arrays obtained from the National Cancer Institute's microarray core facility were used. Arrays were used from one print batch and composed of 9,128 cDNAs denatured and immobilized on a poly-L-lysine-coated glass surface. The gene annotation file (GAL file) used (Hs-UniGEM2-v2px-32Bx18Cx18R.gal) can be found at National Cancer Institute (NCI) "mAdb" Gateway (National Cancer Institute, Bethesda, Md.). GenePix software version 4.0.1.17 was used to apply the GAL file through an interactive gridding process (see Korn et al., *BioTechniques*, 36(6), 960-7 (2004)).

Arrays that did not pass quality assessment criteria were discarded, leaving a total of 14 diploid, genomically stable (dGS) samples, 14 aneuploid, genomically stable (aGS), and 16 aneuploid, genomically unstable (aGU) samples that could be processed for further analysis. All values that did not meet the quality control criteria were treated as missing values. Intensity ratios were calculated using the background corrected median intensities that were normalized with the locally weighted scatter plot smoother (LOWESS) algorithm for each print-tip group. The fraction of data points used in the local regression (f) was 0.1 and other parameters were adjusted as suggested by Cleveland et al., *J Am Stat Assoc*, 74(368), 829-36 (1979). The value of f was determined using two self versus self experiments. All within-slide normalized ratios were log-transformed (natural base). A total of 7,657 genes were identified that did not show any missing values across all samples. Out of those 7,657 genes, differentially expressed genes were identified with pair-wise analysis: dGS against aGS, dGA against aGU, and aGS against aGU samples.

In order to produce a robust gene list, two methods were applied and only genes identified by both tests were used. First, the Wilcoxon rank-sum test was used with a permutation test so that if the p-value between the two groups was below 0.05, the values were randomly labeled into these two groups and the p-value was computed and repeated 10,000 times. All cases where the p-value using permuted labels was under 0.05 were summed and divided by the total number of permutations (10,000). This α-value denotes the probability that a gene had a smaller or equal significance by random permutation than the original significance (see Hyman et al., *Cancer Res*, 62(21), 6240-5 (2002)). Genes having α-value below 0.05 were considered to be differentially expressed. Second, a step-wise gene selection procedure was used (see Xiong et al., *Mol Genet Metab*, 73(3), 239-47 (2001); and Kauraniemi et al., *Oncogene*, 23(4), 1010-3 (2004)). The basic idea is to add genes one by one to a set of genes that discriminates two classes the best using Fisher's linear discriminant. The step-wise procedure was stopped if the weight (that marks the separation of the ratios between two classes) was less than 0.001. Finally, an intersection of the genes that were statistically significant using the Wilcoxon test was selected, and also identified with the step-wise gene selection procedure.

Biological Pathway Analysis:

Ingenuity Pathways Analysis (IPA) software (Ingenuity, Mountain View, Calif.) was used to assess the involvement of significantly differentially expressed genes in known pathways and networks. Differentially expressed genes as identified above were uploaded into the program and defined as focus genes if they were also part of the Pubmed-based IPA knowledge database. IPA was then used to determine groups of genes—involving focus genes and those known to interact with them—that together constitute networks. Such networks indicate how the genes of interest may influence each other above and beyond canonical pathways that are described in the Kyoto Encyclopedia of Genes and Genomes (KEGG). The IPA generated networks are listed in a certain order, with the top networks having a lower likelihood that the generation of the networks was serendipitous.

Example 1

The following example demonstrates the correlation of gene expression with genomic instability.

Tumor samples were collected from 48 patients diagnosed with breast cancer. Clinical material was collected from surgically removed tumors, diagnosed on H&E-stained tissue sections, and graded according to Elston et al., *Histopathology*, 19(5), 403-10 (1991). The clinical data are summarized in Table 1. After surgery, clinical tissue was used for touch preparation slides for quantitative measurement of the nuclear DNA content. The tissue samples were then snap frozen until further processing with TRIzol reagent (Invitrogen, Carlsbad, Calif.) for DNA and RNA extraction. In addition, paraffin-embedded specimens of the same tumors were used for histopathology and immunohistochemistry.

Image cytometry was performed on Feulgen-stained touch preparation slides. The staining procedure, internal standardization, and tumor cell selection were based on methods described previously (Auer et al., *Cancer Res*, 44, 394-96 (1984)). All DNA-values were expressed in relation to the corresponding staining controls which were given the value 2c, denoting the normal diploid DNA-content. The tumors divided into three groups: (1) diploid cases with a distinct peak in the normal 2c region and no cells exceeding 5c, (2) aneuploid cases with a main peak different from 2c and a stemline scatter index (SSI) below or equal 8.8, and (3) aneuploid samples with varying number of cells (>5%) exceeding 5c (SSI above 8.8). This novel classification system adheres to the parameters established by Kronenwett et al. who defined SSI as a measurement of clonal heterogeneity in the tumor cell population (Kronenwett et al., *Cancer Res*, 64(3), 904-9 (2004); and Kronenwett et al., *Cancer Epidemiol Biomarkers Prev*, 15(9), 1630-5 (2006)).

Of the 48 samples, 17 tumors were assessed as diploid and genomically stable (dGS), 15 tumors were assessed as aneuploid, yet genomically stable (aGS), and 16 tumors were classified as aneuploid and genomically unstable (aGU). The degree of genomic instability status was compared with grading using the Pearson's Chi-square test with non-categorized parameters (age, tumor size, number of lymph nodes with metastases, and cyclin A labeling index) using the Kruskall-Wallis test.

No significant differences were observed among the three groups regarding patients' age, tumor size and number of lymph node metastases. However, a significant relationship existed between the degree of genomic instability and cyclin A labeling index (p<0.0001 by Kruskal-Wallis test). Moreover, tumors with high grade (Grade III) were significantly more frequently found in the aGU group compared with the dGS and aGS group (p<0.0001 by Pearson's Chi-square test). The higher degree of genomic instability in the aGU group also was reflected in an increase in chromosomal copy number changes as measured by comparative genomic hybridization (CGH). Chromosomal imbalances in the genomically stable tumors (dGS and aGS) were mostly restricted to gains of chromosome 1q and 16p, accompanied by losses on chromosome 16q, while aGU tumors showed more diverse changes, including frequent gain of the long arm of chromosome 17, the mapping position of the ERBB2 oncogene.

Gene expression of the 48 samples was analyzed by microarray. The Wilcoxon test with permutation test and the step-wise algorithm was applied to identify differentially expressed genes for the pair-wise comparisons of the three groups. 38 genes were commonly differentially expressed for the comparisons aGU versus dGS and aGU versus aGS, whereas only two genes were commonly observed in the comparisons aGU versus aGS and aGS versus dGS, and three genes among aGS versus dGS and aGU versus dGS (Table 2).

The expression of several genes potentially involved in the control of genetic stability were examined, including APC, BIRC5, BUB1, CDH1, FRS3, RB1CC1, SMC1A (structural maintenance of chromosome), ST7, AURKA, TP53, and the cyclins CCNA2, CCND1, CCND3, and CCNE1. Five of these genes were significantly differentially expressed between the genomically stable (dGS and aGS) and unstable (aGU) tumors. The expression of CCNA2 and CCNE1 was increased in the unstable tumors as compared to the stable tumors; however, CCND1 was downregulated. In addition, expression of both BIRC5, which prevents apoptosis, and AURKA, a gene involved in centrosome duplication and genomic instability, was significantly higher in the genomically unstable tumors as compared to the genomically stable tumors.

These results show that the tumors classified as genetically unstable differed most from the genetically stable tumors, regardless of the actual ploidy status (i.e., the position of the stemline which is at 2c in the dGS, and different from 2c in the aGS group). A functional annotation of the differentially expressed genes between the two groups (dGS and aGS versus aGU) using Ingenuity Pathway Analysis (IPA) showed that 38 genes were differentially expressed between the aGU and the dGS/aGS subtypes, of which 33 were present as focus genes. Four of these focus genes belonged to the highest ranked network, indicating an involvement in cancer development, cellular growth and proliferation, or gene expression. One of the focus genes belonged to the second network, indicating involvement in cell-to cell signaling and interaction, cellular assembly, or organization. The top ranked networks are characterized by a low likelihood that the generation of the network was serendipitous.

Example 2

The following example demonstrates the correlation between genomic instability and the expression of a 12-gene signature.

A supervised machine learning approach was applied in two sample settings to identify a genomic instability signature from the expression profiles of 7,657 genes in 44 of the primary breast cancer samples described in Example 1. Using random forests, the gene expression data from the three groups of tumors (dGS, aGS, and aGU) was compared. This comparison and classification generated a list of 70 genes. The top 10 genes of this set were selected with Relief, and then used to individually classify the three groups. This classification achieved an accuracy of 80%.

Random forests was then used to establish a gene list that discerns the genomically stable (dGS and aGS) tumors from the genomically unstable ones (aGU). Seven genes were identified from the analysis. In leave-one-out cross-validation, this 7-gene signature allowed classification of genomically stable versus unstable tumors with an accuracy of 93%.

The 7-gene list and the 10-gene list showed an overlap of five genes. The resulting two largely concordant signatures from both approaches confirmed the relevance of the identified signature genes as descriptors of genomic instability. Combining the two gene lists therefore resulted in a 12-gene genomic instability signature comprising the following: CDKN2A, SCYA18, STK15, NXF1, cDNA Dkfzp762M127, p28, KIAA0882, MYB, Human clone 23948, RERG, HNF3A, and Incyte EST Clone ID 88935 (SEQ ID NO: 21). Probes for these genes were generated using target sequences as set forth below:

| Gene | Target Sequence (by SEQ ID NO) |
| --- | --- |
| CDKN2A | 22 (3p) |
|  | 23 (5p) |
| SCYA18 | 24 (3p) |
|  | 25 (5p) |
| STK15 | 26 (3p) |
|  | 27 (5p) |
| NXF1 | 28 (5p) |
| cDNA Dkfzp762M127 | 29 (3p) |
|  | 30 (5p) |

-continued

| Gene | Target Sequence (by SEQ ID NO) |
|---|---|
| p28 | 31 (5p) |
| KIAA0882 | 32 (3p) |
|  | 33 (5p) |
| MYB | 34 (3p) |
|  | 35 (5p) |
| Human clone 23948 | 36 (3p) |
|  | 37 (5p) |
| RERG | 38 (3p) |
|  | 39 (5p) |
| HNF3A | 40 (3p) |
|  | 41 (5p) |
| Incyte EST Clone ID 88935 | 21 (5p) |

A Hierarchical Cluster analysis based on the 12-gene signature classified the samples into two major groups: genomically stable and unstable. Eight of twelve signature genes also were identified in the previous two-step differential expression analyses (Wilcoxon test and step-wise algorithm, see above), indicating concordance despite different computational approaches. Among the 12-gene genomic instability signature, SCYA18, STK15, and CDKN2A were over-expressed in genomically unstable breast carcinomas, whereas the remaining nine signature genes were under-expressed in genomically unstable tumors (p<0.001, two-sided t-tests).

Example 3

The following example demonstrates the use of the 12-gene signature to classify tumors in an independent validation set.

Patients with breast cancer from three data sets (n=469), for which different clinical endpoints were available, were used to validate the 12-gene signature. The three data sets are described in van de Vijver et al., *N Engl J Med*, 347 (25), 1999-2009 (2002), Sotiriou et al., *Proc Natl Acad Sci USA*, 100 (18), 10393-8 (2003), and Sorlie et al., *Proc Natl Acad Sci USA*, 100 (14), 8418-23 (2003). These datasets comprise gene expression profiles from 469 patients with heterogeneous histology and different disease stages. The clinical parameters included tumor grade, tumor size, lymph node status, estrogen receptor status, progesterone receptor status, age, and histology. The clinical endpoints used for the validation of the classifiers included relapse-free survival, metastasis-free survival, disease-free survival (here a disease event refers to either breast cancer relapse or metastasis) and overall survival.

Each patient in the three validation cohorts was classified as being more similar to either the genomically stable signature (groups dGS and aGS) or the aGU signature, based on the correlation of this gene expression pattern of the sample with the average expression profiles of the genomically stable samples (referred to as GS) and aGU samples in the dataset described in Example 1. The external validation sets exhibited strong correlation patterns with the GS and aGU centroids of the original samples, rendering a robust classification of genomically stable and unstable breast cancers in the validation cohorts. Kaplan-Meier analyses showed that the genomic instability-defined prognostic groups were associated with a distinct relapse-free survival and metastasis-free survival (p<0.04, log-rank tests) in the patient cohorts from Sorlie et al., van de Vijver et al., and Sotiriou et al. Patients with the GS signature had longer relapse-free survival and metastasis-free survival than those with the aGU signature. Furthermore, the genomic-instability defined prognostic groups had remarkably different overall survival in Kaplan-Meier analyses (p<0.025, log-rank tests), despite the fact that about 50% of patients died without having suffered from breast cancer recurrence (FIG. 1).

The association between genomic instability-defined risk groups and traditional prognostic factors of breast cancer also was evaluated. The traditional prognostic factors considered included lymph node status, tumor grade, the NIH consensus criteria (Eifel et al., *J Natl Cancer Inst*, 93(13), 979-89 (2001)), and the St. Gallen criteria (Goldhirsch et al., *J Natl Cancer Inst*, 90(21), 1601-8 (1998)) The NIH and St. Gallen criteria are based on tumor size ≤1 cm (NIH low risk), and estrogen (positive) and/or progesterone (positive) receptor status, tumor size (≤2 cm), tumor grade (Grade I), and patient age (≥35 years) (St. Gallen low risk).

To investigate whether the 12-gene signature is independent of lymph node status, the three external validation cohorts were combined, and lymph node-negative patients and node-positive patients were analyzed separately. In all studied lymph node-negative patients, the GS and the aGU groups had distinct disease-free survival (p<0.0002, log-rank tests) and overall survival (p<0.0001, log-rank tests) in Kaplan-Meier analyses. Similarly, in all lymph node-positive patients, the GS group and the aGU group had remarkably different disease-free survival (p<0.0007, log-rank tests) and overall survival (p<0.0001, log-rank tests). These results indicate that the 12-gene genomic instability signature is independent of lymph node status in breast cancer prognosis (FIG. 2).

The 12-gene signature was analyzed against the NIH criteria and the St. Gallen criteria to see if the signature provided additional prognostic information within these high risk groups. In van de Vijver's cohort, 284 patients were defined as high risk according to the NIH criteria, and 273 patients were defined as high risk according to the St. Gallen criteria. In Sotiriou's cohort, 93 patients were defined as NIH high-risk, and 91 patients were defined as St. Gallen high-risk. Since tumor size was not available in Sorlie's cohort, patients could not be classified using the NIH criteria. All 75 patients in Sorlie's cohort were high-risk according to St. Gallen criteria.

In high risk patients defined by the NIH criteria (n=377), those with the GS signature had significantly better prognosis in terms of metastasis-free survival (p<0.0001, log-rank tests) and overall survival (p<0.0001, log-rank tests) than those with the aGU signature (FIG. 3A). Similarly, in the high risk patients defined by the St. Gallen criteria (n=439), patients with the GS signature had significantly better prognosis in terms of metastasis-free survival (p<0.0001, log-rank tests) and overall survival (p<0.0001, log-rank tests) than those with the aGU signature (FIG. 3A).

Furthermore, the 12-gene genomic instability signature stratified Grade II breast cancers (n=172) into subgroups with distinct relapse-free survival (p=0.0001, log-rank tests) and overall survival (p=0.0001, log-rank tests) in Sorlie's cohort and van de Vijver's cohort (FIG. 3B). Together, these results demonstrate that the 12-gene genomic instability signature is independent of traditional clinicopathologic factors used for breast cancer prognostication.

Thus, based on direct mapping, the 12-gene signature reliably predicted disease-free survival and overall survival in breast cancer independently of traditional prognostic factors, including tumor grade, lymph node status, and the St. Gallen and NIH consensus criteria. These results further suggest inherent biological similarities between the parameters that define the classification systems, which are reflected in the 12-gene signature. The external validation sets used in this study consist of completely independent patient cohorts. The prognostic prediction based on the 12-gene genomic instability signature employed the "gold standard" of validation schemes, i.e., an independent training set and a validation in multiple, non-overlapping datasets.

Example 4

The following example provides a comparison of prognostic conclusions based on the genomic instability gene signature of the invention to prognostic conclusions based on known, subtype-specific gene signatures.

Several comprehensive gene expression based tumor profiling studies of large cohorts of breast cancer patients identified specific breast cancer subtypes, i.e., luminal A and B, basal, ERBB2+, and normal-like (see Sorlie et al, *Proc Natl Acad Sci USA*, 98(19), 10869-74 (2001); Sorlie et al, *Proc Natl Acad Sci USA*, 100(14), 8418-23 (2003); Perou et al., *Nature*, 406(6797), 747-52 (2000); Bergamaschi et al., *Genes Chromosomes Cancer*, 45(11), 1033-40 (2006)). These subtypes were reproduced in several independent studies, and are associated with distinct prognostic profiles. For instance, luminal A and normal-like are associated with longer disease-free survival, whereas patients with tumors classified as basal or ERBB2+ fare worse.

The same subtype-specific gene expression signatures were used to classify the 48 samples described in Example 1. Of the 28 genomically stable tumors, 24 were assigned to subtypes luminal A (n=18) or normal-like (n=6). Only four tumors were assigned to the ERBB2+ group. In contrast, all but one genomically unstable tumor (n=16) was assigned to either the ERBB2+ group (n=10) or the basal group (n=5), indicating poor prognosis. Of note, most of the genomically unstable tumors showed genomic amplification of chromosome arm 17q, the mapping position of the ERBB2 oncogene. The congruence was striking: 24 of 28 of the genomically stable (i.e., good prognosis) tumors were identified as being either luminal A or normal-like, whereas 15 of 16 genomically unstable (i.e., poor prognosis) tumors belonged to either the basal or ERBB2+ groups. Gain of chromosome 17q, on which ERBB2 resides, was common in the genomically unstable tumors, hence supporting the ERBB2+ phenotype.

The results reveal a remarkable concordance of these independent classification systems. This overlap points to a strong biological relationship of the groups, and suggests that tumor inherent genomic instability is a major determinant of prognosis.

Example 5

The following example provides a comparison of the genomic instability gene signature of the invention to other gene signatures in classifying genomic instability.

The 21-gene signature of the Oncotype DX assay (Genomic Health Inc.) (consisting of 16 cancer-associated genes and 5 genes included for normalization purposes) (Paik et al., *N Engl J Med*, 351(27), 2817-26 (2004)) and the 70-gene signature of the MammaPrint® assay (Agendia Inc.) (van de Vijver et al., supra; van't Veer et al., *Nature*, 415(6871), 530-6 (2002)) were used to predict genomic instability in the tumors described in Example 1. Twelve of the 21 genes used in the Oncotype DX test were present on the microarray used in the original analysis, whereas 21 of the 70 genes employed by MammaPrint® were utilized. Using the Oncotype DX gene set, overall prediction accuracy (measured as correct classification of unstable tumors as unstable, and stable tumors as stable) was 91%, whereas the MammaPrint® set correctly classified 84% of cases.

These results are further proof of the linkage between genomic instability and poor prognosis in breast cancer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used, the substitution of a closed-ended term (e.g., "consisting essentially of" or "consisting of") is specifically contemplated. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

TABLE 1

| Case | Ploidy | Age | Size (mm) | Elston Grade | Histology | Side | Lymphnode Metastasis | Cyclin A Positivity | Surgery | CGH | cDNA Array | Subtype |
| --- | --- | --- | --- | --- | --- | --- | --- | --- | --- | --- | --- | --- |
| D03 | dGS | 61 | ND | II | ductal | left | 0/0 | 0% | lumpectomy | Yes | Yes | Normal-like |
| D05 | dGS | 83 | 30 | II | ductal | right | 0/3 | 2% | mastectomy | Yes | Yes | Normal-like |

TABLE 1-continued

| Case | Ploidy | Age | Size (mm) | Elston Grade | Histology | Side | Lymphnode Metastasis | Cyclin A Positivity | Surgery | CGH | cDNA Array | Subtype |
|---|---|---|---|---|---|---|---|---|---|---|---|---|
| D07 | dGS | 41 | 18 | II | mucin | left | 0/11 | 6% | lumpectomy | Yes | Yes | Normal-like |
| D08 | dGS | 51 | 12 | ND | lobular | right | 0/8 | 1% | mastectomy | Yes | Yes | Normal-like |
| D09 | dGS | 48 | 25 × 20 | II | lobular | left | 0/0 | 1% | mastectomy | Yes | Yes | Luminal A |
| D10 | dGS | 83 | 45 | II-III | ductal | left | 3/7 | 3% | mastectomy | Yes | No | |
| D11 | dGS | 60 | 12 | II | ductal | bilateral | 0/ND | 1% | lumpectomy | Yes | No | |
| D12 | dGS | 75 | 12 | I | tubular | right | 0/0 | 5% | lumpectomy | Yes | Yes | Luminal A |
| D13 | dGS | 86 | 10 | ND | lobular | left | 0/0 | 4% | recurrent | Yes | Yes | Luminal A |
| D14 | dGS | 86 | 26 | I | ductal | right | 4/6 | 3% | lumpectomy | Yes | Yes | Luminal A |
| D15 | dGS | 50 | ND | II | lobular | right | 3/9 | 2% | mastectomy | Yes | Yes | Normal-like |
| D16 | dGS | 54 | 70 | III | lobular | left | 1/12 | 2% | mastectomy | Yes | Yes | Luminal A |
| D18 | dGS | 48 | 14 | II | ductal | left | 0/7 | 4% | mastectomy | Yes | No | |
| D19 | dGS | 62 | 20 | I | ductal | right | 0/3 | 8% | lumpectomy | No | Yes | Luminal A |
| D21 | dGS | 79 | 22 | II | ductal | left | 4/16 | 4% | mastectomy | Yes | Yes | Luminal A |
| D23 | dGS | 34 | 10 | II | ductal | left | 0/0 | 4% | lumpectomy | No | Yes | Luminal A |
| D25 | dGS | 71 | 12 | I | lobular | ND | 0/0 | 1% | lumpectomy | Yes | Yes | ERRB2+ |
| NP01 | aGS | 55 | 60 | III | ductal | right | 9/9 | 2% | mastectomy | Yes | Yes | Luminal A |
| NP02 | aGS | 62 | 11 | I | ductal | right | 0/23 | 6% | mastectomy | Yes | Yes | Luminal A |
| NP06 | aGS | 72 | 15 | II | ductal | left | 0/5 | 1% | mastectomy | Yes | Yes | Luminal A |
| NP08 | aGS | 58 | 14 | I | ductal | left | 0/0 | 3% | lumpectomy | Yes | Yes | Normal-like |
| NP10 | aGS | 71 | ND | II | Paget's | right | 0/0 | 4% | lumpectomy | No | Yes | Normal-like |
| NP11 | aGS | 81 | 26 | II | ductal | left | 1/7 | 2% | mastectomy | Yes | Yes | Luminal A |
| NP12 | aGS | 62 | 60 + 15 | I | lobular | right | 2/7 | 6% | mastectomy | Yes | Yes | Luminal A |
| NP13 | aGS | 75 | 13 | I | ductal | left | 0/0 | 0% | lumpectomy | Yes | Yes | Luminal A |
| NP14 | aGS | 54 | 12 + 9 | II | ductal | right | 0/0 | 1% | lumpectomy | Yes | Yes | ERRB2+ |
| NP16 | aGS | 49 | 54 | III | ductal/lobular | right | 0/0 | 0% | mastectomy | No | Yes | ERRB2+ |
| NP17 | aGS | 52 | 14 | II | ductal | right | 0/6 | 8% | mastectomy | Yes | Yes | Luminal A |
| NP18 | aGS | 63 | 30 | II | ductal | left | 0/0 | 4% | mastectomy | No | Yes | ERRB2+ |
| NP19 | aGS | 54 | 10 | II | ductal | right | 0/6 | 6% | lumpectomy | Yes | No | |
| NP20 | aGS | 43 | 20 | III | ductal | left | 0/6 | 6% | lumpectomy | Yes | Yes | Luminal A |
| NP22 | aGS | 88 | 20 | III | ductal | left | 0/0 | 6% | mastectomy | Yes | Yes | Luminal A |
| A01 | aGU | 54 | 20 | III | ductal | right | 0/5 | 20% | mastectomy | Yes | Yes | Basal |
| A02 | aGU | 62 | 35 | III | comedo | right | 0/35 | 15% | mastectomy | No | Yes | ERRB2+ |
| A03 | aGU | 43 | 35 | III | ductal | left | 0/0 | ND | mastectomy | No | Yes | ERRB2+ |
| A04 | aGU | 46 | 20 | III | ductal | left | 0/0 | 11% | mastectomy | Yes | Yes | Basal |
| A05 | aGU | 54 | 30 | III | medullar | ND | 14/15 | 30% | mastectomy | No | Yes | ERRB2+ |
| A06 | aGU | 74 | 40 | III | ductal | left | 0/17 | 10% | mastectomy | Yes | Yes | Basal |
| A07 | aGU | 55 | 40 | III | ductal | right | 0/0 | 1% | mastectomy | Yes | Yes | ERRB2+ |
| A10 | aGU | 71 | 30 | III | ductal | left | 0/0 | 54% | lumpectomy | Yes | Yes | Luminal A |
| A12 | aGU | 79 | 16 | III | ductal | left | 4/14 | 10% | mastectomy | No | Yes | Luminal A |
| A14 | aGU | 57 | 25 | III | ductal | left | 0/2 | 12% | mastectomy | Yes | Yes | ERRB2+ |
| A15 | aGU | 59 | 20 | III | ductal | left | 1/9 | 5% | mastectomy | No | Yes | ERRB2+ |
| A16 | aGU | 85 | 45 | III | comedo | right | 0/3 | 9% | mastectomy | Yes | Yes | ERRB2+ |
| A17 | aGU | 66 | 12 | III | lobular | left | 0/0 | 14% | lumpectomy | Yes | Yes | ERRB2+ |
| A18 | aGU | 62 | 12 | II | ductal | right | 0/10 | 23% | lumpectomy | Yes | Yes | Basal |
| A19 | aGU | 60 | 18 + 9 | III | ductal | ND | 0/ND | 62% | lumpectomy | Yes | Yes | Basal |
| A20 | aGU | 57 | 8 | III | metaplastic | right | 0/0 | 17% | lumpectomy | Yes | Yes | ERRB2+ |

ND, not determined.
The column "subtype" refers to the classification established from the analyses, and not to the actual clinical subtype.

TABLE 2

| Nr | Incyte PD | Gene name | ENTREZ Gene ID | Location | Gene function | Ratio aGU/dGS | Ratio aG/aGS | α-value aGU/dGS | α-value aGU/aGS |
|---|---|---|---|---|---|---|---|---|---|
| | | Genes similar expressed for "aGU versus dGS" and "aGU versus aGS" | | | | | | | |
| 1 | 62144 | CCNE1 - cyclin E1 | 898 | 19q12 | Overexpression is known for many tumors and results in chromosome instability. | 2.23 | 2.34 | 0.0479 | 0.0407 |
| 2 | 520342 | EVL - Enah/Vasp-like | 51466 | 14q32.32 | Cytoskeletal regulator activity and cell surface receptor linked signal transduction. | 0.28 | 0.39 | 0.0478 | 0.0431 |

TABLE 2-continued

| Nr | Incyte PD | Gene name | ENTREZ Gene ID | Location | Gene function | Ratio aGU/dGS | Ratio aG/aGS | α-value aGU/dGS | α-value aGU/aGS |
|---|---|---|---|---|---|---|---|---|---|
| 3 | 522991 | SUSD3 | 203328 | 9q22.32 | Sushi domain containing 3 | 0.27 | 0.35 | 0.0463 | 0.0405 |
| 4 | 606609 | VAV3 - vav 3 oncogene | 10451 | 1p13.3 | Function in signal transduction. Deregulation leads to marked cytoskeletal changes and cell division alterations. | 0.39 | 0.39 | 0.043 | 0.0459 |
| 5 | 644989 | RERG - Ras-like | 85004 | 12p13.1 | Estrogen-regulated, growth inhibitor | 0.32 | 0.26 | 0.0464 | 0.0482 |
| 6 | 690231 | CCL18 - chemokine (C-C motif) ligand 18 (pulmonary and activation-regulated) | 6362 | 17q11.2 | Chemotactic activity for naive T cells, CD4+ and CD8+ T cells and nonactivated lymphocytes. It may play a role in humoral and cell-mediated immunity responses. | 4.25 | 6.34 | 0.0481 | 0.0439 |
| 7 | 1394835 | HOOK2 - hook homolog 2 | 29911 | 19p13.13 | Attachment to microtubules and binding to organelles. | 0.47 | 0.40 | 0.0464 | 0.0458 |
| 8 | 1453049 | SCNN1A | 6337 | 12p13 | Sodium channel, nonvoltage-gated 1 alpha | 0.25 | 0.20 | 0.0456 | 0.0402 |
| 9 | 1646030 | PTD008 | 51398 | 19p13.13 | PTD008 protein | 0.47 | 0.46 | 0.0424 | 0.0465 |
| 10 | 1662893 | C18orf1 | 753 | 18p11.2 | Chromosome 18 open reading frame 1 | 0.40 | 0.37 | 0.0462 | 0.0432 |
| 11 | 1672574 | PACE4 - proprotein convertase subtilisin/kexin type 6 | 5046 | 15q26 | One of its substrates is the transforming growth factor beta related protein. This gene plays a role in tumor progression. | 0.36 | 0.37 | 0.0495 | 0.0452 |
| 12 | 1698713 | ERBB3 - v-erb-b2 erythroblastic leukemia viral oncogene homolog 3 (avian) | 2065 | 12q13 | Encodes a member of the epidermal growth factor receptor (EGFR) family. Function in cell proliferation or differentiation. Amplification of this gene and/or overexpression of its protein have been reported also in breast tumors. | 0.38 | 0.42 | 0.0457 | 0.0426 |
| 13 | 1711594 | FOXA1 - forkhead box A1 | 3169 | 14q12-q13 | HNF3alpha is amplified and overexpressed in esophageal and lung adenocarcinomas. | 0.16 | 0.14 | 0.043 | 0.0443 |
| 14 | 1734634 | NaN | | NaN | | 0.31 | 0.27 | 0.0491 | 0.0454 |
| 15 | 1749102 | INDO - indoleamine-pyrrole2,3dioxygenase | 3620 | 8p12-p11 | Antiproliferative effect on many tumor cells and inhibits intracellular pathogens. | 3.20 | 4.50 | 0.0464 | 0.0428 |
| 16 | 1755193 | FLJ20366 | 55638 | 8q23.2 | Hypothetical protein FLJ20366 | 0.32 | 0.30 | 0.0435 | 0.0476 |
| 17 | 1793853 | ALCAM | 214 | 3q13.1 | Activated leukocyte cell adhesion molecule | 0.38 | 0.37 | 0.0478 | 0.0439 |

TABLE 2-continued

| Nr | Incyte PD | Gene name | ENTREZ Gene ID | Location | Gene function | Ratio aGU/dGS | Ratio aG/aGS | α-value aGU/dGS | α-value aGU/aGS |
|---|---|---|---|---|---|---|---|---|---|
| 18 | 1808121 | KIAA1324 | 57535 | 1p13.3-p13.2 | | 0.31 | 0.30 | 0.0491 | 0.0478 |
| 19 | 1844691 | ARMCX2 | 9823 | Xq21.33-q22.2 | Potential role in tumor suppression. | 0.40 | 0.41 | 0.0455 | 0.0419 |
| 20 | 1861614 | CREB3L4 | 148327 | 1q21.3 | cAMP response element-binding (CREB) proteins are transcription activators. | 0.41 | 0.42 | 0.0475 | 0.0463 |
| 21 | 1922038 | SYT17 | 51760 | 16p13.11 | Synaptotagmin XVII | 0.40 | 0.37 | 0.0463 | 0.0416 |
| 22 | 1998428 | AGR2 - anterior gradient 2 homolog (*Xenopus laevis*) | 10551 | 7p21.3 | Involvement in differentiation, associated with oestrogen receptor-positive breast tumours and interacts with metastasis gene C4.4a and dystroglycan. | 0.23 | 0.25 | 0.0437 | 0.0444 |
| 23 | 1998792 | DNALI1 | 7802 | 1p35.1 | Potential candidate for the immotile cilia syndrome (ICS). | 0.34 | 0.40 | 0.0448 | 0.0448 |
| 24 | 2026332 | NaN | | NaN | | 0.25 | 0.30 | 0.0462 | 0.0447 |
| 25 | 2106441 | ASAH1 | 427 | 8p22-p21.3 | Mutations are associated with a lysosomal storage disorder (Farber disease). | 0.33 | 0.32 | 0.0468 | 0.0452 |
| 26 | 2190664 | KIAA0882 | 23158 | 4q31.21 | Membrane-associated protein. | 0.22 | 0.26 | 0.0495 | 0.0463 |
| 27 | 2230088 | MGC18216 | 145815 | 15q26.3 | Hypothetical protein MGC18216. | 0.35 | 0.31 | 0.0463 | 0.0438 |
| 28 | 2242817 | TFF3 - trefoil factor 3 (intestinal) | 7033 | 21q22.3 | May protect the mucosa from insults, stabilize the mucus layer and affect healing of the epithelium. Expressed in goblet cells of the intestines and colon. | 0.34 | 0.17 | 0.048 | 0.0446 |
| 29 | 2366522 | TMEM101 | 84336 | 17q21.31 | Transmembrane protein 101 | 0.33 | 0.35 | 0.0478 | 0.0454 |
| 30 | 2555590 | MYB | 4602 | 6q22-q23 | V-myb myeloblastosis viral oncogene homolog | 0.27 | 0.20 | 0.0482 | 0.0418 |
| 31 | 2591494 | SELENBP1 - selenium binding protein 1 | 8991 | 1q21-q22 | Effects of selenium in preventing cancer and neurologic diseases may be mediated by selenium-binding proteins. | 0.41 | 0.34 | 0.0453 | 0.0451 |
| 32 | 2617968 | ShrmL - shroom | ShrmL | 4q21.22 | F-actin-binding protein | 0.51 | 0.44 | 0.0469 | 0.0479 |
| 33 | 2708596 | KIF13B | 23303 | 8p12 | Kinesin family member 13B | 0.33 | 0.42 | 0.0463 | 0.045 |
| 34 | 2740665 | NaN | | NaN | | 0.34 | 0.26 | 0.045 | 0.0431 |
| 35 | 2823476 | STC2 - stanniocalcin 2 | 8614 | 5q35.1 | Expression is induced by estrogen and altered in some breast cancers. | 0.34 | 0.35 | 0.0441 | 0.0451 |
| 36 | 3094261 | GREB1 - GREB1 protein | 9687 | 2p25.1 | Estrogen-responsive; plays important role in hormone-responsive tissues and cancer. | 0.53 | 0.33 | 0.0487 | 0.0457 |

TABLE 2-continued

| Nr | Incyte PD | Gene name | ENTREZ Gene ID | Location | Gene function | Ratio aGU/dGS | Ratio aG/aGS | α-value aGU/dGS | α-value aGU/aGS |
|---|---|---|---|---|---|---|---|---|---|
| 37 | 3123244 | NaN | | 15q22.32 | | 0.17 | 0.21 | 0.0487 | 0.042 |
| 38 | 4256950 | NPHP1 - nephronophthisis 1 | 4867 | 2q13 | Signal transduction, cell-cell adhesion, actin cytoskeleton organization and biogenesis. | 0.37 | 0.22 | 0.0469 | 0.0455 |
| Genes similar expressed for "aGU versus dGS" and "aGS versus dGS" | | | | | | | | | |
| 1 | 1596916 | NOL4 | 8715 | 18q12 | Nucleolar protein 4 | 2.78 | 2.13 | 0.0458 | 0.0434 |
| 2 | 2060823 | S100P - S100 calcium binding protein P | 6286 | 4p16 | Regulation of cellular processes such as cell cycle progression and differentiation. | 2.36 | 2.77 | 0.0474 | 0.0479 |
| 3 | 2518249 | AFF3 - AF4/FMR2 family, member 3 | 3899 | 2q11.2-q12 | Tissue-restricted nuclear transcriptional activator preferentially expressed in lymphoid tissue. May function in lymphoid development and oncogenesis. | 0.21 | 0.43 | 0.046 | 0.044 |
| Genes similar expressed for "aGU versus aGS" and "aGS versus dGS" | | | | | | | | | |
| 1 | 2313368 | MS4A1 - membrane-spanning 4-domains, subfamily A, member 1 | 931 | 11q12 | Encodes a B-lymphocyte surface molecule with function in development and differentiation of B-cells into plasma cells. | 0.43 | 3.44 | 0.0429 | 0.0478 |
| 2 | 3970665 | NaN | | NaN | | 2.11 | 0.34 | 0.0469 | 0.0414 |

The invention claimed is:

1. A method of assessing genomic instability in breast cancer tissue comprising
   (a) obtaining a sample of breast cancer tissue,
   (b) measuring the expression level of (i) and (ii) in the sample to provide an expression profile of the breast cancer tissue
      (i) CDKN2A, SCYA18, STK15, NXF1, cDNA Dkfzp762M127, p28, KIAA0882, MYB, Human clone 23948, RERG, HNF3A, and
      (ii) ACADSB or a nucleic acid sequence comprising about 90% or greater sequence identity to SEQ ID NO: 21, and
   (c) comparing the expression profile of the breast cancer tissue to a control by calculating the correlation coefficient of the expression profile of the breast cancer tissue with respect to the control,
   wherein when the control is the average expression profile of the genes of (b) in a pool of known genomically stable breast cancer tissue samples then a correlation coefficient of −0.5 (P=0.05) or less indicates genomic instability in the breast cancer tissue, and
   wherein when the control is the average expression profile of the genes of (b) in a pool of known genomically unstable breast cancer tissue samples then a correlation coefficient of 0.5 (P=0.05) or greater indicates genomic instability in the breast cancer tissue.

2. A method of assessing genomic instability in breast cancer tissue comprising
   (a) obtaining a sample of breast cancer tissue,
   (b) measuring the expression level of (i) and (ii) in the sample to provide an expression profile of the breast cancer tissue:
      (i) CDKN2A, SCYA18, STK15, NXF1, cDNA Dkfzp762M127, p28, KIAA0882, MYB, Human clone 23948, RERG, HNF3A, and
      (ii) ACADSB or a nucleic acid sequence comprising about 90% or greater sequence identity to SEQ ID NO: 21, and
   (c) comparing the expression profile of the breast cancer tissue to a first and second control by calculating the correlation coefficient of the expression profile of the breast cancer tissue with respect to each of the first and second controls, wherein the first control is the average expression profile of the genes of (b) in a pool of known genomically stable breast tissue samples and the second control is the average expression profile of the genes of (b) in a pool of known genomically unstable breast tissue samples,
   wherein genomic instability is indicated if the correlation coefficient of the expression profile of the breast cancer tissue calculated with respect to the second control is greater than the correlation coefficient of the expression profile of the breast cancer tissue calculated with respect to the first control.

3. A method of detecting genomic instability in breast cancer tissue comprising
   (a) obtaining a sample of breast cancer tissue,
   (b) measuring the expression level of (i) and (ii) in the sample relative to the expression of (i) and (ii) in genomically-stable breast tissue:
      (i) NXF1, cDNA Dkfzp762M127, p28, KIAA0882, MYB, Human clone 23948, RERG, HNF3A, and
      (ii) ACADSB or a nucleic acid sequence comprising about 90% or greater sequence identity to SEQ ID NO: 21, and
   (c) measuring the expression level of genes CDKN2A, SCYA18, and STK15 in the breast cancer tissue relative to the expression of the same genes in genomically-stable breast tissue,
   wherein genomic instability is indicated if (i) and (ii) are under-expressed in the breast cancer tissue as compared to the expression of the same genes in genomically-stable breast tissue, and CDKN2A, SCYA18, and STK15 are over-expressed in the breast cancer tissue as compared to the expression of the same genes in genomically-stable breast tissue.

4. The method of claim 1, wherein the expression level of the genes is determined by microarray analysis.

5. A method of screening for a compound that alters genomic instability in breast tissue comprising
   (a) contacting one or more test compounds with a sample of breast tissue, and
   (b) comparing the expression level of (i) and (ii) in the sample of breast tissue after contact with the one or more test compounds with the expression level of (i) and (ii) in breast tissue in the absence of the one or more test compounds:
      (i) CDKN2A, SCYA18, STK15, NXF1, cDNA Dkfzp762M127, p28, KIAA0882, MYB, Human clone 23948, RERG, HNF3A, and
      (ii) ACADSB or a nucleic acid sequence comprising about 90% or greater sequence identity to SEQ ID NO: 21
   wherein a change in the expression level of (i) and (ii) after contact with the one or more test compounds as compared to the expression level of (i) and (ii) in the absence of the one or more test compounds indicates that the one or more test compounds alter genomic instability in breast tissue.

6. An array comprising
   (a) a substrate and
   (b) twelve or more different addressable elements that each comprise at least one polynucleotide that binds to an mRNA transcript of
      (i) CDKN2A, SCYA18, STK15, NXF1, cDNA Dkfzp762M127, p28, KIAA0882, MYB, Human clone 23948, RERG, HNF3A, and
      (ii) ACADSB or a nucleic acid sequence comprising about 90% or greater sequence identity to SEQ ID NO: 21,
   or cDNA synthesized therefrom,
   wherein the array comprises 1000 or fewer different addressable elements.

7. The array of claim 6, wherein the array comprises 100 or fewer different addressable elements.

8. The array of claim 7, wherein the array comprises 50 or fewer different addressable elements.

9. The array of claim 8, wherein the array comprises 15 or fewer different addressable elements.

10. The method of claim 3, wherein the expression level of the genes is determined by microarray analysis.

11. The method of claim 5, wherein the expression level of the genes is determined by microarray analysis.

12. A method of assessing genomic instability in breast cancer tissue comprising
   (a) measuring the expression level of (i) CDKN2A, SCYA18, STK15, NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21 in breast cancer tissue to provide an expression profile of the breast cancer tissue, wherein the measuring is performed with the array of claim 6, and (b) comparing the expression profile of the breast cancer tissue to a control.

13. A method of detecting genomic instability in breast cancer tissue comprising (a) measuring the expression level of (i) NXF1, cDNA Dkfzp762M127, p28, KIAA0882, MYB, Human clone 23948, RERG, HNF3A, and (ii) ACADSB or a nucleic acid sequence comprising about 90% or greater sequence identity to SEQ ID NO: 21 in the breast cancer tissue relative to the expression of (i) and (ii) in genomically-stable breast tissue, and (b) measuring the expression level of genes CDKN2A, SCYA18, and STK15 in the breast cancer tissue relative to the expression of the same genes in genomically-stable breast tissue, wherein genomic instability is indicated if (i) and (ii) are under-expressed in the breast cancer tissue as compared to the expression of the same genes in genomically-stable breast tissue, and CDKN2A, SCYA18, and STK15 are over-expressed in the breast cancer tissue as compared to the expression of the same genes in genomically-stable breast tissue, and wherein the measuring is performed using the array of claim 6.

* * * * *

SEQUENCE LISTING

<160> NUMBER OF SEQ ID NOS: 41

<210> SEQ ID NO 1
<211> LENGTH: 1154
<212> TYPE: DNA
<213> ORGANISM: Homo sapiens

<400> SEQUENCE: 1

```
cgctcaggga aggcgggtgc gcgcctgcgg ggcggagatg ggcaggggggc ggtgcgtggg      60 tcccagtctg cagttaaggg ggcaggagtg gcgctgctca cctctggtgc caaagggcgg     120
cgcagcggct gccgagctcg gccctggagg cggcgagaac atggtgcgca ggttcttggt     180
gaccctccgg attcggcgcg cgtgcggccc gccgcgagtg agggttttcg tggttcacat     240
cccgcggctc acgggggagt gggcagcgcc aggggcgccc gccgctgtgg ccctcgtgct     300
gatgctactg aggagccagc gtctagggca gcagccgctt cctagaagac caggtcatga     360
tgatgggcag cgcccgagtg gcggagctgc tgctgctcca cggcgcggag cccaactgcg     420
ccgaccccgc cactctcacc cgacccgtgc acgacgctgc ccgggagggc ttcctggaca     480
cgctggtggt gctgcaccgg gccggggcgc ggctggacgt gcgcgatgcc tggggccgtc     540
tgcccgtgga cctggctgag gagctggccc atcgcgatgt cgcacggtac ctgcgcgcgg     600
ctgcgggggg caccagagggc agtaaccatg cccgcataga tgccgcggaa ggtccctcag     660
```

-continued

```
acatccccga ttgaaagaac cagagaggct ctgagaaacc tcgggaaact tagatcatca    720
gtcaccgaag gtcctacagg gccacaactg cccccgccac aacccacccc gctttcgtag    780
ttttcattta gaaaatagag cttttaaaaa tgtcctgcct tttaacgtag atatatgcct    840
tcccccacta ccgtaaatgt ccatttatat cattttttat atattcttat aaaaatgtaa    900
aaaagaaaaa caccgcttct gccttttcac tgtgttggag ttttctggag tgagcactca    960
cgccctaagc gcacattcat gtgggcattt cttgcgagcc tcgcagcctc cggaagctgt   1020
cgacttcatg acaagcattt tgtgaactag ggaagctcag gggggttact ggcttctctt   1080
gagtcacact gctagcaaat ggcagaacca aagctcaaat aaaaataaaa taattttcat   1140
tcattcactc aaaa                                                     1154

<210> SEQ ID NO 2
<211> LENGTH: 1437
<212> TYPE: DNA
<213> ORGANISM: Homo sapiens

<400> SEQUENCE: 2
ctcctccgag cactcgctca cggcgtcccc ttgcctggaa agataccgcg gtccctccag     60
aggatttgag ggacagggtc ggagggggct cttccgccag caccggagga agaaagagga    120
ggggctggct ggtcaccaga gggtgggcg gaccgcgtgc gctcggcggc tgcggagagg    180
gggagagcag gcagcgggcg gcggggagca gcatggagcc ggcggcgggg agcagcatgg    240
agccttcggc tgactggctg ccacggccg cggcccgggg tcgggtagag gaggtgcggg    300
cgctgctgga ggcggggcg ctgcccaacg caccgaatag ttacggtcgg aggccgatcc    360
aggtgggtag agggtctgca gcgggagcag gggatggcgg gcgactctgg aggacgaagt    420
ttgcagggga attggaatca ggtagcgctt cgattctccg gaaaaagggg aggcttcctg    480
gggagttttc agaagggggtt tgtaatcaca gacctcctcc tggcgacgcc ctggggggctt    540 gggaagccaa ggaagaggaa tgaggagcca cgcgcgtaca gatctctcga atgctgagaa    600
gatctgaagg ggggaacata tttgtattag atgaagtca tgatgatggg cagcgcccga    660
gtggcggagc tgctgctgct ccacggcgcg gagcccaact cgccgaccc cgccactctc    720 acccgacccg tgcacgacgc tgccccggag ggcttcctgg acacgctggt ggtgctgcac    780
cgggccgggg cgcggctgga cgtgcgcgat gcctgggcc gtctgcccgt ggacctggct    840
gaggagctgg ccatcgcga tgtcgcacgg tacctgcgcg cggctgcggg gggcaccaga    900
ggcagtaacc atgcccgcat agatgccgcg gaaggtccct cagacatccc cgattgaaag    960
aaccagagag gctctgagaa acctcgggaa acttagatca tcagtcaccg aaggtcctac   1020
agggccacaa ctgcccccgc cacaacccac cccgctttcg tagttttcat ttagaaaata   1080
gagcttttaa aaatgtcctg ccttttaacg tagatatatg ccttccccca ctaccgtaaa   1140
tgtccattta tatcattttt tatatattct tataaaaatg taaaaaagaa aaacaccgct   1200
tctgcctttt cactgtgttg agttttctg gagtgagcac tcacgcccta agcgcacatt   1260
catgtgggca tttcttgcga gcctcgcagc ctccggaagc tgtcgacttc atgacaagca   1320
ttttgtgaac tagggaagct caggggggtt actggcttct cttgagtcac actgctagca   1380
aatggcagaa ccaaagctca aataaaaata aataattttt cattcattca ctcaaaa      1437

<210> SEQ ID NO 3
<211> LENGTH: 1163
<212> TYPE: DNA
<213> ORGANISM: Homo sapiens
```

<400> SEQUENCE: 3

```
ctcctccgag cactcgctca cggcgtcccc ttgcctggaa agataccgcg gtccctccag    60
aggatttgag ggacagggtc ggaggggggct cttccgccag caccggagga agaaagagga   120
ggggctggct ggtcaccaga gggtggggcg gaccgcgtgc gctcggcggc tgcggagagg   180
gggagagcag gcagcgggcg gcggggagca gcatggagcc ggcggcgggg agcagcatgg   240
agccttcggc tgactggctg gccacggccg cggcccgggg tcgggtagag gaggtgcggg   300
cgctgctgga ggcggggggcg ctgcccaacg caccgaatag ttacggtcgg aggccgatcc   360
aggtcatgat gatgggcagc gcccgagtgg cggagctgct gctgctccac ggcgcggagc   420
ccaactgcgc cgaccccgcc actctcaccc gacccgtgca cgacgctgcc cgggagggct   480
tcctggacac gctggtggtg ctgcaccggg ccggggcgcg gctggacgtg cgcgatgcct   540
ggggccgtct gcccgtggac ctggctgagg agctgggcca tcgcgatgtc gcacggtacc   600
tgcgcgcggc tgcggggggc accagaggca gtaaccatgc ccgcatagat gccgcggaag   660
gtccctcaga catccccgat tgaaagaacc agagaggctc tgagaaacct cgggaaactt   720
agatcatcag tcaccgaagg tcctacaggg ccacaactgc cccgccaca acccacccccg   780
ctttcgtagt tttcatttag aaaatagagc ttttaaaaat gtcctgcctt ttaacgtaga   840
tatatgcctt cccccactac cgtaaatgtc catttatatc attttttata tattcttata   900
aaaatgtaaa aagaaaaac accgcttctg ccttttcact gtgttggagt tttctggagt   960
gagcactcac gccctaagcg cacattcatg tgggcatttc ttgcgagcct cgcagcctcc  1020
ggaagctgtc gacttcatga caagcatttt gtgaactagg gaagctcagg ggggttactg  1080
gcttctcttg agtcacactg ctagcaaatg gcagaaccaa agctcaaata aaaataaaat  1140
aatttttcatt cattcactca aaa                                         1163
```

<210> SEQ ID NO 4
<211> LENGTH: 793
<212> TYPE: DNA
<213> ORGANISM: Homo sapiens

<400> SEQUENCE: 4

```
aggagttgtg agtttccaag ccccagctca ctctgaccac ttctctgcct gcccagcatc    60
atgaagggcc ttgcagctgc cctccttgtc ctcgtctgca ccatggccct ctgctcctgt   120
gcacaagttg gtaccaacaa agagctctgc tgcctcgtct atacctcctg gcagattcca   180
caaaagttca tagttgacta ttctgaaacc agccccagt gccccaagcc aggtgtcatc   240
ctcctaacca agagaggccg gcagatctgt gctgacccca taagaagtg ggtccagaaa   300
tacatcagcg acctgaagct gaatgcctga ggggcctgga gctgcgagg gcccagtgaa   360
cttggtgggc ccaggaggga acaggagcct gagccagggc aatggccctg ccaccctgga   420
ggccacctct tctaagagtc ccatctgcta tgcccagcca cattaactaa ctttaatctt   480
agtttatgca tcatatttca ttttgaaatt gatttctatt gttgagctgc attatgaaat   540
tagtattttc tctgacatct catgacattg tctttatcat cctttcccct ttcccttcaa   600
ctcttcgtac attcaatgca tggatcaatc agtgtgatta gctttctcag cagacattgt   660
gccatatgta tcaaatgaca aatctttatt gaatggtttt gctcagcacc accttttaat   720
atattggcag tacttattat ataaaaggta aaccagcatt ctcactgtga aaaaaaaaa   780
aaaaaaaaaa aaa                                                     793
```

<210> SEQ ID NO 5

<211> LENGTH: 2346
<212> TYPE: DNA
<213> ORGANISM: Homo sapiens

<400> SEQUENCE: 5

| | | | | | |
|---|---|---|---|---|---|
| acaaggcagc | ctcgctcgag | cgcaggccaa | tcggctttct | agctagaggg | tttaactcct | 60 |
| atttaaaaag | aagaaccttt | gaattctaac | ggctgagctc | ttggaagact | tgggtccttg | 120 |
| ggtcgcaggt | gggagccgac | gggtgggtag | accgtgggg | atatctcagt | ggcggacgag | 180 |
| gacggcgggg | acaaggggcg | gctggtcgga | gtggcggagc | gtcaagtccc | ctgtcggttc | 240 |
| ctccgtccct | gagtgtcctt | ggcgctgcct | tgtgcccgcc | cagcgccttt | gcatccgctc | 300 |
| ctgggcaccg | aggcgccctg | taggatactg | cttgttactt | attacagcta | gaggcatcat | 360 |
| ggaccgatct | aaagaaaact | gcatttcagg | acctgttaag | gctacagctc | cagttggagg | 420 |
| tccaaaacgt | gttctcgtga | ctcagcaatt | tccttgtcag | aatccattac | ctgtaaatag | 480 |
| tggccaggct | cagcgggtct | tgtgtccttc | aaattcttcc | cagcgcattc | ctttgcaagc | 540 |
| acaaaagctt | gtctccagtc | acaagccggt | tcagaatcag | aagcagaagc | aattgcaggc | 600 |
| aaccagtgta | cctcatcctg | tctccaggcc | actgaataac | acccaaaaga | gcaagcagcc | 660 |
| cctgccatcg | gcacctgaaa | ataatcctga | ggaggaactg | gcatcaaaac | agaaaaatga | 720 |
| agaatcaaaa | aagaggcagt | gggctttgga | agactttgaa | attggtcgcc | ctctgggtaa | 780 |
| aggaaagttt | ggtaatgttt | atttggcaag | agaaaagcaa | gcaagtttta | tctggctct | 840 |
| taaagtgtta | tttaaagctc | agctggaaaa | agccggagtg | gagcatcagc | tcagaagaga | 900 |
| agtagaaata | cagtcccacc | ttcggcatcc | taatattctt | agactgtatg | gttatttcca | 960 |
| tgatgctacc | agagtctacc | taattctgga | atatgcacca | cttggaacag | tttatagaga | 1020 |
| acttcagaaa | ctttcaaagt | ttgatgagca | gagaactgct | acttatataa | cagaattggc | 1080 |
| aaatgccctg | tcttactgtc | attcgaagag | agttattcat | agagacatta | agccagagaa | 1140 |
| cttacttctt | ggatcagctg | gagagcttaa | aattgcagat | tttgggtggt | cagtacatgc | 1200 |
| tccatcttcc | aggaggacca | ctctctgtgg | caccctggac | tacctgcccc | ctgaaatgat | 1260 |
| tgaaggtcgg | atgcatgatg | agaaggtgga | tctctggagc | cttggagttc | tttgctatga | 1320 |
| atttttagtt | gggaagcctc | cttttgaggc | aaacacatac | caagagacct | acaaagaat | 1380 |
| atcacgggtt | gaattcacat | tccctgactt | tgtaacagag | ggagccaggg | acctcatttc | 1440 |
| aagactgttg | aagcataatc | ccagccagag | gccaatgctc | agagaagtac | ttgaacaccc | 1500 |
| ctggatcaca | gcaaattcat | caaaaccatc | aaattgccaa | acaaagaat | cagctagcaa | 1560 |
| acagtcttag | gaatcgtgca | ggggagaaa | tccttgagcc | agggctgcca | tataacctga | 1620 |
| caggaacatg | ctactgaagt | ttattttacc | attgactgct | gccctcaatc | tagaacgcta | 1680 |
| cacaagaaat | atttgtttta | ctcagcaggt | gtgccttaac | ctccctattc | agaaagctcc | 1740 |
| acatcaataa | acatgacact | ctgaagtgaa | agtagccacg | agaattgtgc | tacttatact | 1800 |
| ggttcataat | ctggaggcaa | ggttcgactg | cagccgcccc | gtcagcctgt | gctaggcatg | 1860 |
| gtgtcttcac | aggaggcaaa | tccagagcct | ggctgtgggg | aaagtgacca | ctctgccctg | 1920 |
| accccgatca | gttaaggagc | tgtgcaataa | ccttcctagt | acctgagtga | gtgtgtaact | 1980 |
| tattgggttg | gcgaagcctg | gtaaagctgt | tggaatgagt | atgtgattct | ttttaagtat | 2040 |
| gaaaataaag | atatatgtac | agacttgtat | tttttctctg | gtggcattcc | tttaggaatg | 2100 |
| ctgtgtgtct | gtccggcacc | ccggtaggcc | tgattgggtt | tctagtcctc | cttaaccact | 2160 |
| tatctcccat | atgagagtgt | gaaaaatagg | aacacgtgct | ctacctccat | ttagggattt | 2220 |

-continued

```
gcttgggata cagaagaggc catgtgtctc agagctgtta agggcttatt ttttaaaaac    2280
attggagtca tagcatgtgt gtaaacttta aatatgcaaa taaataagta tctatgtcta    2340
aaaaaa                                                                2346
```

<210> SEQ ID NO 6
<211> LENGTH: 2554
<212> TYPE: DNA
<213> ORGANISM: Homo sapiens

<400> SEQUENCE: 6

```
acaaggcagc ctcgctcgag cgcaggccaa tcggctttct agctagaggg tttaactcct      60
atttaaaaag aagaaccttt gaattctaac ggctgagctc ttggaagact tgggtccttg     120
ggtcgcaggt gggagccgac gggtgggtag accgtggggg atatctcagt ggcggacgag     180
gacggcgggg acaaggggcg gctggtcgga gtggcggagc gtcaagtccc ctgtcggttc     240
ctccgtccct gagtgtcctt ggcgctgcct tgtgcccgcc cagcgccttt gcatccgctc     300
ctgggcaccg aggcgccctg taggatactg cttgttactt attacagcta gagggtctca     360
ctccattgcc caggccagag tgcggggata tttgataaga aacttcagtg aaggccgggc     420
gcggtggctc atgcccgtaa tcccagcatt ttcggaggcc gaggctggag tgcaatggtg     480
tgatctcagc tcactgcaac ctctgcttcc tgggtttaag tgattctcct gcctcagcct     540
cccgagtagc tgggattaca ggcatcatgg accgatctaa agaaaactgc atttcaggac     600
ctgttaaggc tacagctcca gttggaggtc caaaacgtgt tctcgtgact cagcaatttc     660
cttgtcagaa tccattacct gtaaatagtg gccaggctca gcgggtcttg tgtccttcaa     720
attcttccca gcgcattcct ttgcaagcac aaaagcttgt ctccagtcac aagccggttc     780
agaatcagaa gcagaagcaa ttgcaggcaa ccagtgtacc tcatcctgtc tccaggccac     840
tgaataacac ccaaaagagc aagcagcccc tgccatcggc acctgaaaat aatcctgagg     900
aggaactggc atcaaaacag aaaaatgaag aatcaaaaaa gaggcagtgg gctttggaag     960
actttgaaat tggtcgccct ctgggtaaag gaaagtttgg taatgtttat ttggcaagag    1020
aaaagcaaag caagtttatt ctggctctta agtgttatt taaagctcag ctggagaaag    1080
ccggagtgga gcatcagctc agaagagaag tagaaataca gtcccacctt cggcatccta    1140
atattcttag actgtatggt tatttccatg atgctaccag agtctaccta attctggaat    1200
atgcaccact tggaacagtt tatagagaac ttcagaaact ttcaaagttt gatgagcaga    1260
gaactgctac ttatataaca gaattggcaa atgccctgtc ttactgtcat tcgaagagag    1320
ttattcatag agacattaag ccagagaact tacttcttgg atcagctgga gagcttaaaa    1380
ttgcagattt gggtggtca gtacatgctc catcttccag gaggaccact ctctgtggca    1440
ccctggacta cctgcccct gaaatgattg aaggtcggat gcatgatgag aaggtggatc    1500
tctggagcct tggagttctt tgctatgaat tttagttgg gaagcctcct tttgaggcaa    1560
acacatacca agagacctac aaaagaatat cacgggttga attcacattc cctgactttg    1620
taacagaggg agccagggac ctcatttcaa gactgttgaa gcataatccc agccagaggc    1680
caatgctcag agaagtactt gaacaccct ggatcacagc aaattcatca aaaccatcaa    1740
attgccaaaa caaagaatca gctagcaaac agtcttagga atcgtgcagg gggagaaatc    1800
cttgagccag ggctgccata taacctgaca ggaacatgct actgaagttt atttaccat    1860 tgactgctgc cctcaatcta gaacgctaca caagaaatat ttgttttact cagcaggtgt    1920
gccttaacct cccatattcag aaagctccac atcaataaac atgacactct gaagtgaaag    1980
```

| | |
|---|---:|
| tagccacgag aattgtgcta cttatactgg ttcataatct ggaggcaagg ttcgactgca | 2040 |
| gccgccccgt cagcctgtgc taggcatggt gtcttcacag gaggcaaatc cagagcctgg | 2100 |
| ctgtggggaa agtgaccact ctgccctgac cccgatcagt taaggagctg tgcaataacc | 2160 |
| ttcctagtac ctgagtgagt gtgtaactta ttggttggc gaagcctggt aaagctgttg | 2220 |
| gaatgagtat gtgattcttt ttaagtatga aaataaagat atatgtacag acttgtattt | 2280 |
| tttctctggt ggcattcctt taggaatgct gtgtgtctgt ccggcacccc ggtaggcctg | 2340 |
| attgggtttc tagtcctcct taaccactta tctcccatat gagagtgtga aaaataggaa | 2400 |
| cacgtgctct acctccattt agggatttgc ttgggataca aagaggcca tgtgtctcag | 2460 |
| agctgttaag ggcttatttt tttaaaacat tggagtcata gcatgtgtgt aaactttaaa | 2520 |
| tatgcaaata aataagtatc tatgtctaaa aaaa | 2554 |

<210> SEQ ID NO 7
<211> LENGTH: 2135
<212> TYPE: DNA
<213> ORGANISM: Homo sapiens

<400> SEQUENCE: 7

| | |
|---|---:|
| acaaggcagc ctcgctcgag cgcaggccaa tcggctttct agctagaggg tttaactcct | 60 |
| atttaaaaag aagaaccttt gaattctaac ggctgagctc ttggaagact tgggtccttg | 120 |
| ggtcgcaggt gggagccgac gggcatcatg gaccgatcta agaaaactg catttcagga | 180 |
| cctgttaagg ctacagctcc agttggaggt ccaaaacgtg ttctcgtgac tcagcaattt | 240 |
| ccttgtcaga atccattacc tgtaaatagt ggccaggctc agcgggtctt gtgtccttca | 300 |
| aattcttccc agcgcattcc tttgcaagca caaaagcttg tctccagtca caagccggtt | 360 |
| cagaatcaga agcagaagca attgcaggca accagtgtac ctcatcctgt ctccaggcca | 420 |
| ctgaataaca cccaaaagag caagcagccc ctgccatcgg cacctgaaaa taatcctgag | 480 |
| gaggaactgg catcaaaaca gaaaaatgaa gaatcaaaaa agaggcagtg ggctttggaa | 540 |
| gactttgaaa ttggtcgccc tctgggtaaa ggaaagtttg gtaatgttta tttggcaaga | 600 |
| gaaaagcaaa gcaagtttat tctggctctt aaagtgttat ttaaagctca gctggagaaa | 660 |
| gccggagtgg agcatcagct cagaagagaa gtagaaatac agtcccacct tcggcatcct | 720 |
| aatattctta gactgtatgg ttatttccat gatgctacca gagtctacct aattctggaa | 780 |
| tatgcaccac ttggaacagt ttatagagaa cttcagaaac tttcaaagtt tgatgagcag | 840 |
| agaactgcta cttatataac agaattggca atgcccctgt cttactgtca ttcgaagaga | 900 |
| gttattcata gagacattaa gccagagaac ttacttcttg gatcagctgg agagcttaaa | 960 |
| attgcagatt ttgggtggtc agtacatgct ccatcttcca ggaggaccac tctctgtggc | 1020 |
| accctggact acctgccccc tgaaatgatt gaaggtcgga tgcatgatga aaggtggat | 1080 |
| ctctggagcc ttggagttct ttgctatgaa ttttagttg ggaagcctcc ttttgaggca | 1140 |
| aacacatacc aagagaccta caaaagaata tcacggttg aattcacatt ccctgacttt | 1200 |
| gtaacagagg gagccaggga cctcatttca agactgttga agcataatcc cagccagagg | 1260 |
| ccaatgctca gagaagtact tgaacacccc tggatcacag caaattcatc aaaaccatca | 1320 |
| aattgccaaa acaagaatc agctagcaaa cagtcttagg aatcgtgcag ggggagaaat | 1380 |
| ccttgagcca gggctgccat ataacctgac aggaacatgc tactgaagtt tattttacca | 1440 |
| ttgactgctg ccctcaatct agaacgctac acaagaaata tttgttttac tcagcaggtg | 1500 |
| tgccttaacc tccctattca gaaagctcca catcaataaa catgacactc tgaagtgaaa | 1560 |

```
gtagccacga gaattgtgct acttatactg gttcataatc tggaggcaag gttcgactgc    1620
agccgccccg tcagcctgtg ctaggcatgg tgtcttcaca ggaggcaaat ccagagcctg    1680
gctgtgggga aagtgaccac tctgccctga ccccgatcag ttaaggagct gtgcaataac    1740
cttcctagta cctgagtgag tgtgtaactt attgggttgg cgaagcctgg taaagctgtt    1800
ggaatgagta tgtgattctt tttaagtatg aaaataaaga tatatgtaca gacttgtatt    1860
ttttctctgg tggcattcct ttaggaatgc tgtgtgtctg tccggcaccc cggtaggcct    1920
gattgggttt ctagtcctcc ttaaccactt atctcccata tgagagtgtg aaaaatagga    1980
acacgtgctc tacctccatt tagggatttg cttgggatac agaagaggcc atgtgtctca    2040
gagctgttaa gggcttattt ttttaaaaca ttggagtcat agcatgtgtg taaactttaa    2100
atatgcaaat aaataagtat ctatgtctaa aaaaa                              2135

<210> SEQ ID NO 8
<211> LENGTH: 2245
<212> TYPE: DNA
<213> ORGANISM: Homo sapiens

<400> SEQUENCE: 8
acaaggcagc ctcgctcgag cgcaggccaa tcggctttct agctagaggg tttaactcct      60
atttaaaaag aagaaccttt gaattctaac ggctgagctc ttggaagact tgggtccttg     120
ggtcgcaggt gggagccgac ggggtctcac tccattgccc aggccagagt gcggggatat     180
ttgataagaa acttcagtga aggccgggcg cggtggctca tgcccgtaat cccagcattt     240
tcggaggccg aggcatcatg gaccgatcta agaaaactg catttcagga cctgttaagg     300
ctacagctcc agttggaggt ccaaaacgtg ttctcgtgac tcagcaattt ccttgtcaga     360
atccattacc tgtaaatagt ggccaggctc agcgggtctt gtgtccttca aattcttccc     420
agcgcattcc tttgcaagca caaaagcttg tctccagtca caagccggtt cagaatcaga     480
agcagaagca attgcaggca accagtgtac ctcatcctgt ctccaggcca ctgaataaca     540
cccaaaagag caagcagccc ctgccatcgg cacctgaaaa taatcctgag gaggaactgg     600
catcaaaaca gaaaaatgaa gaatcaaaaa agaggcagtg ggctttggaa gactttgaaa     660
ttggtcgccc tctgggtaaa ggaaagtttg gtaatgttta tttggcaaga gaaaagcaaa     720
gcaagtttat tctggctctt aaagtgttat ttaaagctca gctggagaaa gccggagtgg     780
agcatcagct cagaagagaa gtagaaatac agtcccacct tcggcatcct aatattctta     840
gactgtatgt ttatttccat gatgctacca gagtctacct aattctgaa tatgcaccac     900 ttggaacagt ttatagagaa cttcagaaac tttcaaagtt tgatgagcag agaactgcta     960
cttatataac agaattggca aatgccctgt cttactgtca ttcgaagaga gttattcata    1020
gagacattaa gccagagaac ttacttcttg gatcagctgg agagcttaaa attgcagatt    1080
ttgggtggtc agtacatgct ccatcttcca ggaggaccac tctctgtggc acctggact     1140 acctgccccc tgaaatgatt gaaggtcgga tgcatgatga aaggtggat ctctggagcc    1200 ttggagttct ttgctatgaa tttttagttg ggaagcctcc ttttgaggca acacatacc     1260 aagagaccta caaaagaata tcacgggttg aattcacatt ccctgacttt gtaacagagg    1320
gagccaggga cctcatttca agactgttga agcataatcc cagccagagg ccaatgctca    1380
gagaagtact tgaacacccc tggatcacag caaattcatc aaaaccatca aattgccaaa    1440
acaaagaatc agctagcaaa cagtcttagg aatcgtgcag ggggagaaat ccttgagcca    1500
gggctgccat ataacctgac aggaacatgc tactgaagtt tatttaccca ttgactgctg    1560
```

-continued

| | |
|---|---|
| ccctcaatct agaacgctac acaagaaata tttgttttac tcagcaggtg tgccttaacc | 1620 |
| tccctattca gaaagctcca catcaataaa catgacactc tgaagtgaaa gtagccacga | 1680 |
| gaattgtgct acttatactg gttcataatc tggaggcaag gttcgactgc agccgccccg | 1740 |
| tcagcctgtg ctaggcatgg tgtcttcaca ggaggcaaat ccagagcctg gctgtgggga | 1800 |
| aagtgaccac tctgccctga ccccgatcag ttaaggagct gtgcaataac cttcctagta | 1860 |
| cctgagtgag tgtgtaactt attgggttgg cgaagcctgg taaagctgtt ggaatgagta | 1920 |
| tgtgattctt tttaagtatg aaaataaaga tatatgtaca gacttgtatt ttttctctgg | 1980 |
| tggcattcct ttaggaatgc tgtgtgtctg tccggcaccc cggtaggcct gattgggttt | 2040 |
| ctagtcctcc ttaaccactt atctcccata tgagagtgtg aaaaatagga acacgtgctc | 2100 |
| tacctccatt tagggatttg cttgggatac agaagaggcc atgtgtctca gagctgttaa | 2160 |
| gggcttattt ttttaaaaca ttggagtcat agcatgtgtg taaactttaa atatgcaaat | 2220 |
| aaataagtat ctatgtctaa aaaaa | 2245 |

<210> SEQ ID NO 9
<211> LENGTH: 2121
<212> TYPE: DNA
<213> ORGANISM: Homo sapiens

<400> SEQUENCE: 9

| | |
|---|---|
| acaaggcagc ctcgctcgag cgcaggccaa tcggctttct agctagaggg tttaactcct | 60 |
| atttaaaaag aagaaccttt gaattctaac ggctgagctc ttggaagact tgggtccttg | 120 |
| ggtcgcaggc atcatggacc gatctaaaga aaactgcatt tcaggacctg ttaaggctac | 180 |
| agctccagtt ggaggtccaa aacgtgttct cgtgactcag caatttcctt gtcagaatcc | 240 |
| attacctgta aatagtggcc aggctcagcg ggtcttgtgt ccttcaaatt cttcccagcg | 300 |
| cattcctttg caagcacaaa agcttgtctc cagtcacaag ccggttcaga atcagaagca | 360 |
| gaagcaattg caggcaacca gtgtacctca tcctgtctcc aggccactga ataacaccca | 420 |
| aaagagcaag cagcccctgc catcggcacc tgaaaataat cctgaggagg aactggcatc | 480 |
| aaaacagaaa aatgaagaat caaaaaagag gcagtgggct ttggaagact ttgaaattgg | 540 |
| tcgccctctg ggtaaaggaa agtttggtaa tgtttatttg gcaagagaaa agcaaagcaa | 600 |
| gtttattctg gctcttaaag tgtttattaa agctcagctg gagaaagccg gagtggagca | 660 |
| tcagctcaga agagaagtag aaatacagtc ccaccttcgg catcctaata ttcttagact | 720 |
| gtatggttat ttccatgatg ctaccagagt ctacctaatt ctggaatatg caccacttgg | 780 |
| aacagtttat agagaacttc agaaactttc aaagtttgat gagcagagaa ctgctactta | 840 |
| tataacagaa ttggcaaatg ccctgtctta ctgtcattcg aagagagtta ttcatagaga | 900 |
| cattaagcca gagaacttac ttcttggatc agctggagag cttaaaattg cagattttgg | 960 |
| gtggtcagta catgctccat cttccaggag gaccactctc tgtggcaccc tggactacct | 1020 |
| gcccccctgaa atgattgaag tcggatgca tgatgagaag gtggatctct ggagccttgg | 1080 |
| agttctttgc tatgaatttt tagttgggaa gcctcctttt gaggcaaaca cataccaaga | 1140 |
| gacctacaaa agaatatcac gggttgaatt cacattccct gactttgtaa cagagggagc | 1200 |
| cagggaccctc atttcaagac tgttgaagca taatcccagc cagaggccaa tgctcagaga | 1260 |
| agtacttgaa cacccctgga tcacagcaaa ttcatcaaaa ccatcaaatt gccaaaacaa | 1320 |
| agaatcagct agcaaacagt cttaggaatc gtgcaggggg agaaatcctt gagccagggc | 1380 |
| tgccatataa cctgacagga acatgctact gaagtttatt ttaccattga ctgctgccct | 1440 |

| | | | |
|---|---|---|---|
| caatctagaa | cgctacacaa | gaaatatttg | ttttactcag caggtgtgcc ttaacctccc | 1500 |
| tattcagaaa | gctccacatc | aataaacatg | acactctgaa gtgaaagtag ccacgagaat | 1560 |
| tgtgctactt | atactggttc | ataatctgga | ggcaaggttc gactgcagcc gccccgtcag | 1620 |
| cctgtgctag | gcatggtgtc | ttcacaggag | gcaaatccag agcctggctg tggggaaagt | 1680 |
| gaccactctg | ccctgacccc | gatcagttaa | ggagctgtgc aataaccttc ctagtacctg | 1740 |
| agtgagtgtg | taacttattg | ggttggcgaa | gcctggtaaa gctgttggaa tgagtatgtg | 1800 |
| attctttta | agtatgaaaa | taaagatata | tgtacagact tgtatttttt ctctggtggc | 1860 |
| attcctttag | gaatgctgtg | tgtctgtccg | gcaccccggt aggcctgatt gggtttctag | 1920 |
| tcctccttaa | ccacttatct | cccatatgag | agtgtgaaaa ataggaacac gtgctctacc | 1980 |
| tccatttagg | gatttgcttg | ggatacagaa | gaggccatgt gtctcagagc tgttaagggc | 2040 |
| ttatttttt | aaaacattgg | agtcatagca | tgtgtgtaaa cttaaaatat gcaaataaat | 2100 |
| aagtatctat | gtctaaaaaa | a | | 2121 |

<210> SEQ ID NO 10
<211> LENGTH: 2231
<212> TYPE: DNA
<213> ORGANISM: Homo sapiens

<400> SEQUENCE: 10

| | | | |
|---|---|---|---|
| acaaggcagc | ctcgctcgag | cgcaggccaa | tcggctttct agctagaggg tttaactcct | 60 |
| atttaaaaag | aagaaccttt | gaattctaac | ggctgagctc ttggaagact tgggtccttg | 120 |
| ggtcgcaggg | tctcactcca | ttgcccaggc | cagagtgcgg ggatatttga taagaaactt | 180 |
| cagtgaaggc | cgggcgcggt | ggctcatgcc | cgtaatccca gcattttcgg aggccgaggc | 240 |
| atcatggacc | gatctaaaga | aaactgcatt | tcaggacctg ttaaggctac agctccagtt | 300 |
| ggaggtccaa | aacgtgttct | cgtgactcag | caatttcctt gtcagaatcc attacctgta | 360 |
| aatagtggcc | aggctcagcg | ggtcttgtgt | ccttcaaatt cttcccagcg cattcctttg | 420 |
| caagcacaaa | agcttgtctc | cagtcacaag | ccggttcaga atcagaagca gaagcaattg | 480 |
| caggcaacca | gtgtacctca | tcctgtctcc | aggccactga ataacaccca aaagagcaag | 540 |
| cagcccctgc | catcggcacc | tgaaaataat | cctgaggagg aactggcatc aaaacagaaa | 600 |
| aatgaagaat | caaaaagag | gcagtgggct | ttggaagact tgaaattgg tcgccctctg | 660 |
| ggtaaaggaa | agtttggtaa | tgtttatttg | gcaagagaaa agcaaagcaa gtttattctg | 720 |
| gctcttaaag | tgttatttaa | agctcagctg | gagaaagccg gagtggagca tcagctcaga | 780 |
| agagaagtag | aaatacagtc | ccaccttcgg | catcctaata ttcttagact gtatggttat | 840 |
| ttccatgatg | ctaccagagt | ctacctaatt | ctggaatatg caccacttgg aacagtttat | 900 |
| agagaacttc | agaaactttc | aaagtttgat | gagcagagaa ctgctactta tataacagaa | 960 |
| ttggcaaatg | ccctgtctta | ctgtcattcg | aagagagtta ttcatagaga cattaagcca | 1020 |
| gagaacttac | ttcttggatc | agctggagag | cttaaaattg cagattttgg gtggtcagta | 1080 |
| catgctccat | cttccaggag | gaccactctc | tgtggcaccc tggactacct gcccctgaa | 1140 |
| atgattgaag | gtcggatgca | tgatgagaag | gtggatctct ggagccttgg agttctttgc | 1200 |
| tatgaatttt | tagttgggaa | gcctccttt | gaggcaaaca cataccaaga gacctacaaa | 1260 |
| agaatatcac | gggttgaatt | cacattccct | gactttgtaa cagagggagc cagggacctc | 1320 |
| atttcaagac | tgttgaagca | taatcccagc | cagaggccaa tgctcagaga agtacttgaa | 1380 |
| caccctgga | tcacagcaaa | ttcatcaaaa | ccatcaaatt gccaaaacaa agaatcagct | 1440 |

```
agcaaacagt cttaggaatc gtgcagggggg agaaatcctt gagccagggc tgccatataa    1500
cctgacagga acatgctact gaagtttatt ttaccattga ctgctgccct caatctagaa    1560
cgctacacaa gaaatatttg ttttactcag caggtgtgcc ttaacctccc tattcagaaa    1620
gctccacatc aataaacatg acactctgaa gtgaaagtag ccacgagaat tgtgctactt    1680
atactggttc ataatctgga ggcaaggttc gactgcagcc gccccgtcag cctgtgctag    1740
gcatggtgtc ttcacaggag gcaaatccag agcctggctg tggggaaagt gaccactctg    1800
ccctgacccc gatcagttaa ggagctgtgc aataaccttc ctagtacctg agtgagtgtg    1860
taacttattg ggttggcgaa gcctggtaaa gctgttggaa tgagtatgtg attcttttta    1920
agtatgaaaa taaagatata tgtacagact tgtattttttt ctctggtggc attcctttag    1980
gaatgctgtg tgtctgtccg gcaccccggt aggcctgatt gggtttctag tcctccttaa    2040
ccacttatct cccatatgag agtgtgaaaa ataggaacac gtgctctacc tccatttagg    2100
gatttgcttg ggatacagaa gaggccatgt gtctcagagc tgttaagggc ttatttttt     2160 aaaacattgg agtcatagca tgtgtgtaaa ctttaaatat gcaaataaat aagtatctat    2220
gtctaaaaaa a                                                         2231

<210> SEQ ID NO 11
<211> LENGTH: 4147
<212> TYPE: DNA
<213> ORGANISM: Homo sapiens

<400> SEQUENCE: 11
cggcgcgcga cgtgctttgc tgtataaatg cggtggcgcc cggcgtaggg acacttcggt      60
cctgagcgct tgggagttag gttgtttgcc ggcgtagcgg ccagcgcctg agcccgccct     120
tgatcttcgc tgtggcatgg cggacgaggg gaagtcgtac agcgaacacg atgatgaacg     180
cgttaatttc cctcaaagaa agaagaaagg ccggggtccc ttccggtgga atatgggtga     240
aggaaaccgt aggtctggaa gaggcggttc tggtattcgg tcttcccgcc ttgaggaaga     300
tgatggagat gtggcaatga gtgatgccca ggatggtccc cgagtacgat acaacccta     360 taccacccga cctaaccgtc ggggtgatac ttggcatgat cgagatcgca ttcatgttac     420
tgtgcggaga gacagagctc ctccagagag aggaggggct ggcaccagcc aggatgggac     480
ctcaaagaac tggttcaaga ttacaattcc ttatggcaga aagtatgaca aggcatggct     540
cctgagcatg attcagagca agtgcagtgt gcccttcacc cctattgagt ttcactatga     600
gaatacacgg gcccagttct tcgttgaaga cgccagtact gcctctgcat gaaggctgt     660 caactataag atttttggatc gggagaaccg aaggatatct atcatcatca actcttctgc     720
tccaccccac actatactga atgaactgaa gccagaacaa gtagaacagc taaagctgat     780
catgagcaaa cgatacgatg gctcccaaca agcccttgac ctcaaaggcc tccgttcaga     840
cccagatttg gtggcccaga acattgacgt tgtcctgaat cgcagaagct gtatggcagc     900
taccctgagg atcattgaag agaacatccc tgagctattg tccttgaact tgagcaacaa     960
caggctgtac aggctggatg acatgtctag cattgttcag aaggcaccca acctgaagat    1020
cctaaacctt tctggaaatg aattgaagtc tgagcgggaa ttggacaaga taaagggggct    1080 gaagctagaa gagctctggc tcgatggaaa ctccctgtgt gacaccttcc gagaccagtc    1140
cacctacatc aggtcagttg tagcctgtgt ctcccctcct ggggaccttc accccctggg    1200
aggctgagct aatgcatcct gaccagggcc gtctgcgga gatgtgcagc cctgagctgg    1260
aaccacctgt cctttgagag gatcgcgtgc tccccacttt ggtctgtctg tgtcttccag    1320
```

```
ctttgtcctg agatgttctc tcttctcttc tgacttgact atctgtttgc tgggtctgtg    1380
gcctttctct ttcttcctga acacaacctt ttctagaatc tccctaccct gttgttccag    1440
gaaaggcatc tcccctttct actctaacca gagggtatct tgtacatacc ctatagatgg    1500
ggttgccttg tgccaagagc ctggtgtcca tgggttgagg aagccctccc tacctgggac    1560
ttcctactga gatgggcctt ccctcctttg tactgtgatg gcccctcttg cccttgcgcc    1620
aagagggacc cttttctcag gatccacttg cccaggctg ttgctgtcca tgctgaggtt    1680
gaggcctcct aggggctggt ggcatgcaat ctgtctctct tgcccagtgc tatgagctgg    1740
gctctccctg aagaagaaac ctgggttccc caagatgtga ccagagctgg ggccccgcca    1800
gcaggcgagg gaatcccaag gcaggtgctg ggcgtggagg ccacgggggc ataggctacc    1860
aaggagacag agaactgacc ccctcggggg cgctgcctct ccctcactca cacactgcac    1920
gtcaccctgt ttggccccgg tggatggctg gttagccaga gacgggtaag attcctcagg    1980
gaaggaacaa cctaagacag gcacagtcgc agaggggcca tcaggagaga acttgggggc    2040
aacagaggtg gggcatggac cctcaccccc acaatcctac aggggcctga accctcacac    2100
cttctgaggg aggtctcctg cccccatggc tgctttgctt cccacgccca gttcagatcg    2160
ggacccaggt agcagacaga gacctggcca acagcaagtg cccactcacc acagcaagga    2220
tttgtttctc atttctacct tggaccacag ggatggggca gctgaaagaa agggctgtgt    2280
cagggtgtct ttctcccttt tctccctcat ttttctagat gctttttgc cttgtagttc    2340
tttctctttt tctttgcttt ctctttcctt tttctgtctg tctcctatac ctccccatct    2400
ctcccttgcc cctgccccat cttgccttt tctcttttc ctccttttcc tttcttattc    2460
ctttgcctct cctcttcctg agccccacct gctcatctcc ctgccccaac atcctgtgcc    2520
atccctgtgg tgtgtttggg tcttggccaa agccagacct ggcagaactg atggatacct    2580
ggtgaggcag cggagcccct gggctcccac cccattccct cctcccgggg ctgcacaggt    2640
gagtaggtgg aaggtaaggg gggcagggag gggaaagagg tcctgggctt aaagcctggg    2700
cttggagtac tgctccttga cactcagggt caggcagaga gaaaagagac agccttcaag    2760
gcagtccatg tctgggtgcc ccgggtcagg tgggagtgg gggccatttt tccctgagca    2820
caggctggga gggagtggag ggatgagcag gatgggatgg gctgtccctc gggtttggta    2880
tatttgctcc tagagcagcc caggaggcac ggtggctctg aagcatcact cacttctgtc    2940
ccgttcttga cagcgccatt cgcgaacgat ttcccaagtt actacgcctg gatggccatg    3000
agctacccc accaattgcc tttgatgttg aagcccccac gacgttaccg ccctgcaagg    3060
gaagctattt tggaacagaa acttgaaga gtctggtctt gcacttcctg caacagtact    3120
atgcaattta cgactctgga gaccgacaag ggctcctgga tgcctaccat gatgggcct    3180
gctgttccct gagcattcct ttcattcctc agaaccctgc ccgaagcagc ttagccgagt    3240
atttcaagga tagcagaaat gtgaagaagc ttaaagaccc tacctttgcgg ttccggctgc    3300
tgaagcacac gcgtctcaac gttgttgcct tcctcaatga gttgcccaaa acccagcacg    3360
acgtcaattc cttcgtggta gacataagcg cccagacaag cacattgctg tgttttctg    3420
tcaatggagt cttcaaggaa gtggacggaa agtcccggga ttctttgcga gccttcaccc    3480
ggacattcat tgctgttcct gctagcaatt cagggctatg tattgtaaat gatgagctat    3540
ttgtgcggaa tgccagttct gaagagatcc aaagagcctt cgctatgcct gcacccacgc    3600
cttcctccag cccggtgccc accctctctc cagagcagca ggaaatgttg caagcattct    3660
ctacccagtc tggcatgaac ctcgagtggt cccagaagtg ccttcaggac aacaactggg    3720
```

| | | | | |
|---|---|---|---|---|
| actacaccag | atctgcccag | gccttcactc | atctcaaggc | caagggcgag atcccagaag | 3780 |
| tggcattcat | gaagtgatcg | tagtcatgcc | tcagaagcag | tccccctgt aaatagtcct | 3840 |
| tggatattac | cgtctggttg | tcgtctgtca | tctcctcctg | tctggcccga ggccgccccg | 3900 |
| tgactgtgac | cgagggaggg | agggctgcct | gatccctctc | ctcgcctgcc ttctggaaga | 3960 |
| cttcagaaga | ttgagcctca | ctggtgccag | gaagccaaag | cttactttgt agaactgaca | 4020 |
| ctaaactacc | cgaaggactt | aggtgctttg | tgtacttaac | cccaggacct ccttactttt | 4080 |
| taatataaag | agtgatgttg | tatttcgtgt | tctgcacttt | ttaatataaa gagtgatgtt | 4140 |
| gtatttc | | | | | 4147 |

```
<210> SEQ ID NO 12
<211> LENGTH: 2346
<212> TYPE: DNA
<213> ORGANISM: Homo sapiens

<400> SEQUENCE: 12
```

| | | | | | |
|---|---|---|---|---|---|
| cggcgcgcga | cgtgctttgc | tgtataaatg | cggtggcgcc | cggcgtaggg acacttcggt | 60 |
| cctgagcgct | tgggagttag | gttgtttgcc | ggcgtagcgg | ccagcgcctg agcccgccct | 120 |
| tgatcttcgc | tgtggcatgg | cggacgaggg | gaagtcgtac | agcgaacacg atgatgaacg | 180 |
| cgttaatttc | cctcaaagaa | agaagaaagg | ccggggtccc | ttccggtgga atatggtga | 240 |
| aggaaaccgt | aggtctggaa | gaggcggttc | tggtattcgg | tcttcccgcc ttgaggaaga | 300 |
| tgatggagat | gtggcaatga | gtgatgccca | ggatggtccc | cgagtacgat acaacccta | 360 |
| taccacccga | cctaaccgtc | ggggtgatac | ttggcatgat | cgagatcgca ttcatgttac | 420 |
| tgtgcggaga | gacagagctc | ctccagagag | aggagggct | ggcaccagcc aggatgggac | 480 |
| ctcaaagaac | tggttcaaga | ttacaattcc | ttatggcaga | aagtatgaca aggcatggct | 540 |
| cctgagcatg | attcagagca | agtgcagtgt | gcccttcacc | cctattgagt ttcactatga | 600 |
| gaatacacgg | gcccagttct | tcgttgaaga | cgccagtact | gcctctgcat gaaggctgt | 660 |
| caactataag | attttggatc | gggagaaccg | aaggatatct | atcatcatca actcttctgc | 720 |
| tccaccccac | actatactga | atgaactgaa | gccagaacaa | gtagaacagc taaagctgat | 780 |
| catgagcaaa | cgatacgatg | gctcccaaca | agcccttgac | ctcaaaggcc tccgttcaga | 840 |
| cccagatttg | gtggcccaga | acattgacgt | tgtcctgaat | cgcagaagct gtatggcagc | 900 |
| taccctgagg | atcattgaag | agaacatccc | tgagctattg | tccttgaact tgagcaacaa | 960 |
| caggctgtac | aggctggatg | acatgtctag | cattgttcag | aaggcaccca acctgaagat | 1020 |
| cctaaacctt | tctggaaatg | aattgaagtc | tgagcgggaa | ttggacaaga taaaggggct | 1080 |
| gaagctagaa | gagctctggc | tcgatggaaa | ctccctgtgt | gacaccttcc gagaccagtc | 1140 |
| cacctacatc | agcgccattc | gcgaacgatt | tcccaagtta | ctacgcctgg atggccatga | 1200 |
| gctacccca | ccaattgcct | ttgatgttga | agccccacg | acgttaccgc cctgcaaggg | 1260 |
| aagctatttt | ggaacagaaa | acttgaagag | tctggtcttg | cacttcctgc aacagtacta | 1320 |
| tgcaatttac | gactctggag | accgacaagg | gctcctggat | gcctaccatg atggggcctg | 1380 |
| ctgttccctg | agcattcctt | tcattcctca | gaaccctgcc | cgaagcagct tagccgagta | 1440 |
| tttcaaggat | agcagaaatg | tgaagaagct | taaagaccct | accttgcggt tccggctgct | 1500 |
| gaagcacacg | cgtctcaacg | ttgttgcctt | cctcaatgag | ttgcccaaaa cccagcacga | 1560 |
| cgtcaattcc | ttcgtggtag | acataagcgc | ccagacaagc | acattgctgt gttttttctgt | 1620 |
| caatggagtc | ttcaaggaag | tggacggaaa | gtcccgggat | tctttgcgag ccttcacccg | 1680 |

```
gacattcatt gctgttcctg ctagcaattc agggctatgt attgtaaatg atgagctatt    1740
tgtgcggaat gccagttctg aagagatcca aagagccttc gctatgcctg cacccacgcc    1800
ttcctccagc ccggtgccca ccctctctcc agagcagcag gaaatgttgc aagcattctc    1860
tacccagtct ggcatgaacc tcgagtggtc ccagaagtgc cttcaggaca caactgggaa    1920
ctacaccaga tctgcccagg ccttcactca tctcaaggcc aagggcgaga tcccagaagt    1980
ggcattcatg aagtgatcgt agtcatgcct cagaagcagt cccccctgta aatagtcctt    2040
ggatattacc gtctggttgt cgtctgtcat ctcctcctgt ctggcccgag gccgcccgt     2100 gactgtgacc gagggaggga gggctgcctg atccctctcc tcgcctgcct tctggaagac    2160
ttcagaagat tgagcctcac tggtgccagg aagccaaagc ttactttgta gaactgacac    2220
taaactaccc gaaggactta ggtgctttgt gtacttaacc ccaggacctc cttactttt     2280 aatataaaga gtgatgttgt atttcgtgtt ctgcactttt aatataaag agtgatgttg     2340 tatttc                                                              2346

<210> SEQ ID NO 13
<211> LENGTH: 2352
<212> TYPE: DNA
<213> ORGANISM: Homo sapiens

<400> SEQUENCE: 13
ccagaatgag atacagccaa tttggctttg atgacccagc tgagagggaa atttagatac      60
aattcaggaa tatcatgccc aaaaatagtg gtcccagcaa ccaggacaca gagggaagac     120
ctggatattg tcagtgattg gtggaggggg acatcttgga ccctcctagg cctggtgtca     180
catctcccat ctctcagacc ccacagaggc caagggggcct tggctctgac ccaggttaaa    240
gagagccacc agcccccagg ctcagggagc tgaaaccacc catccgcaga aatctaaggg    300
caaggagaaa tagaaattgt ctgttccttc ccttcaaagt gtaaggcctc ttccaggagc    360
aactggagcc accacagctt ctcagtgaca ttggagggc ttcgggccca ggaaaaaccc     420
aagccttttg tcctgagagc cgagccacag cggatgcagt ggcgtcagca tcccagagcg    480
gcagcttctc tcctgcctgt cactggggac tggttgctct ccacccatcc aggaggaagg    540
ggttaggtcc cagtcttaca ctcttatagg gtctcatgga cataggccta tgcctgttct    600
gatatctata attttttaaa ctcaaaagga ccaaaacact cctgaaccct catctatacg    660
gcctgcactg ggcttggtgt ttcctcctgg cccaggcagc tccatctctt ctgccattcc    720
tcctggacga aagtggcagg accccacctc taccacttcc ccacagggtc actgcacagc    780
ggcttcaaag acacgccctg ttgaagggga acatcctcc ccccatcaca ctccaactcg     840
tcaccccaaa agggaagtca aagcacaggt ccgtggggcc tatggtttgt agacactgac    900
acagtggttt tcaaaccagg tgctgcggaa cccctgatat tccacagagc tttgtcaggg    960
gatgctaaag tgggaagatg ggagtggagg caaaggatag gtttccagcc ctcctcccat   1020
ttccgccgcc accagaataa ctctgctttt atctgtcttg cctactgaga tttcatttc    1080 aagctttctt tgaagaagaa cttcaaacca ccatctcgag gtttgatctt agaccagcca    1140
gcacaggttc tattcttgct gttcatgttg gaatggctcc agcgttccag tacaaagtgt   1200
ctttgtgttg gaacttgggt cacagaccca ggcacaagca tttatacaca cacacacaca   1260
cacacacaca cacacacaca cacgtacata gttgatggtt tttctagcca acccaccctg   1320
aagctctggc caaggtttga tttggacagg gacctggtgc tcagtgggga tgggtcgtga   1380
ccctgatatt ggcccatgaa gcatggggag ctctggagca aggaaacagg ctcaatcccc   1440
```

```
cactgaggac ttgtgtctgc accectatct ggcacccccac tttcctggcc taggcccaag    1500
ggacacagca ggagaagcag tgtgatagga gagaggctag ggttaaattc atctttacac    1560
agcgccggat ggatggaaat cttggctcac ataaaagaca gactcaggga ggattttatg    1620
acaaaagtcc ctcctttgag ggcaggattc ccccaggaat cctggacact ttagtgagaa    1680
ctggaccagc ccttggcaca aaaccctgcc tgccctgtcc cccactccca ccccccaggg    1740
aattctaggt gaaaatgtga agctcagggc acagcaagcg catgacacgg gtgtattaca    1800
ttcggtccga gtgtgtcctt agtttccctg tgtgcaaaat ggggctagtc caggctcttc    1860
ccacctcact gggacaattg caagggtcat aggagaggtg ggtatgatag gtggtcatat    1920
gaggtggtga gtatgagagg tgggtgcctc acaaactcgg ggtatggtcc tgacctgcat    1980
ggcagatgag cagagcactt gggaacgagc ataggaagtg ccatcttccc gggcatctct    2040
gctcagtgtt aaggtctagc cacagacact gtgggacctg cctcttccta tggaatgggg    2100
gcctgcatgg gttgtgtcct ggggcaggag tgagggatgg ctgggaagaa tctccaggtc    2160
tgtggccctt gtgttgagtg attattttgt gacactctca ttcctggacc acctgccagg    2220
tttatctgtt ataccgtgg cattcttatt atgtcagaca agttattata gttcattcaa     2280
ctctaacaaa tgaacaaaag aacaataaat aggaggccat taaaggtctt ttgtggaaaa    2340
aaaaaaaaaa aa                                                         2352

<210> SEQ ID NO 14
<211> LENGTH: 2663
<212> TYPE: DNA
<213> ORGANISM: Homo sapiens

<400> SEQUENCE: 14
ggcggtttcc atggtgacgg caaacaaggc ccacactgga cagggcagct gctgggttgc      60
tactctcgcc tccgccatga ttccgcccgc agactctttg ctcaagtacg acaccccagt    120
gctggtgagc cggaacacgg agaaacggag cccccaaggct cggctactga agtcagccc    180 ccagcagcct ggaccttcag gttcagcccc acagccaccc aagaccaagc tcccctcaac    240
tccctgtgtc ccagatccta caaagcaggc agaagaaatc ttgaatgcca tactacccc    300 aagggagtgg gtggaagaca cgcagctatg gatccagcag gtgtccagca cccctagcac    360
caggatggac gtggtgcacc tccaggagca gttagactta aagctgcagc agcggcaggc    420
cagggaaaca ggcatctgcc ctgtccgcag ggaactctac tcacagtgtt ttgatgagtt    480
gatccgggag gtcaccatca actgtgcgga gaggggggctg ctgctgctgc gagtccggga    540
cgagatccgc atgaccatcg ctgcctacca gaccctgtac agagcagcg tggcgtttgg    600 catgaggaag gcactgcagg ctgagcaggg gaagtcagac atggagagga aaatcgcaga    660
attggagacg gaaaagagag acctggagag gcaagtgaac gagcagaagg caaaatgtga    720
agccactgag aagcgggaga gcgagaggcg caggtggagg agaagaagc acaatgagga    780 gattcagttc ctgaagcgaa caaatcagca gctgaaggcc caactggaag gcattattgc    840
accaaagaag tgataatttc cacatgatta atttccaaca agacacttgg gagttattta    900
ctgtgttcct ctggcagcca ataaaatcat cataagccct ttgtaataaa aagctagttt    960
cctgagtgaa caagccataa cctccccctaa acaccaccta ggtatttgtt agaagtcaca   1020
ctattactcc aatgtcatca gacacctaag gtctgccagc caggctcctg gctgggcaat   1080
ggaagatggt gtggccctgt tagtctccgt gtgtggctta ctagccagcc ttgggaactg   1140
ccaactcaaa ttctaagaaa gccactgctt tctcatcatc actctatacc aatacttatt   1200
```

```
tctggccaaa tgaatctgct tctctgcccc tcaaactttt agttcacaat tcatcttcta    1260
ccttaacttg ggcttcttgg gcctctggcc ttccttactt aatgtcttct tttccctact    1320
ctaatgcatt tctaactcac tttggagctt tggttttcta atgtattatc cccacttgcc    1380
agtcaactgg acccctttcct cctcggtttc agactgccta cattaggaaa caatggcagt   1440
caaacccatg gctttggaga aagtaaatgt tgccagaaa ggaatactag tcacagtggc     1500
ctttgtgagt tgtctgcaac tcagctcttc ccccagcaca gatctgttcc ccttatcctg    1560
cagaaaatca gccctgact ctgcactccc cgaagtagtg atgttaatta caactgaag      1620 aggtaactaa atctcacatg caggtctaat gactaataat tggagtacgg ctgctagaca    1680
actgcatttt agtatttctc ttccattctc ctggttttgt agacccagaa gattgaatga    1740
gtgacataaa tctttagttc ggggcaagcc agggtgggct agggtggtaa gctggaggac    1800
ttcatccttc agttaggctg cacaagtaac attacctaaa aggcactaac atgctcaggt    1860
tccccagaaa gaggcgtaag aagggcctct ccttagcaga gcttccacct gccatccgtc    1920
ttgggttcag tgagcttcaa ggctcacaat ggaagcactg tcatttcccc agaaaagctg    1980
tgttccctat gctgaacaca ccatacacat tctcatctgg aatctaagga gcagcttta    2040 ccctgatcca gtatcctgag gaattttaag cctccactca aatgacctgc ctgtgttgtc    2100
atttccatgg gaaagaactc tttccacgag atctgctagt tccaggcctc taagacagga    2160
acgtatgtgc cataagtggg tctacttcac agactcaatg aggcagaaat tattgtagtt    2220
ttctcctatt tcttctgcac ccaactttct ccttgtattt caaaggccag gccatgtaca    2280
ctaacgtcct tgaaatttgc agttctgtat gcttctattc caaatcattc attaccaata    2340
aaaacgaaat accaccctttt ccattttata gacctcatcc cctatttctg tcagacagtt   2400
atatgacagg gtgactgtgg aacctcttag ttcatccaaa gtctacctga agtgctagac    2460
tttcagactc ttatcactga aatccttaag gttgaggagg cttttatttcc ctagcactgg   2520 tgaagggctt caactgtcaa acctcagaac aaatgcatta gggccttaga aatgtcaatg    2580
gggcaggaag aaaacacaat ttctaactgc ctgttttgt ataatttaat aaaaaccttt     2640
taaacattaa aaaaaaaaaa aaa                                            2663

<210> SEQ ID NO 15
<211> LENGTH: 5507
<212> TYPE: DNA
<213> ORGANISM: Homo sapiens

<400> SEQUENCE: 15
gcggccgcgg gctctcgcgg ggcggcgacg ccgcggggag gatgctgctt gccgcgcccg      60
cgtcctcacc gtcctcccgg gccgcctgct ggggctttgt tgtggcccgg acgccgcggg     120 ccacccctg aagtcgcctg ccgccgccgc cgccgcacct agcggacggg cgggcgggcg      180
cgcgtgtgcc caggagtgcg cgcctgtcgc ggtggtgggt gcaggactgg acccacgggc    240
ccattgtgcg cccgcccgcg gcagccagga ccatgtgggt gaacccggag gaggtgttgc    300
tggccaacgc gctgtggatc accgagaggg ccaacccata cttcatcctg cagcggagga    360
agggccacgc cggcgatgga ggcggcggcg gcggactggc gggcctgctg gtgggtaccc    420
ttgatgttgt gttggactcc agcgcccggg tcgctcctta ccgaatcttg taccagactc    480
cagactccct ggtctactgg accatcgcct gtggtggttc caggaaagaa atcactgaac    540
actgggaatg gcttgagcaa aatctcttgc agacactctc catctttgaa aatgagaatg    600
atatcaccac atttgtgaga ggaaaaatac agggcatcat tgcagaatac aacaaaatca    660
```

```
atgatgtaaa ggaagatgat gacacggaga agtttaaaga agccattgtg aaatttcata    720
ggctgtttgg gatgccagag gaagagaaac tcgtcaacta ttactcttgc agctattgga    780
aggggaaggt cccccgtcag ggttggatgt acctcagcat taaccacctt tgcttttatt    840
cttttcttat gggaagggaa gcgaaactgg tcatccggtg ggtagacatc actcagcttg    900
agaagaatgc caccctgctt ctgcctgatg tgatcaaagt gagcacacgg tccagtgagc    960
atttcttctc tgtattcctc aacatcaacg agaccttcaa gttaatggag cagcttgcca   1020
acatagccat gaggcaactc ttagacaatg agggatttga acaagatcga tccctgccca   1080
aactcaaaag gaaatctcct aaaaaagtgt ctgctctaaa acgtgatctt gatgccaggg   1140
caaagagtga gagataccgt gcacttttcc ggctgcccaa agatgaaaaa ttagatggcc   1200
acacagactg cactctctgg actccattta acaaaatgca cattttgggg cagatgtttg   1260
tgtccacaaa ttacatctgt tttaccagca aggaggagaa cttatgtagc ctcattatcc   1320
cgctccgtga ggtgacaatt gtggaaaagg cagacagctc cagtgtgctc cccagtccct   1380
tatccatcag cacccgaaac aggatgacct tcctatttgc caacttgaaa gatagagact   1440
ttctagtgca gaggatctca gatttcctgc aacagactac ttccaaaata tattctgaca   1500
aggagtttgc aggaagttac aacagttcag atgatgaggt gtactctcga cccagcagcc   1560
tcgtctcctc cagcccccag agaagcacga gctctgatgc tgatggagag cgccagttta   1620
acctaaatgg caacagcgtc cccacagcca cacagaccct gatgaccatg tatcggcggc   1680
ggtctcccga ggagttcaac ccgaaattgc caaagagtt tctgaaagag caagcctgga   1740
agattcactt tgctgagtat gggcaaggga tctgcatgta ccgcacagag aaaacgcggg   1800
agctggtgtt gaagggcatc ccggagagca tgcgtgggga gctctggctg ctgctgtcag   1860
gtgccatcaa tgagaaggcc acacatcctg ggtactatga agacctagtg gagaagtcca   1920
tggggaagta taatctcgcc acggaggaga ttgagaggga tttacaccgc tcccttccag   1980
aacacccagc ttttcagaat gaaatgggca ttgctgcact aaggagagtc ttaacagctt   2040
atgcttttcg aaatcccaac atagggtatt gccaggccat gaatattgtc acttcagtgc   2100
tgctgcttta tgccaaagag gaggaagctt tctggctgct tgtggctttg tgtgagcgca   2160
tgctcccaga ttactacaac accagagttg tgggtgcact ggtggaccaa ggtgtctttg   2220
aggagctagc acgagactac gtcccacagc tgtacgactg catgcaagac tgggcgtga   2280
tttccaccat ctccctgtct tggttcctca cactatttct cagtgtgatg ccttttgaga   2340
gtgcagttgt ggttgttgac tgtttcttct atgaaggaat taaagtgata ttccagttgg   2400
ccctagctgt gctggatgca aatgtggaca aactgttgaa ctgcaaggat gatggggagg   2460
ccatgaccgt tttgggaagg tatttagaca gtgtgaccaa taaagacagc acactgcctc   2520
ccattcctca cctccactcc ttgctcagcg atgatgtgga accttaccct gaggtagaca   2580
tctttagact catcagaact tcctacgaga aattcggaac tatccgggca gatttgattg   2640
aacagatgag attcaaacag agactgaaag tgatccagac gctggaggat actacgaaac   2700
gcaacgtggt acgaaccatt gtgacagaaa cttcctttac cattgatgag ctggaagaac   2760
tttatgctct tttcaaggca gaacatctca ccagctgcta ctgggcggg agcagcaacg   2820
cgctggaccg gcatgacccc agcctgccct acctggaaca gtatcgcatt gacttcgagc   2880
agttcaaggg aatgtttgct cttctctttc cttgggcatg tggaactcac tctgacgttc   2940
tggcctcccg cttgttccag ttattagatg aaaatggaga ctctttgatt aacttccggg   3000
agtttgtctc tgggctaagt gctgcatgcc atggggacct cacagagaag ctcaaactcc   3060
```

```
tgtacaaaat gcacgtcttg cctgagccat cctctgatca agatgaacca gattctgctt    3120
ttgaagcaac tcagtacttc tttgaagata ttaccccaga atgtacacat gttgttggat    3180
tggatagcag aagcaaacag ggtgcagatg atggctttgt tacggtgagc ctaaagccag    3240
acaaagggaa gagagcaaat tcccaagaaa atcgtaatta tttgagactg tggactccag    3300
aaaataaatc taagtcaaag aatgcaaagg atttacccaa attaaatcag ggcagttca    3360 ttgaactgtg taagacaatg tataacatgt tcagcgaaga ccccaatgag caggagctgt    3420
accacgccac ggcagcagtg accagcctcc tgctggagat tggggaggtc ggcaagttgt    3480
tcgtggccca gcctgcaaag gagggcggga gcggaggcag tgggccgtcc tgccaccagg    3540
gcatcccagg cgtgctcttc cccaagaaag ggccaggcca gccttacgtg gtggagtctg    3600
ttgagcccct gccggccagc ctggcccccg acagcgagga cactcccctt ggaggacaaa    3660
tggaggacat caagctggag gactcctcgc cccgggacaa cggggcctgc tcctccatgc    3720
tgatctctga cgacgacacc aaggacgaca gctccatgtc ctcatactcg gtgctgagtg    3780
ccggctccca cgaggaggac aagctgcact gcgaggacat cggagaggac acggtcctgg    3840
tgcggagcgg ccagggcacg gcggcactgc cccggagcac cagcctggac cgggactggg    3900
ccatcacctt cgagcagttc ctggcctccc tcttaactga gcctgccctg gtcaagtact    3960
ttgacaagcc cgtgtgcatg atggccagga ttaccagtgc aaaaaacatc cggatgatgg    4020
gcaagcccct cacctcggcc agtgactatg aaatctcggc catgtccggc tgacacgggc    4080
gccttcccgg gggagtggga ggagagggag gggagggatt ttttatgttc ttctgtgttg    4140
agttttttct ttctttcttt taaattaaat atttattagt acctggcttg aagcctagtg    4200
ttttcataat gtaattcaat gaaaactgtt ggagaaatat ttaaacacct caatgtaggt    4260
acattacact cttgttgcgg ggagggatt taccagaata cagtttattt cgtgaattct    4320
aaaaaacaaa aagatgaatc tgtcagtgat atgtgtgtat tataacttat taatcttgct    4380
gttgagctgt atacatggtt taaaaaatag tactgtttaa tgctaagtaa ggcagcagtc    4440
atttgtgtat tcaggctttt taaataaaat tagagctgta aggaaaatga aaagccacaa    4500
atgcaagact gttcttaaat ggaaggcata gtcagcgagg gtaaatccta taccacttta    4560
ggaagtatta aaaatatttt taagatttga aatatatttc atagaagtcc tctattcaaa    4620
atcatattcc acagatgttc cccttcaaag ggaaaacatt tggggttcta aacagttatg    4680
aaagtaagtg atttttacat gattccagaa taacacttgt attgaccaat ttagacagat    4740
accagaccaa ttttgcattt aagaaattgt tctgattatt tacgtcaact cattagaatt    4800
cagtgaaaag taacagtctt ttgtcacaga gaatctgaaa gtagcagcaa agacagaggg    4860
ctcatgcacg gtttttgctt ttgctttgct tttgttttg aaagagtaaa agtactgatg    4920
cttctgatac tggatgttta gcttcttact gcaaaaacat aagtaaaaca gtcaacttta    4980
ccatttccgt attctccata gattgaagaa atttatacca catatcgcat atgaccatct    5040
ttccatcaaa tcaatgtaga gataatgtaa actgaaaaaa aatctgcaag ataatgtaac    5100
tgaatgtttt aaaaacagaa cttgtcactt tatataaaag aatagtatgc tctatttcct    5160
gaatggatgt ggaaatgaaa gctagcgcac ctgcactttg aattcttgct tctttttttat    5220 tactgttatg attttgcttt ttacagatgt tggacgattt tttcttctga ttgttgaatt    5280
cataatcatg gtctcatttc ctttgcttct tggaatatt tctttcaaca cattccttta    5340
ttttattata cattgtgtcc ttttttttagc tattgctgct gttgttttt attctattta    5400 caggatgatt tttaaactgt caaatgaagt agtgttaacc tcaaataggc taaatgtgaa    5460
```
caaataaaat acagcaaata ctcagaaaaa aaaaaaaaaa aaaaaaa                  5507

<210> SEQ ID NO 16
<211> LENGTH: 3342
<212> TYPE: DNA
<213> ORGANISM: Homo sapiens

<400> SEQUENCE: 16

| | | | | | |
|---|---|---|---|---|---|
| aatatcaacc | tgtttcctcc | tcctccttct | cctcctcctc | cgtgacctcc | tcctcctctt | 60 |
| tctcctgaga | aacttcgccc | cagcggtgcg | gagcgccgct | gcgcagccgg | ggagggacgc | 120 |
| aggcaggcgg | cgggcagcgg | gaggcggcag | cccggtgcgg | tccccgcggc | tctcggcgga | 180 |
| gccccgcgcc | cgccgcgcca | tggcccgaag | accccggcac | agcatatata | gcagtgacga | 240 |
| ggatgatgag | gactttgaga | tgtgtgacca | tgactatgat | gggctgcttc | ccaagtctgg | 300 |
| aaagcgtcac | ttggggaaaa | caaggtggac | ccgggaagag | gatgaaaaac | tgaagaagct | 360 |
| ggtggaacaa | aatggaacag | atgactggaa | agttattgcc | aattatctcc | cgaatcgaac | 420 |
| agatgtgcag | tgccagcacc | gatggcagaa | agtactaaac | cctgagctca | tcaagggtcc | 480 |
| ttggaccaaa | gaagaagatc | agagagtgat | agagcttgta | cagaaatacg | gtccgaaacg | 540 |
| ttggtctgtt | attgccaagc | acttaaaggg | gagaattgga | aaacaatgta | gggagaggtg | 600 |
| gcataaccac | ttgaatccag | aagttaagaa | aacctcctgg | acagaagagg | aagacagaat | 660 |
| tatttaccag | gcacacaaga | gactggggaa | cagatgggca | gaaatcgcaa | agctactgcc | 720 |
| tggacgaact | gataatgcta | tcaagaacca | ctggaattct | acaatgcgtc | ggaaggtcga | 780 |
| acaggaaggt | tatctgcagg | agtcttcaaa | agccagccag | ccagcagtgg | ccacaagctt | 840 |
| ccagaagaac | agtcatttga | tgggttttgc | tcaggctccg | cctacagctc | aactccctgc | 900 |
| cactggccag | cccactgtta | acaacgacta | ttcctattac | cacatttctg | aagcacaaaa | 960 |
| tgtctccagt | catgttccat | accctgtagc | gttacatgta | aatatagtca | atgtccctca | 1020 |
| gccagctgcc | gcagccattc | agagacacta | taatgatgaa | gaccctgaga | aggaaaagcg | 1080 |
| aataaaggaa | ttagaattgc | tcctaatgtc | aaccgagaat | gagctaaaag | gacagcaggt | 1140 |
| gctaccaaca | cagaaccaca | catgcagcta | ccccgggtgg | cacagcacca | ccattgccga | 1200 |
| ccacaccaga | cctcatggag | acagtgcacc | tgtttcctgt | ttgggagaac | accactccac | 1260 |
| tccatctctg | ccagcggatc | ctggctccct | acctgaagaa | agcgcctcgc | cagcaaggtg | 1320 |
| catgatcgtc | caccagggca | ccattctgga | taatgttaag | aacctcttag | aatttgcaga | 1380 |
| aacactccaa | tttatagatt | ctttcttaaa | cacttccagt | aaccatgaaa | actcagactt | 1440 |
| ggaaatgcct | tctttaactt | ccaccccccct | cattggtcac | aaattgactg | ttacaacacc | 1500 |
| atttcataga | gaccagactg | tgaaaactca | aaaggaaaat | actgttttta | gaaccccagc | 1560 |
| tatcaaaagg | tcaatcttag | aaagctctcc | aagaactcct | acaccattca | aacatgcact | 1620 |
| tgcagctcaa | gaaatttaaat | acggtcccct | gaagatgcta | cctcagacac | cctctcatct | 1680 |
| agtagaagat | ctgcaggatg | tgatcaaaca | ggaatctgat | gaatctggaa | ttgttgctga | 1740 |
| gtttcaagaa | aatggaccac | ccttactgaa | gaaaatcaaa | caagaggtgg | aatctccaac | 1800 |
| tgataaatca | ggaaacttct | tctgctcaca | ccactgggaa | ggggacagtc | tgaatacccca | 1860 |
| actgttcacg | cagacctcgc | ctgtggcaga | tgcaccgaat | attcttacaa | gctccgtttt | 1920 |
| aatggcacca | gcatcagaag | atgaagacaa | tgttctcaaa | gcatttacag | tacctaaaaa | 1980 |
| caggtccctg | gcgagcccct | tgcagccttg | tagcagtacc | tgggaacctg | catcctgtgg | 2040 |
| aaagatggag | gagcagatga | catcttccag | tcaagctcgt | aaatacgtga | atgcattctc | 2100 |

| | |
|---|---:|
| agcccggacg ctggtcatgt gagacatttc cagaaaagca ttatggtttt cagaacactt | 2160 |
| caagttgact tgggatatat cattcctcaa catgaaactt ttcatgaatg ggagaagaac | 2220 |
| ctatttttgt tgtggtacaa cagttgagag cagcaccaag tgcatttagt tgaatgaagt | 2280 |
| cttcttggat ttcacccaac taaaaggatt tttaaaaata aataacagtc ttacctaaat | 2340 |
| tattaggtaa tgaattgtag ccagttgtta atatcttaat gcagattttt ttaaaaaaaa | 2400 |
| cataaaatga tttatctgta ttttaaagga tccaacagat cagtattttt tcctgtgatg | 2460 |
| ggttttttga aatttgacac attaaaaggt actccagtat ttcactttc tcgatcacta | 2520 |
| aacatatgca tatatttta aaaatcagta aaagcattac tctaagtgta gacttaatac | 2580 |
| catgtgacat ttaatccaga ttgtaaatgc tcatttatgg ttaatgacat tgaaggtaca | 2640 |
| tttattgtac caaaccattt tatgagtttt ctgttagctt gctttaaaaa ttattactgt | 2700 |
| aagaaatagt tttataaaaa attatatttt tattcagtaa tttaattttg taaatgccaa | 2760 |
| atgaaaaacg ttttttgctg ctatggtctt agcctgtaga catgctgcta gtatcagagg | 2820 |
| ggcagtagag cttggacaga aagaaaagaa acttggtgtt aggtaattga ctatgcacta | 2880 |
| gtatttcaga cttttaatt ttatatatat atacattttt tttccttctg caatacatttt | 2940 |
| gaaaacttgt ttgggagact ctgcattttt tattgtggtt tttttgttat tgttggttta | 3000 |
| tacaagcatg cgttgcactt cttttttggg agatgtgtgt tgttgatgtt ctatgttttg | 3060 |
| ttttgagtgt agcctgactg ttttataatt tgggagttct gcatttgatc cgcatcccct | 3120 |
| gtggttccta agtgtatggt ctcagaactg ttgcatggat cctgtgtttg caactgggga | 3180 |
| gacagaaact gtggttgata gccagtcact gccttaagaa catttgatgc aagatggcca | 3240 |
| gcactgaact tttgagatat gacggtgtac ttactgcctt gtagcaaaat aaagatgtgc | 3300 |
| ccttatttta cctaaaaaaa aaaaaaaaaa aaaaaaaaa aa | 3342 |

<210> SEQ ID NO 17
<211> LENGTH: 1792
<212> TYPE: DNA
<213> ORGANISM: Homo sapiens

<400> SEQUENCE: 17

| | |
|---|---:|
| tgcagatgcc ctgtgccgtg cagctcagca tgcataggtg gggtagttgg ttgatgagct | 60 |
| tttctttagg agaacagatt ttgagctatc ttttttttgtt ggaaccctgc acacaactgt | 120 |
| cattatgtag atggttttcc tctcaggtgg ttggttttct ccagagaaga acccttgaat | 180 |
| ctcctgcctg tggaggtgga cgtgtggttg gtgttctggg tgcccttgc cctgagctct | 240 |
| gttctccatg gtgcctgttt cctgggtctg cagcccttc tcagtttctc tgaagagtaa | 300 |
| acctctcccc tgcttgggga ggagcatggg ggttacgtag tagcctggct gcataacatg | 360 |
| ggcttagtag ctcagttttc catcatgaac cagagcctca tctttcatgg ttcctgtgcc | 420 |
| tccgagggct gggctactgg ggtgtctgtc agtccagatg gctttgttct caagtttcct | 480 |
| ccacagtgga tatgaatgtt tgcaacttac actcaattac aacgctttcc tctacttttc | 540 |
| tccaagtttg ctgaaatctt tatttgtgga tatctcctct ctttttgctt tgtcctcata | 600 |
| ggttaaaacg ttttaaaatt ccctaacagt aggaaattta gtagggtttt ggaagggaga | 660 |
| ggaggtgtaa gatggtcact cttccatgtt taactggaag tggaaagtct aggcttttgc | 720 |
| ttcaggcctg ggaggtgcac atgaaacagt ccctcccagt ggctgcctgg ggggtccctg | 780 |
| aagggtgtga gaccaccgtg aatcctgggg cagggcactt gcagtacatg tgctatgtgt | 840 |
| ttgctagtat tgttttagat gtttgatctc ctagcctttg cttttctttg tattttctcct | 900 |

```
gctttagtcc atttcccttc tagctccttc tgttctcatt tatcttctgc tgctgcttgg      960
agttacattt tcagcaagtc tgtaacacct ctctgaacca aaggctctca agttcatctt     1020
tctttctcca agcctacgcc tgtgctgctg tcatgagtgg cgagcttctg tttcttctgt     1080
cttcttgtca gtcccaagtg ccctttaca gagaatgcct gtttttcact gtctagctca      1140
gttaccagga gtccctgtga atgacaccca caggtccctc aaagaagtca gatttctctt     1200
ggacctgata aagcaaacaa aatgtgaccc aagcaggctg agttggacgg gtcccttctt     1260
accttcgccc tctgccatgt tgacattctt atctgatggc acaggctggg agttcaggat     1320
ccacttagat ggggtccgtt caggggatac cagcgttcac attttccctt ttaagaaagg     1380
gtcttggcct gaatgttccc catccggaca caggctgcat gtctctgtga gtgtcaaagc     1440
tgccatgacc atctcggtaa cctactctta ctccacaatg tctatattca ctgcagggct     1500
ctatgattag tccataatgt aaatgcctgg cccaagacgt atggcctgag tttatccaag     1560
gcccaaacaa ttaccaaaca ttcctcttag atagaagaca gatttctttc ccttggcaaa     1620
gatcttctac taagatatgt tacaggatgt tttacattct cttggtctta taataacacc     1680
acgcccaatc cagtatttga tgcgtcggtg gtcactcgga aggttgttat tttaaaaata     1740
cttattgttc tcagtctgca gttctcacag ctgtaaaaaa aaaaaaaaaa aa             1792

<210> SEQ ID NO 18
<211> LENGTH: 2240
<212> TYPE: DNA
<213> ORGANISM: Homo sapiens

<400> SEQUENCE: 18
cgccgggcca ctggcacttg cttctgcggc gagtcccacc cacgaccgca gcccagcaac       60
tcgcaaacgc aacctgaagc ctgggctgcg cagtgtggga gggcttcgcg atcttggggg      120
acccattccg aacttgcaga ggaccgtagc tctcctggcc tggagagtgt gaacaggatt      180
gtggactctt ccaagattca caatgatatg gtgaatccaa agactggaac caaaaagatt      240
tactcagtgc tttagttta acaacagtaa attgtctacc acacccatc atggctaaaa        300 gtgcggaggt caaactggca atatttggga gagcaggcgt gggcaagtca gctcttgtag      360
tgagatttct gaccaaacgg ttcatctggg aatatgatcc caccctcgaa tcaacctacc      420
gacaccaagc aaccatcgat gatgaagttg tttccatgga gatactagac actgctggtc      480
aggaagatac cattcagagg gaggggcaca tgcgatgggg ggaaggcttt gtgctggtct      540
acgacattac tgaccgagga agttttgagg aagtgctgcc acttaagaac atcctagatg      600
agatcaaaaa gcccaagaat gtgactctca tcttggttgg aaacaaagct gacttggacc      660
actccaggca ggttagcaca gaagaaggag agaagctggc cacagaattg gcttgtgctt      720
tttacgagtg ctctgcctgc actggagaag ggaacatcac agagatattc tatgaattgt      780
gtcgagaggt gcgtcgccgg aggatggtgc agggcaagac gaggcgacgc agctccacca      840
cgcatgtcaa gcaagccatt aacaagatgc tcaccaaaat cagtagttag gcagcccagc      900
tgaggtggac caactaattg gaaacactct tccccttctg ttccccttc aaaaataaaa       960 caaaatattg cattctttgt ttggattctg agaaatgtct gggcttccca ttgtttctgg     1020
cctctaatag gttgggaagt tttagcgtgt tttatgcaat ttcagtgcta acaatttctt     1080
cctttcctgc ttgaataaga tacactctaa tggcatttga acatgtaatc accagagatt     1140
ctgaaatgac tggtttatgt taagctattt ttaggcatct tcaccttgct ttaagtaggt     1200
tgaagttttt gcaaaggcat ttaaaaattc aatttcttgt cagatactac aaataatttt     1260
```

| | | | | |
|---|---|---|---|---|
| cttaaaagtc | taagatagca | gaaaatacag | taaaaacaca | ggagaagaag ctgagctatt | 1320 |
| ggaacaggaa | atagaaggaa | ctctagtttc | tgtttgaagt | gaggatttc tgaattatct | 1380 |
| aatatcatct | aggttttctt | taaaatttta | ttttgttctt | cagttcaagc atcttctcac | 1440 |
| taatgttttt | cactataaca | gagaattcat | ttcaatttga | gttggttctc tcaatgatct | 1500 |
| attgatcatt | acaccctaac | tctccttcct | tggctcaaac | aatatttcc ctataacaaa | 1560 |
| ggcaatagga | cacaaaattc | acatcctgct | gggccttttt | tcatcaagtc agggtgatat | 1620 |
| aaaaacattg | gaagtctttt | caccaaaccc | tgactttatt | gaatgctagt agaagatgta | 1680 |
| gaattagaga | catctgattt | gtttatcacc | ttagcagaaa | aaccacagtc caaaagacaa | 1740 |
| gcaaattaag | aatggagctt | aaccatgcct | ccattgggaa | gtctagactt tgagccaggt | 1800 |
| acagtaagaa | aaattagcct | ctgattcatt | aagtttgcca | catgacttat tttgatattt | 1860 |
| tggatacatt | aactcactta | ggagaattca | gaaaagaatg | ggtgattaaa gttcattaca | 1920 |
| gctgaataaa | tgtgtctaaa | acagactctt | gtattctgaa | agtacagtct acaactgata | 1980 |
| aaaccttatg | attcttttct | ccccccattat | gcccctatat | atatcaagat ttgggtactt | 2040 |
| tattttagta | gaaaatatat | atcttttaca | tatgtatgta | tttataaatg catagatata | 2100 |
| tgtataaaaa | tttgtaagcg | ttagcggcat | taattcacca | atgcatttgg acaacttgat | 2160 |
| gtaactgact | ttattttatg | tgactataat | aaaaagcata | attttctcat tctgtcaaaa | 2220 |
| aaaaaaaaaa | aaaaaaaaa | | | | 2240 |

```
<210> SEQ ID NO 19
<211> LENGTH: 3124
<212> TYPE: DNA
<213> ORGANISM: Homo sapiens

<400> SEQUENCE: 19
```

| | | | | |
|---|---|---|---|---|
| taagatccac | atcagctcaa | ctgcacttgc | ctcgcagagg | cagcccgctc acttcccgcg | 60 |
| gaggcgctcc | ccggcgccgc | gctccgcggc | agccgcctgc | ccccggcgct gccccgcccc | 120 |
| gccgcgccgc | cgccgccgcc | gcgcacgccg | cgccccgcag | ctctgggctt cctcttcgcc | 180 |
| cgggtggcgt | tgggcccgcg | cgggcgctcg | ggtgactgca | gctgctcagc tcccctcccc | 240 |
| cgccccgcgc | cgcgcggccg | cccgtcgctt | cgcacagggc | tggatggttg tattgggcag | 300 |
| ggtggctcca | ggatgttagg | aactgtgaag | atggaagggc | atgaaaccag cgactggaac | 360 |
| agctactacg | cagacacgca | ggaggcctac | tcctccgtcc | cggtcagcaa catgaactca | 420 |
| ggcctgggct | ccatgaactc | catgaacacc | tacatgacca | tgaacaccat gactacgagc | 480 |
| ggcaacatga | ccccggcgtc | cttcaacatg | tcctatgcca | acccgggcct aggggccggc | 540 |
| ctgagtcccg | gcgcagtagc | cggcatgccg | ggggctcgg cgggcgccat gaacagcatg | 600 |
| actgcggccg | gcgtgacggc | catgggtacg | gcgctgagcc | cgagcggcat gggcgccatg | 660 |
| ggtgcgcagc | aggcggcctc | catgaatggc | ctgggcccct | acgcggccgc catgaacccg | 720 |
| tgcatgagcc | ccatggcgta | cgcgccgtcc | aacctgggcc | gcagccgcgc gggcggcggc | 780 |
| ggcgacgcca | agacgttcaa | gcgcagctac | ccgcacgcca | agccgcccta ctcgtacatc | 840 |
| tcgctcatca | ccatggccat | ccagcaggcg | cccagcaaga | tgctcacgct gagcgagatc | 900 |
| taccagtgga | tcatggacct | cttcccctat | accggcaga | accagcagcg ctggcagaac | 960 |
| tccatccgcc | actcgctgtc | cttcaatgac | tgcttcgtca | aggtggcacg ctccccggac | 1020 |
| aagccgggca | agggctccta | ctggacgctg | caccgggact | ccggcaacat gttcgagaac | 1080 |
| ggctgctact | tgcgccgcca | gaagcgcttc | aagtgcgaga | agcagccggg ggccggcggc | 1140 |

| | |
|---|---|
| gggggcggga gcggaagcgg gggcagcggc gccaagggcg gccctgagag ccgcaaggac | 1200 |
| ccctctggcg cctctaaccc cagcgccgac tcgcccctcc atcggggtgt gcacgggaag | 1260 |
| accggccagc tagagggcgc gccggccccc gggcccgccg ccagccccca gactctggac | 1320 |
| cacagtgggg cgacgcgac aggggggcgcc tcggagttga agactccagc ctcctcaact | 1380 |
| gcgcccccca taagctccgg gccggggcg ctggcctctg tgcccgcctc tcacccggca | 1440 |
| cacggcttgg caccccacga gtcccagctg cacctgaaag ggaccccca ctactccttc | 1500 |
| aaccacccgt tctccatcaa caacctcatg tcctcctcgg agcagcagca taagctggac | 1560 |
| ttcaaggcat acgaacaggc actgcaatac tcgccttacg gctctacgtt gcccgccagc | 1620 |
| ctgcctctag gcagcgcctc ggtgaccacc aggagcccca tcgagccctc agccctggag | 1680 |
| ccggcgtact accaaggtgt gtattccaga cccgtcctaa acacttccta gctcccggga | 1740 |
| ctgggggggtt tgtctggcat agccatgctg gtagcaagag agaaaaaatc aacagcaaac | 1800 |
| aaaaccacac aaaccaaacc gtcaacagca taataaaatc ccaacaacta ttttttatttc | 1860 |
| atttttcatg cacaaccttt cccccagtgc aaaagactgt tactttatta ttgtattcaa | 1920 |
| aattcattgt gtatattact acaaagacaa ccccaaacca atttttttcc tgcgaagttt | 1980 |
| aatgatccac aagtgtatat atgaaattct cctccttcct tgcccccctc tctttcttcc | 2040 |
| ctctttcccc tccagacatt ctagtttgtg gagggttatt taaaaaaaca aaaaaggaag | 2100 |
| atggtcaagt ttgtaaaata tttgtttgtg cttttttcccc ctccttacct gaccccctac | 2160 |
| gagtttacag gtctgtggca atactcttaa ccataagaat tgaaatggtg aagaaacaag | 2220 |
| tatacactag aggctcttaa aagtattgaa agacaatact gctgttatat agcaagacat | 2280 |
| aaacagatta taaacatcag agccatttgc ttctcagttt acatttctga tacatgcaga | 2340 |
| tagcagatgt ctttaaatga aatacatgta tattgtgtat ggacttaatt atgcacatgc | 2400 |
| tcagatgtgt agacatcctc cgtatattta cataacatat agaggtaata gataggtgat | 2460 |
| atacatgata cattctcaag agttgcttga ccgaaagtta caaggacccc aaccccttttg | 2520 |
| tcctctctac ccacagatgg ccctgggaat caattcctca ggaattgccc tcaagaactc | 2580 |
| tgcttcttgc tttgcagagt gccatggtca tgtcattctg aggtcacata acacataaaa | 2640 |
| ttagtttcta tgagtgtata ccatttaaag aatttttttt tcagtaaaag ggaatattac | 2700 |
| aatgttggag gagagataag ttatagggag ctggatttca aaacgtggtc caagattcaa | 2760 |
| aaatcctatt gatagtggcc attttaatca ttgccatcgt gtgcttgttt catccagtgt | 2820 |
| tatgcacttt ccacagttgg acatggtgtt agtatagcca gacgggtttc attattattt | 2880 |
| ctctttgctt tctcaatgtt aatttattgc atggtttatt cttttctttt acagctgaaa | 2940 |
| ttgctttaaa tgatggttaa aattacaaat taaattgtta attttatca atgtgattgt | 3000 |
| aattaaaaat attttgattt aaataacaaa aataatacca gattttaagc cgtggaaaat | 3060 |
| gttcttgatc atttgcagtt aaggacttta aataaatcaa atgttaacaa aaaaaaaaaa | 3120 |
| aaaa | 3124 |

```
<210> SEQ ID NO 20
<211> LENGTH: 5941
<212> TYPE: DNA
<213> ORGANISM: Homo sapiens

<400> SEQUENCE: 20
```

| | |
|---|---|
| agggattaag gggggggtgtg tgcggggcgg gtactgagtg ggcggggcct tgctcggta | 60 |
| actcccaggg gctggctaga gacccagagg cgcagagcgg agaggcctgc ggcgaggatg | 120 |

-continued

```
gagggcctgg cagtgcggtt gctgcgcggc agcaggctgc taagaagaaa tttcctgact    180
tgtttgtctt cttggaagat tcctcctcat gtctcaaaat cttcccagtc agaagctcta    240
ctcaatataa caaataatgg aatacacttt gctcccctgc aaacatttac agatgaggaa    300
atgatgataa agagttcagt taaaaaattt gctcaggaac aaattgcacc tttggtttca    360
accatggatg aaaattcgaa aatggagaaa tcagtaatac aaggattatt caacaaggg     420 ttgatgggta ttgaagttga cccagaatat ggaggcacag gagcttcatt tttatccact    480
gtgctcgtga tagaggaatt agccaaagtt gatgcatctg tggctgtctt ttgtgagatc    540
cagaacacat taattaacac actgattaga aacatggaa cagaagaaca aaaggccacc     600
tatttgcctc agctcactac agaaaaagta ggaagtttct gcctttcaga ggctggagca    660
ggtagtgact catttgcttt gaagaccaga gctgataaag agggagatta ttatgtcctc    720
aatggatcaa agatgtggat cagcagtgct gagcacgcag ggctcttcct ggtgatggca    780
aatgtagacc ctaccattgg atataaggga attacctcct tcttagtaga tcgtgatact    840
ccgggccttc atatagggaa acctgaaaac aaattggggc tcagagcttc ttccacctgc    900
ccgttaacat tcgaaaatgt caaggttcca gaagccaata tcttgggaca aattggacat    960
ggctataagt atgccatagg gagtctcaat gaaggtagaa taggaattgc tgcacagatg   1020
ctgggactgg cgcaaggatg ttttgactac actattccat atattaaaga aaggatacaa   1080
tttggcaaaa gactatttga ttttcagggc ctccaacacc aagtggctca cgtggccacc   1140
cagctggaag ctgcaagatt actaacatac aatgctgcta ggcttttaga agctggaaag   1200
ccattcataa agaagcgtc aatggccaaa tactatgcat cagagattgc aggacaaaca    1260
acgagtaaat gtatcgagtg gatgggggga gtaggctaca ccaaagatta ccctgtggag   1320
aaatacttcc gagatgcaaa gattggtacg atatatgaag gagcttccaa catccagttg   1380
aacaccattg caaagcatat cgatgcagaa tactgacgtc tataggagtg ggacccctcc   1440
ctggtgtcac tgctgtaaaa ttttaaacgg ttgtgtcttg ttgggagtaa gtgccttgcg   1500
tgggaataaa cttccacagc attcgaatat tttaatgaag cccttagtca gggtcctggt   1560
gttggccttt ttggttttct cttttcaggc tgtttaactt aggcacagga gatccacttt   1620
taaacttggg aaataagcac ctgtattttt ttccaaaact gttttttaaag ctgtatacgc   1680 atacatatat atatttttac tctgtcttac tctgtcaccc aggctagagt gcagtggcgc   1740
gatctcagct cactgcagcc ttgacctcct gggttccagt gattctcatg cctcatcctc   1800
ccaagtagct ggaactacag gtgtgcacca ccatgcctgg ttcattttg tgttttagt     1860 agagatgggg ttttaccata ttgcccaggc tggtcttctg gcttctggat atcgcccacc   1920
ttggcctccc aaagtgctgg gattacaggg atgagccacc gtgcctggct gggtatttat   1980
attatcattc tagtttcaga gtatacagaa gtttcatccc atcatttgga aaaataaagg   2040
catctgaagt acaatattac ttatagaaat agtttatatt cctattaaat cttaatcttg   2100
tggcatcagg gaaatatttg ttacatagta ggcaattttt atccagtact ttatagattc   2160
aactctaagt tgcaagcgaa gtcaaaactg atgaaaattt atttagaaaa atctaaaaat   2220 tctggttta aatatgagaa tcagtggaaa ataagggtat aattttgtag gtcatatgat    2280
tgaagaaaat attattttaa caatgtaaag caatatgatt tgttactata attaacctgt   2340
ataaaagata cattttatgg tggtttcagt aggtcatttt aaaaaccaat gtgcattagt   2400
tttcaagtat aaggtttaag taatttggtt taataatcag aaaatattca atacagtgtt   2460
ggatattctg tcatgcacta ttttcagtt gacaatttct gtattttaat tgaatactgt    2520
```

```
ttcttcagtc atggttattg cactttatcc tgaataataa ttcagaaatt gggttttggt    2580
tcagtgattc tcaagaaaaa gatctcttgc ccattaagaa gtgtatcaaa atctcataag    2640
gaatgaggga gagaaggggg ctgtagagtt tgaaaagca tattcaatat taaaatagtt    2700
ttatatttgg gaaggcaaaa atgaatctat tgttttgcaa tataggttat aaacaggcaa    2760
aatgcaataa aatatatatc tggttgtatt agtctgtttt cacgctgctg ataaagacat    2820
acctgagacc aggaagaaaa agaggtttaa ttggacttac agttccacat gactggggag    2880
gcctcagaat catggtggga ggcaaaaagc acttcttaca tggcggcagc aagagaaaat    2940
gagaaagaag caaagtggaa accccctaat aaacctatca gatcttgtga gacttactat    3000
cacgagaata gcacaggaaa gactggcccc catgattcaa ttacctcccc cgggtccctc    3060
ccacaacaca tgggaattct gagagatacc atttaagttg agatttcagt ggggacacag    3120
ccaaaccata tcattctacc cctggcacct ccaaatctca tgtcctcaca tttcaaaacc    3180
aatcatgcct tcccaacagt cccccaaagt cttaactcat ttcagcatta acccaaaagt    3240
ccgcagtcca aagtttcatc tgagacaagg caagtccctt ccacttatga acctgtaaaa    3300
tcaaaagtaa actagttact tcctagatac aatgggggta caggtattgg gtaaatacag    3360
ccattccaaa tgggagaaat tggccaacac aaaagggtaa cagggcccat gcaagtccaa    3420
aattcagcag ggcagtcaaa ttttaaacct ccaaaatgat cacctttgac tccacgtctc    3480
acaatcatct ctctcaagtt cgaagttcca caaatctcta aggcaaggga aagatgctgc    3540
cagtctcttt gctaaaacac agcaagagtc acctttactc cagttcccaa aaagtttttc    3600
atctccatct gagaccacct cagcctgaat tttattgtca atattgctat cagcattttg    3660
ggcaaagcca ttcagcaagt atctaggaag ttccaaactt tcccacattt tcctgtcttc    3720
ttctgagccc ttcaaactgt tccaacctct gcctgttacc cagttccaaa cttgctttca    3780
tattttggc tatcttttca gcaatgcccc actctactgt tagcagttta ctgtattagt    3840
ctgttttcac actgctgata aagacattcc tcaagattgt gaagaaaaag aggtttaatt    3900
ggacttacag ttccacatgg ccggggaggc ctcagaatca tggcgggagg tgaaaagcac    3960
ttcgtacatg gtggtggcaa gagaaaatga agaagaagca aaagtggaaa cccctgataa    4020
acccatcaga tctcatgaga cttactatca tgagaatagc acaggaaaga ctggcccccc    4080
tgattcgatg acctccccct gggtccctcc cacaacatgt gggaattcca gaagataaat    4140
tcaagttgca atttcagtgg ggacatagcc aaaccatatc actggtgatg ccacttcttc    4200
agtattaggg attctcagtc agaagagacc ccctgtgtgg cctgagtccc tcaggagga    4260
aggtggacaa cagagaaatg agagttttga tattttctga agaggaaca tgtgttagag    4320
atgaagaatc ttccaaggct catgcagttg cttagaataa tcattactgt tatatgagaa    4380
acattttagt aatttaataa aaggataatg tttatttaaa aaacctgact tttccagagt    4440
aattttgttt tgcacattca tgtttattga agtggactaa tttctataat gcaaatcaga    4500
gttaaatatt aaaaattgtg taaatacaat tgacatagga attacattaa aatattagga    4560
agaaacaagg acaaatttag accttgaatc cgaagagata aagcttactt gactttcaaa    4620
tggagagatg atgaaaaccc actcattcac tctttcagaa caaaaagaca gtcatctgat    4680
aagagtatga catggatgaa atgccctaca ggggccttgg acatctttaa tttctgcgat    4740
tatgtgaaag aggtggactt tacagataat ggagcagaag ccaacattag taaaaggaat    4800
cccaacttct tcccatagaa ttagaaacat gtgaaagtac aataaacttc ttgttcaaat    4860
taccagcatc agagagcttc ccatttgcat ctagaccttg aatttatatt tattgatcaa    4920
```

```
gttctaattt gtatgtatat tttgtgcata ttcaccaata acagttaaaa ttaattatgt      4980
gttatagtta atatatgcac ctaccttctt ccgttagtgc atcagtaaat gtgttatttt      5040
gtcatttttc caaagagagt gttgtaggtt ttccctgtag ttcttccttt atagcttttc      5100
ttctgataac catgacttca ggagctttaa aactatctat cttgcatttg tgtctggcgg      5160
agaactagcc atcagcctcc tgaagcctgc catcattgtt aatttgagga ctgggctgtc      5220
ttggggctca gaagataaag aactatttga gcagatgtgt gtgggtggca ctggattcca      5280
cccaactgcc aagttagtat tgttagagat ttcattttac aacacaaaaa taagcctgtg      5340
tcaaagattt taaaatcatg gaaagttaaa atctagaaag accttagaga accagccaac      5400
caactctctc atttttaaaag tgaaggattc atagcacaga ttacttgcct aagatcatcc      5460
aggaacgaag acaagaatcc aaatgtactt ggggacaaga attagtcccc aaattcagtg      5520
ttcttcctag tattaaacat tgccccttc gacaaatttt ggattcatt cttgttatat       5580 ttcagtactc ttgctgattt attttaggtt taactggtaa agaatgaaca tttcagaagt      5640
gttaggatta gtcagtgtca tcgcttatgt atatgaatca cttgccaaag cactggctc      5700 tcctcagctg taaccagcat gtcaaatgtg aagattattg tgtgggatcc tttggtttca      5760
ttgttatgat gtattttata aatgtactag ttatatcctt gtttatgtat ttttgctgat      5820 cttttcataaa gcagaatggt atgtatcgga ttgttttaat gttatatatt ggattgtatt    5880
cgatgttaca aaaccaatat tctatggaga atgaaaaaaa taaggacta aattaactgg      5940 a                                                                      5941

<210> SEQ ID NO 21
<211> LENGTH: 230
<212> TYPE: DNA
<213> ORGANISM: Homo sapiens

<400> SEQUENCE: 21
ggaacagaag aacaaaaggc cacctatttc cctcacctca ctacagaaaa agtaggaagt        60
tcctcccttt aaaaggctgg agcaggtagt gactcatttc ctttgaagac cagagctgat      120
aaagagggag attattatgt cctcaatggt tcaaagatgt ggttcaccag tgtgagcacg      180
cagggctctt cctggtgatg gcaaatgtag accctaccat tggatataag                230

<210> SEQ ID NO 22
<211> LENGTH: 283
<212> TYPE: DNA
<213> ORGANISM: Homo sapiens

<400> SEQUENCE: 22
ccatttgcta gcagtgtgac tcaagagaag ccagtaaccc ccctgagctt ccctagttca       60
caaaatgctt gtcatgaagt cgacagcttc cggaggctgc gaggctcgca agaaatgccc      120
acatgaatgt gcgcttaggg cgtgagtgct cactccagaa aactccaaca cagtgaaaag      180
gcagaagcgg tgttttttctt ttttacattt ttataagaat atataaaaaa tgatataaat     240
ggacatttac ggtagtgggg gaaggcatat atctacctcg agc                       283

<210> SEQ ID NO 23
<211> LENGTH: 316
<212> TYPE: DNA
<213> ORGANISM: Homo sapiens
<220> FEATURE:
<221> NAME/KEY: misc_feature
<222> LOCATION: (213)..(213)
<223> OTHER INFORMATION: "n" is any base or any nucleotide.
```

-continued

```
<400> SEQUENCE: 23
gtagatatat gccttccccc actaccgtaa atgtccattt atatcatttt ttatatattc    60
ttataaaaat gtaaaaaga aaaacaccgc ttctgccttt tcactgtgtt ggagttttct   120
ggagtgagca ctcacgccct aagcgcacat tcatgtgggc atttcttgcg agcctcgcag   180
cctccggaag ctgtcgactt catgacaagc atnttgtgaa ctagggaagc tcaggggggt   240
tactggcttc tcttgagtca cactgctagc aaatggcaga accaaagctc aaataaaaat   300
aaaataattt tcattc                                                   316

<210> SEQ ID NO 24
<211> LENGTH: 411
<212> TYPE: DNA
<213> ORGANISM: Homo sapiens

<400> SEQUENCE: 24
gctgagcaaa accattcaat aaagatttgt catttgatac atatggcaca atgtctgctg    60
agaaagctaa tcacactgat tgatccatgc attgaatgta cgaagagttg aagggaaagg   120
ggaaaggatg ataaagacaa tgtcatgaga tgtcagagaa aatactaatt tcataatgca   180
gctcaacaat agaaatcaat ttcaaaatga aatatgatgc ataaactaag attaaagtta   240
gttaatgtgg ctgggcatag cagatgggac tcttagaaga ggtggcctcc agggtggcag   300
ggccattgcc ctggctcagg ctcctgttcc ctcctgggcc caccaagttc actgggccct   360
cgcagcttcc aggcccctca ggcattcagc ttcaggtcgc tgatgtattt c             411

<210> SEQ ID NO 25
<211> LENGTH: 437
<212> TYPE: DNA
<213> ORGANISM: Homo sapiens

<400> SEQUENCE: 25
ggagttgtga gtttccaagc cccagctcac tctgaccact tctctgcctg cccagcatca    60
tgaagggcct tgcagctgcc ctccttgtcc tcgtctgcac catggccctc tgctcctgtg   120
cacaagttgg taccaacaaa gagctctgct gcctcgtcta tacctcctgg cagattccac   180
aaaagttcat agttgactat tctgaaacca gcccccagtg ccccaagcca ggtgtcatcc   240
tcctaaccaa gagaggccgg cagatctgtg ctgaccccaa taagaagtgg gtccagaaat   300
acatcagcga cctgaagctg aatgcctgag gggcctggaa gctgcgaggg cccagtgaac   360
ttggtgggcc caggagggaa caggagcctg agccagggca atggccctgc caccctggag   420
gccacctctt ctaagag                                                  437

<210> SEQ ID NO 26
<211> LENGTH: 462
<212> TYPE: DNA
<213> ORGANISM: Homo sapiens
<220> FEATURE:
<221> NAME/KEY: misc_feature
<222> LOCATION: (186)..(186)
<223> OTHER INFORMATION: "n" is any base or any nucleotide.
<220> FEATURE:
<221> NAME/KEY: misc_feature
<222> LOCATION: (459)..(459)
<223> OTHER INFORMATION: "n" is any base or any nucleotide.

<400> SEQUENCE: 26
acacacatgc tatgactcca atgttttaaa aaaataagcc ttaacagct ctgagacaca     60 tggcctcttc tgtatcccaa gcaaatccct aaatggaggt agagcacgtg ttcctatttt   120
```

```
tcacactctc atatgggaga taagtggtta aggaggacta gaaacccaat caggcctacc    180
ggggtnccgg acagacacac agcattccta aaggaatgcc accagagaaa aaatacaagt    240
ctgtacatat atctttattt tcatacttaa aaagaatcac atactcattc caacagcttt    300
accaggcttg gccaacccaa taagttacac actcactcag gtactaggaa ggttattgca    360
cagctcctta actgatcggg gtcaggggca gagtggtcac tttccccaca gccaggctct    420
gggatttgcc ctcctgtgaa gacaccatgc ctagcacang gt                        462
```

<210> SEQ ID NO 27
<211> LENGTH: 474
<212> TYPE: DNA
<213> ORGANISM: Homo sapiens

<400> SEQUENCE: 27

```
cttttgaggc aaacacatta ccaagagacc tacaaaagaa tatcacgggt tgaattcaca     60
ttccctgact ttgtaacaga gggagccagg gacctcattt caagactgtt gaagcataat    120
cccagccaga ggccaatgct cagagaagta cttgaacacc cctggatcac agcaaattca    180
tcaaaaccat caaattgcca aaacaaagaa tcagctagca acagtcttta ggaatcgtgc    240 aggggagaa atccttgagc cagggctgcc atataacctg acaggaacat gctactgaag    300 tttatttac cattgactgc tgccctcaat ctagaacgct acacaagaaa tatttgtttt     360
actcagcagg tgtgccttaa cctccctatt cagaaagctc cacatcaata aacatgacac    420
tctgaagtga aagtagccac gagaattgtg ctacttatac tgggtcataa tctg          474
```

<210> SEQ ID NO 28
<211> LENGTH: 516
<212> TYPE: DNA
<213> ORGANISM: Homo sapiens
<220> FEATURE:
<221> NAME/KEY: misc_feature
<222> LOCATION: (477)..(477)
<223> OTHER INFORMATION: "n" is any base or any nucleotide.

<400> SEQUENCE: 28

```
gctatgtatt gtaaatgatg agctatttgt gcggaatgcc agttctgaag agatccaaag     60
agccttcgct atgcctgcac ccacgccttc ctccagcccg gtgcccaccc tctctccaga    120
gcagcaggaa atgttgcaag cattctctac ccagtctggc atgaacctcg agtggtccca    180
gaagtgcctt caggacaaca actgggacta caccagatct gcccaggcct tcactcatct    240
caaggccaag ggcgagatcc agaagtggc attcatgaag tgatcgtagt catgcctcag    300
aagcagtccc ccctgtaaat agtccttgga tattaccgtc tggttgtcgt ctgtcatctc    360
ctcctgtctg gccgaggcc gccccgtgat gtgacgaggg agggagggtg ctgatcctct    420
cctcgctgct tctggaagac ttcagaagat tgagctcact ggtgccagga agcaaantta    480
ctttgtagac tgacactaaa ctacccgaag gactta                               516
```

<210> SEQ ID NO 29
<211> LENGTH: 255
<212> TYPE: DNA
<213> ORGANISM: Homo sapiens

<400> SEQUENCE: 29

```
agttgaatga actataataa cttgtctgac ataataagaa tgccacaggt ataacagata     60
aacctggcag gtggtccacg aatgagagtg tcacaaaata atcactcaac acaagggcca    120
cagacctgga gattcttccc agccatccct cactcctgcc ccaggacaca acccatgcag    180
```

```
gcccccattc cataggaaga ggcaggtccc acagtgtctg tggctagacc ttaacactga    240
gcagagatgc ccggg                                                    255

<210> SEQ ID NO 30
<211> LENGTH: 310
<212> TYPE: DNA
<213> ORGANISM: Homo sapiens

<400> SEQUENCE: 30
cccgggcatc tctgctcagt gttaaggtct agccacagac actgtgggac ctgcctcttc     60
ctatggaatg ggggcctgca tgggttgtgt cctggggcag gagtgaggga tggctgggaa    120
gaatctccag gtctgtggcc cttgtgttga gtgattattt tgtgacactc tcattcctgg    180
accacctgcc aggtttatct gttatacctg tggcattctt attatgtcag acaagttatt    240
atagttcatt caactctaac aaatgaacaa agaacaata aataggaggc cattaaaggt     300
cttttgtggc                                                          310

<210> SEQ ID NO 31
<211> LENGTH: 513
<212> TYPE: DNA
<213> ORGANISM: Homo sapiens
<220> FEATURE:
<221> NAME/KEY: misc_feature
<222> LOCATION: (425)..(425)
<223> OTHER INFORMATION: "n" is any base or any nucleotide.
<220> FEATURE:
<221> NAME/KEY: misc_feature
<222> LOCATION: (430)..(430)
<223> OTHER INFORMATION: "n" is any base or any nucleotide.
<220> FEATURE:
<221> NAME/KEY: misc_feature
<222> LOCATION: (491)..(491)
<223> OTHER INFORMATION: "n" is any base or any nucleotide.

<400> SEQUENCE: 31
cgcccgcaga ctctttgctc aagtacgaca ccccagtgct ggtgagccgg aacacggaga     60
aacggagccc caaggctcgg ctactgaaag tcagcccca gcagcctgga ccttcaggtt    120
cagccccaca gccacccaag accaagctcc cctcaactcc ctgtgtccca gatcctacaa    180
agcaggcaga agaaatcttg aatgccatac tacccccaag ggagtgggtg aagacacgc    240 agctatggat ccagcaggtg tccagcaccc ctagcaccag gatggacgtg gtgcacctcc    300
aggagcagtt agacttaaag ctgcagcagc ggcaggccag ggaaacaggc atctgccctg    360
tccgcaggga actctactca cagtgttttg atgagttgat ccgggaggtc accatcaact    420
gtgcngagan ggggctgctg ctgctgcgag ttccgggacg agatccgcat gaaccatcgc    480
tgctaccaga ncctgtacga gagagcgtgg cgt                                513

<210> SEQ ID NO 32
<211> LENGTH: 267
<212> TYPE: DNA
<213> ORGANISM: Homo sapiens
<220> FEATURE:
<221> NAME/KEY: misc_feature
<222> LOCATION: (148)..(173)
<223> OTHER INFORMATION: "n" is any base or any nucleotide.

<400> SEQUENCE: 32
ggttaacact acttcatttg acagtttaaa aatcatcctg taaatagaat aaaaaacaac     60
agcagcaata gctaaaaaaa ggacacaatg tataataaaa taaggaatg tgttgaaaga    120 aatattccaa agaagcaaag gaaatgannn nnnnnnnnn nnnnnnnnn nnngaagaaa    180
```

-continued

| aaatcgtcca acatctgtaa aaagcaaaat cataacagta ataaaaaaga agcaagaatt | 240 |
| caaagtgcag gtgcgctagt ctcgagc | 267 |

<210> SEQ ID NO 33
<211> LENGTH: 306
<212> TYPE: DNA
<213> ORGANISM: Homo sapiens

<400> SEQUENCE: 33

| agctagcgca cctgcacttt gaattcttgc ttctttttta ttactgttat gattttgctt | 60 |
| tttacagatg ttggacgatt ttttcttctg attgttgaat tcataatcat ggtctcattt | 120 |
| cctttgcttc tttggaatat ttctttcaac acattccttt attttattat acattgtgtc | 180 |
| cttttttag ctattgctgc tgttgttttt tattctattt acaggatgat ttttaaactg | 240 |
| tcaaatgaag tagtgttaac ctcaaatagg ctaaatgtga acaaataaaa tacagcaaat | 300 |
| actcag | 306 |

<210> SEQ ID NO 34
<211> LENGTH: 558
<212> TYPE: DNA
<213> ORGANISM: Homo sapiens
<220> FEATURE:
<221> NAME/KEY: misc_feature
<222> LOCATION: (157)..(157)
<223> OTHER INFORMATION: "n" is any base or any nucleotide.
<220> FEATURE:
<221> NAME/KEY: misc_feature
<222> LOCATION: (159)..(159)
<223> OTHER INFORMATION: "n" is any base or any nucleotide.
<220> FEATURE:
<221> NAME/KEY: misc_feature
<222> LOCATION: (289)..(289)
<223> OTHER INFORMATION: "n" is any base or any nucleotide.
<220> FEATURE:
<221> NAME/KEY: misc_feature
<222> LOCATION: (349)..(350)
<223> OTHER INFORMATION: "n" is any base or any nucleotide.
<220> FEATURE:
<221> NAME/KEY: misc_feature
<222> LOCATION: (482)..(482)
<223> OTHER INFORMATION: "n" is any base or any nucleotide.
<220> FEATURE:
<221> NAME/KEY: misc_feature
<222> LOCATION: (542)..(543)
<223> OTHER INFORMATION: "n" is any base or any nucleotide.

<400> SEQUENCE: 34

| agtacaccgt catatctcaa aagttcagtg ctggccatct tgcatcaaat gttcttaagg | 60 |
| cagtgactgg ctatcaacca cagtttctgt ctccccagtt gcaaacacag gatccatgca | 120 |
| acagttctga gaccatacac ttagaaacca cagggntnc ggatcaaatg cagaactccc | 180 |
| aaattataaa acagtcaggc tacactcaaa acaaaacata gaacatcaac aacacacatc | 240 |
| tcccaaaaaa gaagtgcaac gcatgcttgt ataaccaac aataataana aaaccacaat | 300 |
| aaaaaatgca gagtctccca aacaagtttt caaatgtatt gcagaaggnn aaaaaatgta | 360 |
| tatatatata aaattaaaaa gtctgaaata ctagtgcata gtcaattacc taacaccaag | 420 |
| tttcttttct ttctgtccaa gctctactgc ccctctgata ctagcagcat gtctacaggc | 480 |
| tnttgaccat agcagcaaaa aacgtttttc atttggcatt tacaaaattt aattactggt | 540 |
| annaatataa ttttttat | 558 |

<210> SEQ ID NO 35
<211> LENGTH: 394
<212> TYPE: DNA

```
<213> ORGANISM: Homo sapiens
<220> FEATURE:
<221> NAME/KEY: misc_feature
<222> LOCATION: (50)..(50)
<223> OTHER INFORMATION: "n" is any base or any nucleotide.
<220> FEATURE:
<221> NAME/KEY: misc_feature
<222> LOCATION: (53)..(53)
<223> OTHER INFORMATION: "n" is any base or any nucleotide.
<220> FEATURE:
<221> NAME/KEY: misc_feature
<222> LOCATION: (208)..(225)
<223> OTHER INFORMATION: "n" is any base or any nucleotide.
<220> FEATURE:
<221> NAME/KEY: misc_feature
<222> LOCATION: (327)..(327)
<223> OTHER INFORMATION: "n" is any base or any nucleotide.
<220> FEATURE:
<221> NAME/KEY: misc_feature
<222> LOCATION: (346)..(346)
<223> OTHER INFORMATION: "n" is any base or any nucleotide.
<220> FEATURE:
<221> NAME/KEY: misc_feature
<222> LOCATION: (379)..(379)
<223> OTHER INFORMATION: "n" is any base or any nucleotide.

<400> SEQUENCE: 35
atcattcctc aacatgaaac ttttcatgaa tgggagaaga acctattttn gtngtggtac      60
aacagttgag agcagcacca agtgcattta gttgaatgaa gtcttcttgg atttcaccca     120
actaaaagga tttttaaaaa taaataacag tcttacctaa attattaggt aatgaattgt     180
agccagttgt taatatctta atgcagannn nnnnnnnnnn nnnnntaaaa tgatttatct     240
gtatttaaaa ggatccaaca gatcagtatt ttttcctgtg atgggttttt tgaaatttga     300
cacattaaaa ggtactccag tatttcnctt tctcgatcac taaacnatat gcctatattt     360
ttaaaaatca gtaaaagcnt tactcctaag tgta                                 394

<210> SEQ ID NO 36
<211> LENGTH: 360
<212> TYPE: DNA
<213> ORGANISM: Homo sapiens

<400> SEQUENCE: 36
aacaaccttc cgagtgacca ccgacgcatc aaatactgga ttgggcgtgg tgttattata      60
agaccaagag aatgtaaaac atcctgtaac atatcttagt agaagatctt tgccaaggga     120
aagaaatctg tcttctatct aagaggaatg tttggtaatt gtttgggcct tggataaact     180
caggccatac gtcttgggcc aggcatttac attatggact aatcatagag ccctgcagtg     240
aatatagaca ttgtggagta agagtaggtt accgagatgg tcatggcagc tttgacactc     300
acagagacat gcagcctgtg tccggatggg aacattcag gccaagaccc ttcttaaaag     360

<210> SEQ ID NO 37
<211> LENGTH: 416
<212> TYPE: DNA
<213> ORGANISM: Homo sapiens

<400> SEQUENCE: 37
cctgctttag tccatttccc ttctagctcc ttctgttctc atttatcttc tgctgctgct      60
tggagttaca ttttcagcaa gtctgtaaca cctctctgaa ccaaaggctc tcaagttcat     120 cttctttct ccaagcctac gcctgtgctg ctgtcatgag tggcgagctt ctgtttcttc     180
tgtcttcttg tcagtcccaa gtgccctttt acagagaatg cctgttttc actgtctagc     240 tcagttacca ggagtccctg tgaatgacac ccacaggtcc ctcaaagaag tcagatttct     300
```

```
cttggacctg ataaagcaaa caaaatgtga cccaagcagg ctgagttgga cgggtccctt    360
cttaccttcg ccctctgcca tgttgacatt cttatctgat ggcacaggct gggagt        416
```

<210> SEQ ID NO 38
<211> LENGTH: 272
<212> TYPE: DNA
<213> ORGANISM: Homo sapiens

<400> SEQUENCE: 38

```
acataaaata aagtcagtta catcaagttg tccaaatgca ttggtgaatt aatgccgcta     60
acgcttacaa atttttatac atatatctat gcatttataa atacatacat atgtaaaaga   120
tatatatttt ctactaaaat aaagtaccca aatcttgata tatataggg cataatgggg   180 gagaaaagaa tcataaggtt ttatcagttg tagactgtac tttcagaata caagagtctg   240
ttttagacac atttattcag ctgtaatgaa ct                                  272
```

<210> SEQ ID NO 39
<211> LENGTH: 424
<212> TYPE: DNA
<213> ORGANISM: Homo sapiens

<400> SEQUENCE: 39

```
gatttgttta tcaccttagc agaaaaacca cagtccaaaa gacaagcaaa ttaagaatgg     60
agcttaacca tgcctccatt gggaagtcta gactttgagc caggtacagt aagaaaaatt   120
agcctctgat tcattaagtt tgccacatga cttattttga tattttggat acattaactc   180
acttaggaga attcagaaaa gaatgggtga ttaaagttca ttacagctga ataaatgtgt   240
ctaaaacaga ctcttgtatt ctgaaagtac agtctacaac tgataaaacc ttatgattct   300
tttctccccc attatgcccc tatatatatc aagatttggg tactttattt tagtagaaaa   360
tatatatctt ttacatatgt atgtatttat aaatgcatag atatatgtat aaaaatttgt   420
aagc                                                                 424
```

<210> SEQ ID NO 40
<211> LENGTH: 450
<212> TYPE: DNA
<213> ORGANISM: Homo sapiens
<220> FEATURE:
<221> NAME/KEY: misc_feature
<222> LOCATION: (5)..(5)
<223> OTHER INFORMATION: "n" is any base or any nucleotide.
<220> FEATURE:
<221> NAME/KEY: misc_feature
<222> LOCATION: (8)..(8)
<223> OTHER INFORMATION: "n" is any base or any nucleotide.
<220> FEATURE:
<221> NAME/KEY: misc_feature
<222> LOCATION: (35)..(35)
<223> OTHER INFORMATION: "n" is any base or any nucleotide.
<220> FEATURE:
<221> NAME/KEY: misc_feature
<222> LOCATION: (44)..(44)
<223> OTHER INFORMATION: "n" is any base or any nucleotide.
<220> FEATURE:
<221> NAME/KEY: misc_feature
<222> LOCATION: (64)..(64)
<223> OTHER INFORMATION: "n" is any base or any nucleotide.
<220> FEATURE:
<221> NAME/KEY: misc_feature
<222> LOCATION: (97)..(97)
<223> OTHER INFORMATION: "n" is any base or any nucleotide.
<220> FEATURE:
<221> NAME/KEY: misc_feature
<222> LOCATION: (104)..(104)
<223> OTHER INFORMATION: "n" is any base or any nucleotide.
<220> FEATURE:

```
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (431)..(431)
<223> OTHER INFORMATION: "n" is any base or any nucleotide.

<400> SEQUENCE: 40
tcaanaanat tttccacggc ttaaaatctg gtatnatttt tgtnatttaa atcaaaatat    60
tttnaattac aatcacattg ataaaaatta acaattnaat ttgnaatttt aaccatcatt   120
taaagcaatt tcagctgtaa agaaaaagaa taaaccatgc aataaattaa cattgagaaa   180
gcaaagagaa ataataatga aacccgtctg gctatactaa caccatgtcc aactgtggaa   240
agtgcataac actggatgaa acaagcacac gatggcaatg attaaaatgg ccactatcaa   300
taggattttt gaatcttgga ccacgttttg aaatccagct ccctataact tatctctcct   360
ccaacattgt aatantccct tttactgaaa aaaaaattct taaatggta tacactccat    420 agaaacctaa ntttatgggg ttatggtgac                                    450

<210> SEQ ID NO 41
<211> LENGTH: 569
<212> TYPE: DNA
<213> ORGANISM: Homo sapiens
<220> FEATURE:
<221> NAME/KEY: misc_feature
<222> LOCATION: (464)..(464)
<223> OTHER INFORMATION: "n" is any base or any nucleotide.
<220> FEATURE:
<221> NAME/KEY: misc_feature
<222> LOCATION: (520)..(520)
<223> OTHER INFORMATION: "n" is any base or any nucleotide.
<220> FEATURE:
<221> NAME/KEY: misc_feature
<222> LOCATION: (537)..(537)
<223> OTHER INFORMATION: "n" is any base or any nucleotide.
<220> FEATURE:
<221> NAME/KEY: misc_feature
<222> LOCATION: (541)..(541)
<223> OTHER INFORMATION: "n" is any base or any nucleotide.
<220> FEATURE:
<221> NAME/KEY: misc_feature
<222> LOCATION: (545)..(545)
<223> OTHER INFORMATION: "n" is any base or any nucleotide.

<400> SEQUENCE: 41
gttactttat tattgtattc aaaattcatt gtgtatatta ctacaaagac aaccccaaac    60 caatttttt cctgcgaagt ttaatgatcc acaagtgtat atatgaaatt ctcctccttc   120 cttgccccc tctctttctt ccctctttcc cctccagaca ttctagtttg tggagggtta   180
tttaaaaaaa caaaaaagga agatggtcaa gtttgtaaaa tatttgtttg tgcttttttcc  240 ccctccttac ctgacccct acgagtttac aggtctgtgg caatactctt aaccataaga   300
attgaaatgg tgaagaaaca agtatacact agaggctctt aaaagtattg aaagacaata   360
ctgctgttat atagcaagac ataaacagat tataaacatc agagccattt gcttctcagt   420
ttacatttct gatacatgca gatagcagat gtctttaaat gaantacatg tatattgtgt   480
atggacttaa ttatgcacat gctcagatgt gtagacatcn tccggatatt tacatancat   540
ntagnggaat agataggtga tatacatga                                    569
```